United States Patent
Kumar et al.

(10) Patent No.: US 8,822,400 B2
(45) Date of Patent: Sep. 2, 2014

(54) POLYOL OXIDASES

(71) Applicant: Danisco US Inc., Palo Alto, CA (US)

(72) Inventors: Manoj Kumar, Fremont, CA (US); Susan M. Madrid, South San Francisco, CA (US); Hugh C. McDonald, Carlsbad, CA (US); Ayrookaran J. Poulose, Belmont, CA (US); Thomas Rand, Brondby (DK); Huaming Wang, Fremont, CA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 13/745,541

(22) Filed: Jan. 18, 2013

(65) Prior Publication Data

US 2013/0196891 A1    Aug. 1, 2013

Related U.S. Application Data

(63) Continuation of application No. 13/044,466, filed on Mar. 9, 2011, now Pat. No. 8,383,568, which is a continuation of application No. 11/875,788, filed on Oct. 19, 2007, now Pat. No. 7,919,295.

(60) Provisional application No. 60/853,227, filed on Oct. 20, 2006, provisional application No. 60/853,258, filed on Oct. 20, 2006.

(30) Foreign Application Priority Data

Oct. 21, 2005  (DK) .................................. 2005 01474
Oct. 20, 2006  (WO) ................. PCT/DK2006/000590
Oct. 20, 2006  (WO) ................. PCT/DK2006/000591

(51) Int. Cl.
- *C11D 3/00*     (2006.01)
- *C12N 9/00*     (2006.01)
- *C12N 9/02*     (2006.01)
- *C12N 1/20*     (2006.01)
- *C12N 15/00*    (2006.01)
- *C07H 21/04*    (2006.01)

(52) U.S. Cl.
USPC ........ 510/392; 435/183; 435/189; 435/252.3; 435/320.1; 536/23.2

(58) Field of Classification Search
None
See application file for complete search history.

(56) References Cited

PUBLICATIONS

Chica et al. Curr Opin Biotechnol. Aug. 2005;16(4):378-84.*
Sen et al. Appl Biochem Biotechnol. Dec. 2007;143(3):212-23.*

* cited by examiner

*Primary Examiner* — Christian Fronda
(74) *Attorney, Agent, or Firm* — Danisco US Inc.

(57) ABSTRACT

The present invention provides compositions and methods for producing a polyol oxidase in micoroorganisms, and the use of polyol oxidases in cleaning compositions. The invention includes cleaning compositions that contain combinations of two or more POx oxidases, and cleaning compositions that contain combinations of two or more POx oxidases and a perhydrolase. In particular, the invention provides methods for expressing polyol oxidases in bacterial hosts for use in detergent applications for cleaning, bleaching and disinfecting.

15 Claims, 10 Drawing Sheets

POLYOL OXIDASES

CROSS-REFERENCE TO RELATED APPLICATIONS

This application is a continuation of U.S. application Ser. No. 13/044,466, filed Mar. 9, 2011, which is a continuation of U.S. application Ser. No. 11/875,788, filed Oct. 19, 2007, now U.S. Pat. No. 7,919,295, which claims priority to U.S. Provisional Application No. 60/853,227, filed Oct. 20, 2006, U.S. Provisional Application No. 60/853,258, filed on Oct. 20, 2006, and International Application No. PCT/DK2006/000590, filed on Oct. 20, 2006, which claims the benefit of Danish Application No. PA200501474, filed on Oct. 21, 2005, and International Application No. PCT/DK2006/000591, filed on Oct. 20, 2006, which claims the benefit of Danish Application No. PA200501474, filed on Oct. 21, 2005, the specifications of which are all herein incorporated by reference in their entirety.

FIELD OF THE INVENTION

The present invention provides compositions and methods for producing a polyol oxidase in microorganisms, and the use of polyol oxidases in cleaning compositions. The invention includes cleaning compositions that contain combinations of two or more POx oxidases, and cleaning compositions that contain combinations of two or more POx oxidases and a perhydrolase. In particular, the invention provides methods for expressing polyol oxidases in bacterial hosts for use in detergent applications for cleaning, bleaching and disinfecting.

BACKGROUND OF THE INVENTION

Oxidoreductases are enzymes that catalyze the transfer of electrons from one molecule (the reductant, also called the hydrogen acceptor or electron donor) to another (the oxidant, also called the hydrogen donor or electron acceptor). Oxidoreductases are classified as EC 1 in the EC number classification of enzymes. Oxidoreductases can be further classified into 22 subclasses, and the oxidoreductases belonging to EC class 1.1.3. act on the CH—OH group of donors with oxygen as acceptor. The oxidoreductase enzymes of the EC1.1.3 class of enzymes are oxidases, and their ability to generate hydrogen peroxide has found use in improving the storage stability of food products including cheese, butter, meat, wine and fruit juice (See e.g., Hammer, Oxidoreductases: Enzymes in Food Processing, Nagodawithana and Reed (eds). Academic Press, NY, [1998]; pp. 251-254; and Tiina and Sandholm, Int. J. Food Microbiol., 8:165-74 [1989]). Indeed, oxidases have found use as components of various compositions, including foods, personal care items, and detergents. However, there remains a need for methods and compositions that facilitate the efficient and economical production of oxidases for use in any suitable setting.

SUMMARY OF THE INVENTION

The present invention provides compositions and methods for producing a polyol oxidase in microorganisms, and the use of polyol oxidases in cleaning compositions. The invention includes cleaning compositions that contain combinations of two or more POx oxidases, and cleaning compositions that contain combinations of two or more POx oxidases and a perhydrolase. In particular, the invention provides methods for expressing polyol oxidases in bacterial hosts for use in detergent applications for cleaning, bleaching and disinfecting.

In one embodiment, the invention provides an isolated chimeric polynucleotide comprising a sequence encoding a mature polyol oxidase protein (POx) that is operably linked to a sequence encoding a secretory signal peptide, which is derived from a prokaryotic microorganism.

In another embodiment, the invention provides an isolated chimeric polynucleotide that encodes a mature polyol oxidase protein (POx) that is operably linked to a sequence encoding a secretory signal peptide derived from a *Streptomyces* sp., an *Acidothermus* sp. or an *Arthrobacter* sp.

In another embodiment, the invention provides for an isolated chimeric polynucleotide that encodes a polypeptide selected form SEQ ID NO:16, 28, 35, 37, 38, and 40, wherein the chimeric polynucleotide comprises a sequence encoding a mature polyol oxidase protein (POx) operably linked to a sequence encoding a secretory signal peptide, which is derived from a prokaryotic microorganism.

In another embodiment, the invention provides an isolated chimeric polynucleotide comprising a sequence encoding a mature polyol oxidase protein (POx) that is operably linked to a sequence encoding a secretory signal peptide, which is peptide is selected from the signal sequence encoded by the *S. coelicolor* gene SCO7637, the signal sequence encoding the *S. lividans* gene SCO 0624 and the signal sequence encoding the *B. subtilis* gene P43379.

In another embodiment, the invention provides for a recombinant expression vector comprising an isolated chimeric polynucleotide that comprises a sequence that encodes a mature polyol oxidase protein (POx) that is operably linked to a sequence encoding a secretory signal peptide derived from a *Streptomyces* sp., an *Acidothermus* sp. or an *Arthrobacter* sp.

In another embodiment, the invention provides a host cell that comprises a recombinant expression vector that an comprises isolated chimeric polynucleotide that comprises a sequence that encodes a mature polyol oxidase protein (POx) that is operably linked to a sequence encoding a secretory signal peptide derived from a *Streptomyces* sp., an *Acidothermus* sp. or an *Arthrobacter* sp.

In another embodiment, the invention provides a host cell that comprises a polynucleotide that encodes a POx polypeptide that has a sequence selected from SEQ ID NO:2, 4, 5, 6, 7, 8, 9, 10, 11, 12, 13, 14, 16, 28, 35, 37, 38 and 40.

In another embodiment, the invention provides a host cell that comprises a polynucleotide that encodes a POx polypeptide that has sorbitol oxidase and/or xylitol oxidase activity, and that has a sequence selected from SEQ ID NO 2, 4, 5, 6, 7, 8, 9, 10, 11, 12, 13, 14, 16, 28, 35, 37, 38 and 40.

In another embodiment, the invention provides a host cell that comprises a polynucleotide that polynucleotide is present in the genome of said host cell or in a vector that autonomously replicates in said host cell, and that encodes a POx polypeptide that has a sequence selected from SEQ ID NO: 2, 4, 5, 6, 7, 8, 9, 10, 11, 12, 13, 14, 16, 28, 35, 37, 38 and 40.

In another embodiment, the invention provides an *S. lividans*, a *B. subtilis* or an *Acidothermus cellulolyticus* host cell host cell that comprises a polynucleotide that encodes a POx polypeptide that has a sequence selected from SEQ ID NO: 2, 4, 5, 6, 7, 8, 9, 10, 11, 12, 13, 14, 16, 28, 35, 37, 38 and 40.

In another embodiment, the invention provides a method for producing a polypeptide having POx activity that includes (a) transforming a host cell with a recombinant expression vector that comprises a polynucleotide sequence that encodes a POx polypeptide having a sequence selected from SEQ ID NO: 2, 4, 5, 6, 7, 8, 9, 10, 11, 12, 13, 14, 16, 28, 35, 37, 38 and 40, (b) growing the transformed host cell under conditions suitable for the expression of said POx polypeptide; and (c) recovering the POx polypeptide.

In another embodiment, the invention provides a method for producing a polypeptide having sorbitol and/or xylitol activity that includes (a) transforming a host cell with a recombinant expression vector that comprises a polynucleotide sequence that encodes a POx polypeptide having a sequence selected from SEQ ID NO: 2, 4, 5, 6, 7, 8, 9, 10, 11, 12, 13, 14, 16, 28, 35, 37, 38 and 40, (b) growing the transformed host cell under conditions suitable for the expression of said POx polypeptide; and (c) recovering the POx polypeptide.

In another embodiment, the invention provides a method for producing a polypeptide having POx activity that includes (a) transforming a *Bacillus*, a *Streptomyces* or an *E. Coli* host cell with a recombinant expression vector that comprises a polynucleotide sequence that encodes a POx polypeptide having a sequence selected from SEQ ID NO: 2, 4, 5, 6, 7, 8, 9, 10, 11, 12, 13, 14, 16, 28, 35, 37, 38 and 40, (b) growing the transformed host cell under conditions suitable for the expression of said POx polypeptide; and (c) recovering the POx polypeptide.

In another embodiment, the invention provides a method for producing a polypeptide having POx activity that includes (a) transforming a host cell with a recombinant expression vector that comprises a polynucleotide sequence that encodes a POx polypeptide having a sequence selected from SEQ ID NO: 2, 4, 5, 6, 7, 8, 9, 10, 11, 12, 13, 14, 16, 28, 35, 37, 38 and 40, (b) growing the transformed host cell under conditions suitable for the expression of said POx polypeptide; and (c) recovering the POx polypeptide, wherein the expression of the polypeptide is extracellular.

In another embodiment, the invention provides a method for producing a polypeptide having POx activity that includes (a) transforming a host cell with a recombinant expression vector that comprises a polynucleotide sequence that encodes a POx polypeptide having a sequence selected from SEQ ID NO: 2, 4, 5, 6, 7, 8, 9, 10, 11, 12, 13, 14, 16, 28, 35, 37, 38 and 40, (b) growing the transformed host cell under conditions suitable for the expression of said POx polypeptide; and (c) recovering the POx polypeptide, wherein the expression of the polypeptide is intracellular.

In another embodiment, the invention provides for a cleaning composition that comprises an effective amount of an isolated POx that has an amino acid sequence that is at least about 70% identical to a POx having a sequence selected from SEQ ID NO:2, 4, 5, 6, 7, 8, 9, 10, 11, 12, 13, and/or 14.

In another embodiment, the invention provides for a detergent composition that comprises an effective amount of an isolated POx that has an amino acid sequence that is at least about 70% identical to a POx having a sequence selected from SEQ ID NO:2, 4, 5, 6, 7, 8, 9, 10, 11, 12, 13, and/or 14.

In another embodiment, the invention provides for a detergent composition that comprises an effective amount of an isolated POx that has an amino acid sequence that is at least about 70% identical to a POx having a sequence selected from SEQ ID NO:2, 4, 5, 6, 7, 8, 9, 10, 11, 12, 13, and/or 14, at least one additional enzyme, and a bleach activator.

In another embodiment, the invention provides for a cleaning composition that comprises an effective amount of an isolated POx that has an amino acid sequence that is at least about 70% identical to a POx having a sequence selected from SEQ ID NO: 2, 4, 5, 6, 7, 8, 9, 10, 11, 12, 13, and/or 14 and least one additional enzyme.

In another embodiment, the invention provides for a cleaning composition that comprises an effective amount of an isolated POx that has an amino acid sequence that is at least about 70% identical to a POx having a sequence selected from SEQ ID NO: 2, 4, 5, 6, 7, 8, 9, 10, 11, 12, 13, and/or 14 and least one additional enzyme that is selected from hemicellulases, peroxidases, proteases, cellulases, xylanases, lipases, phospholipases, esterases, cutinases, pectinases, keratinases, reductases, oxidases, oxidoreductases, perhydrolases, phenoloxidases, lipoxygenases, ligninases, pullulanases, tannases, pentosanases, mannanases, β-glucanases, arabinosidases, hyaluronidases, chondroitinases, laccases, and amylasess, or mixtures thereof.

In another embodiment, the invention provides for a cleaning composition that comprises an effective amount of an isolated POx that has an amino acid sequence that is at least about 70% identical to a POx having a sequence selected from SEQ ID NO:2, 4, 5, 6, 7, 8, 9, 10, 11, 12, 13, and/or 14 and least one additional enzyme that is a perhydrolase.

In another embodiment, the invention provides for a cleaning composition that comprises an effective amount of an isolated POx that has an amino acid sequence that is at least about 70% identical to a POx having a sequence selected from SEQ ID NO:2, 4, 5, 6, 7, 8, 9, 10, 11, 12, 13, and/or 14 and least one additional enzyme that is a glucose oxidase.

In another embodiment, the invention provides for a bleaching composition that comprises an effective amount of an isolated POx that has an amino acid sequence that is at least about 70% identical to a POx having a sequence selected from SEQ ID NO:2, 4, 5, 6, 7, 8, 9, 10, 11, 12, 13, and/or 14 and least one additional enzyme that is a glucose oxidase.

In another embodiment, the invention provides for a method of cleaning that includes contacting a hard surface and/or an article comprising a fabric with a cleaning composition that comprises an effective amount of an isolated POx that has an amino acid sequence that is at least about 70% identical to a POx having a sequence selected from SEQ ID NO:2, 4, 5, 6, 7, 8, 9, 10, 11, 12, 13, and/or 14.

In another embodiment, the invention provides for a method of cleaning that includes contacting a hard surface and/or an article comprising a fabric with a cleaning composition that comprises an effective amount of an isolated POx that has an amino acid sequence that is at least about 70% identical to a POx having a sequence selected from SEQ ID NO:2, 4, 5, 6, 7, 8, 9, 10, 11, 12, 13, and/or 14, and rinsing said surface and/or article after contacting said surface or article with said cleaning composition.

In another embodiment, the invention provides for a method of cleaning that includes contacting a hard surface and/or an article comprising a fabric stained with a substance containing at least one polyol, with a cleaning composition that comprises an effective amount of an isolated POx that has an amino acid sequence that is at least about 70% identical to a POx having a sequence selected from SEQ ID NO:2, 4, 5, 6, 7, 8, 9, 10, 11, 12, 13, and/or 14.

In another embodiment, the invention provides for a method of cleaning that includes contacting a hard surface and/or an article comprising a fabric stained with a substance containing at least one polyol selected from the group of D-sorbitol, D-xylitol, D-mannitol, D-ribitol, myo-inositol, glycerol, 1,3,-propanediol and 1,2-propanediol, with a cleaning composition that comprises an effective amount of an isolated POx that has an amino acid sequence that is at least about 70% identical to a POx having a sequence selected from SEQ ID NO:2, 4, 5, 6, 7, 8, 9, 10, 11, 12, 13, and/or 14.

In another embodiment, the invention provides for a method of cleaning that includes contacting a hard surface and/or an article comprising a fabric, which is soiled with juice, wine and/or tea, with a cleaning composition that comprises an effective amount of an isolated POx that has an amino acid sequence that is at least about 70% identical to a POx having a sequence selected from SEQ ID NO:2, 4, 5, 6, 7, 8, 9, 10, 11, 12, 13, and/or 14.

DESCRIPTION OF THE INVENTION

Figure 1:
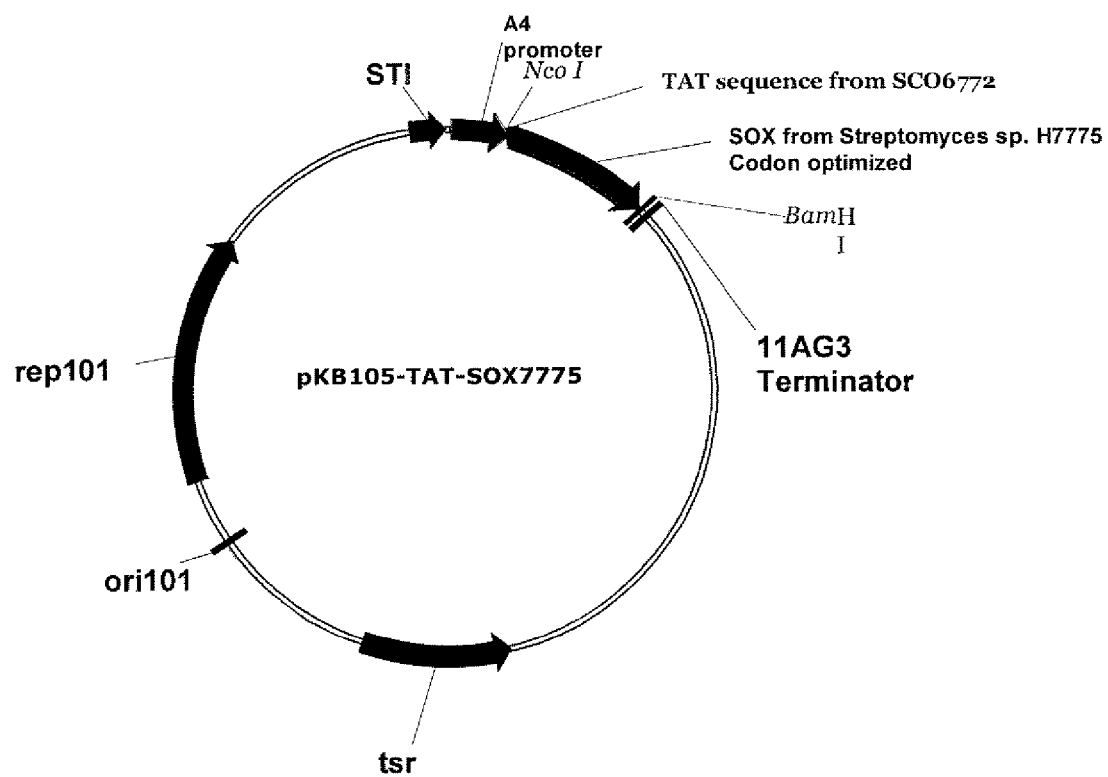
FIG. 1 provides a map of expression plasmid pKB105-TAT-SOx7775 (SEQ ID NO:29).

The present invention provides compositions and methods for producing a polyol oxidase in microorganisms, and the use of polyol oxidases in cleaning compositions. The invention includes cleaning compositions that contain combinations of two or more POx oxidases, and cleaning compositions that contain combinations of two or more POx oxidases and a perhydrolase. In particular, the invention provides methods for expressing polyol oxidases in bacterial hosts for use in detergent applications for cleaning, bleaching and disinfecting.

DEFINITIONS

Unless otherwise indicated, the practice of the present invention involves conventional techniques commonly used in molecular biology, microbiology, protein purification, protein engineering, protein and DNA sequencing, recombinant DNA fields, and industrial enzyme use and development, all of which are within the skill of the art. All patents, patent applications, articles and publications mentioned herein, both supra and infra, are hereby expressly incorporated herein by reference in their entirety.

Furthermore, the headings provided herein are not limitations of the various aspects or embodiments of the invention, which can be had by reference to the specification as a whole. Accordingly, the terms defined immediately below are more fully defined by reference to the specification as a whole. Nonetheless, in order to facilitate understanding of the invention, definitions for a number of terms are provided below.

Unless defined otherwise herein, all technical and scientific terms used herein have the same meaning as commonly understood by one of ordinary skill in the art to which this invention pertains. For example, Singleton and Sainsbury, Dictionary of Microbiology and Molecular Biology, 2d Ed., John Wiley and Sons, NY (1994); and Hale and Margham, The Harper Collins Dictionary of Biology, Harper Perennial, NY (1991) provide those of skill in the art with a general dictionaries of many of the terms used in the invention. Although any methods and materials similar or equivalent to those described herein find use in the practice of the present invention, preferred methods and materials are described herein. Accordingly, the terms defined immediately below are more fully described by reference to the Specification as a whole. Also, as used herein, the singular terms "a," "an," and "the" include the plural reference unless the context clearly indicates otherwise. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

As used herein, the term "oxidase" refers to enzymes that catalyze an oxidation/reduction reaction involving molecular oxygen ($O_2$) as the electron acceptor. In these reactions, oxygen is reduced to water ($H_2O$) or hydrogen peroxide ($H_2O_2$). The oxidases are a subclass of the oxidoreductases.

As used herein, "polyol oxidase", "POx" or "POx polypeptide" refers to enzymes that catalyze the oxidation of various polyols (e.g., sorbitol, xylitol, arabitol, mannitol, ribitol, glycerol, propanediol, and propylene glycol). Polyol oxidase enzymes include oxidoreductase enzyme of the EC1.1.3 class of enzymes that includes sorbitol oxidase, xylitol oxidase, glucose oxidase, hexose oxidase, alcohol oxidase, choline oxidase, mannitol oxidase. As used herein, "polyol" refers to chemical compounds that contain multiple hydroxyl groups.

As used herein, the term "glucose oxidase" ("GOx") refers to the oxidase enzyme (EC 1.1.3.4), a dimeric protein which catalyzes the oxidation of beta-D-glucose into D-glucono-1, 5-lactone, which then hydrolyzes to gluconic acid with concomitant reduction of molecular oxygen to hydrogen peroxide.

As used herein, the term "alcohol oxidase" ("AOx") refers to the oxidase enzyme (EC 1.1.3.13) that converts an alcohol to an aldehyde with concomitant reduction of molecular oxygen to hydrogen peroxide.

As used herein, the term "choline oxidase" ("COx") refers to an oxidase enzyme (EC 1.1.3.17) that catalyzes the four-electron oxidation of choline to glycine betaine, with betaine aldehyde as an intermediate with concomitant reduction of two molecules of molecular oxygen to two molecules of hydrogen peroxide.

As used herein, the term "hexose oxidase" ("HOx") refers to an oxidase enzyme (EC 1.1.3.5) that is capable of the oxidation of mono- and disaccharides to their corresponding lactones, with concomitant reduction of molecular oxygen to hydrogen peroxide. Hexose oxidase is able to oxidize a variety of substrates including D-glucose, D-galactose, maltose, cellobiose, and lactose, etc. It is not intended that the present invention be limited to any particular hexose.

As used herein, "glycerol oxidase" refers to an oxidase enzyme (EC 1.1.3.) that catalyzes the oxidation of glycerol to glyceraldehyde, with concomitant reduction of molecular oxygen to hydrogen peroxide.

As used herein, "sorbitol oxidase" or "SOx" refers to a polyol oxidase enzyme (EC 1.1.3.) that catalyzes the oxidation of a substrate (e.g., D-sorbitol) to D-glucose, with concomitant reduction of molecular oxygen to hydrogen peroxide. The definition further includes oxidase enzymes with a Vmax/Km value which is highest for sorbitol than for xylitol, galactitol, D-mannitol, glycerol and D-arabitol, and no significant activity towards xylose, D-glucose, galactose, mannose and arabinose.

As used herein, the term "xylitol oxidase" ("XOx") refers to an oxidase enzyme that catalyzes the oxidation of xylitol to xylose with concomitant reduction of molecular oxygen to hydrogen peroxide. The definition further includes oxidase enzymes with a Vmax/Km value which is highest for xylitol than for sorbitol, galactitol, D-mannitol, and D-arabitol, and no activity towards xylose, D-glucose, galactose, mannose and arabinose.

In some particularly preferred embodiments, the sorbitol oxidase of the present invention has a higher specific activity, (or $V_{max}/K_{km}$ ratio) on sorbitol substrate, as compared to an alternative substrate under standard assay conditions (e.g, in the in vitro assay provided below) and/or using an in situ in an application media, conducted as known in the art. In some preferred alternative embodiments, the alternative substrate is xylitol.

In some preferred embodiments, the following in vitro assay finds use. An assay mixture containing 266 ul substrate (e.g., sorbitol—Sigma P-5504 or xylitol) (0.055 M, in 0.1 M sodium phosphate buffer, pH 6.3), 12 ul 2,2'-azino-bis(3-ethylbenzothiozoline-6-sulfonic acid) (ABTS)(Sigma A-9941, 5 mg/ml aqueous solution), 12 ul peroxidase (POD) (Sigma P-6782, 0.1 mg/ml in 0.1 M sodium phosphate buffer, pH 6.3) and 10 ul enzyme (SOx or HOx) aqueous solution was prepared. The assay was performed at 25° C. The incubation was started by the addition of glucose to the assay mixture. The absorbance was monitored at 405 nm in an ELISA reader. A standard curve, based on varying concentrations of $H_2O_2$, was used for calculation of enzyme activity. In this assay, 1 polyol unit (POx), such as SOx or XOX units, corresponds to the amount of enzyme, which under the specified conditions results in the conversion of 1 umole of the specified polyol per minute, with resultant generation of 1 umole of hydrogen peroxide ($H_2O_2$).

In some particularly preferred embodiments, the sorbitol oxidase of the present invention has no significant activity on the corresponding sugar product, such as glucose, xylose, galactose, mannose or arabinose, preferably glucose as determined using the assay provided in the Examples.

In some alternative preferred embodiments, the xylitol oxidase of the present invention has a higher specific activity, (or $V_{max}/K_{km}$ ratio) on xylitol substrate, as compared to sorbitol under standard assay conditions (e.g., in the in vitro assay provided herein) and/or in an in situ in an application media, conducted as known in the art.

As used herein, "inhibitors" refers to chemical compounds that can reduce or stop the catalytic activity of an enzyme. In particularly preferred embodiments, the inhibitors reduce or stop the catalytic activity of at least one oxidase. Examples of oxidase inhibitors include acetate, silver salts, halide ions, sec- and tert-alcohols, isocyanate, isothiocyante, glucose analogs, bisulfite, sulfite, thiosulfate, metabisulfite, zinc salts, diethyl dicarbamate, methyl methane sulfonate, acrylonitrile, 2-amino, 2-methyl 1-propanol.

As used herein, "reversible enzyme inhibitor" refers to molecules that bind to an enzyme and decrease its rate of reaction. In some embodiments, reversible enzyme inhibitors are affected by varying the concentration of the enzyme's substrate in relation to the inhibitor. In some embodiments, reversible enzyme inhibitors bind to the enzyme using weak bonds that are similar to those used to bind to substrate. Thus, the reversible inhibitor does not permanently disable the enzyme, as removal of the inhibitor allows the enzyme to bind to and turnover its substrate. In some embodiments, reversible enzyme inhibitors are competitive inhibitors that interact non-covalently with the enzyme, and/or compete with the substrate for the enzyme's active site, and/or have structures that are similar to the substrate, products and/or transition state. In additional embodiments, the reversible inhibitor is a non-competitive enzyme inhibitor that binds at a site present on the enzyme other than the active site, and/or causes conformational changes in the enzyme that decrease, and/or stop catalytic activity. It is not intended that the term be limited to any particular mechanism or type of reversible enzyme inhibitor. It is only necessary that the effects of the enzyme inhibitor be reversible, such that the enzyme will function in the absence of the inhibitor and/or dilutions of the enzyme inhibitor mixture.

As used herein, the term "compatible," means that other composition materials (i.e., other materials in a given composition, in addition to an oxidase of the present invention) do not reduce the enzymatic activity of the oxidase enzyme(s) provided herein to such an extent that the oxidases(s) is/are not effective as desired during normal use situations. Specific composition materials are exemplified in detail hereinafter.

As used herein, "effective amount of enzyme" refers to the quantity of enzyme necessary to achieve the enzymatic activity required in the specific application. Such effective amounts are readily ascertained by one of ordinary skill in the art and are based on many factors, such as the particular enzyme variant used, the application, the specific contents of the composition, and whether a liquid or dry (e.g., granular) composition is required, and the like.

As used herein, "having improved properties" used in connection with "mutant oxidative enzymes," refers to oxidative enzymes with improved performance and/or improved stability with retained performance, relative to the corresponding wild-type oxidase. In some particularly preferred embodiments, the improved properties are selected from the group consisting of improved dishwash performance and improved stability, as well as the combination of improved dishwash performance and improved stability.

As used herein, the phrase "detergent stability" refers to the stability of a detergent composition. In some embodiments, the stability is assessed during the use of the detergent, while in other embodiments, the term refers to the stability of a detergent composition during storage.

The term "improved stability" is used to indicate better stability of oxidases combined with mutant protease(s) in compositions during storage and/or better stability during use (e.g., in the sud). In preferred embodiments, the mutant oxidases combined with mutant protease(s) exhibit improved stability in formulations during storage and/or improved stability during use, which includes stability against oxidizing agents, sequestering agents, autolysis, surfactants and high alkalinity, relative to the corresponding wild-type enzyme.

As used herein, "oxidative stability" refers to the ability of a protein to function under oxidative conditions. In particular, the term refers to the ability of a protein to function in the presence of various concentrations of $H_2O_2$, peracids and other oxidants. Stability under various oxidative conditions can be measured either by standard procedures known to those in the art and/or by the methods described herein. A substantial change in oxidative stability is evidenced by at least about a 5% or greater increase or decrease (in most embodiments, it is preferably an increase) in the half-life of the enzymatic activity, as compared to the enzymatic activity present in the absence of oxidative compounds.

As used herein, "pH stability" refers to the ability of a protein to function at a particular pH. In general, most enzymes have a finite pH range at which they will function. In addition to enzymes that function in mid-range pHs (i.e., around pH 7), there are enzymes that are capable of working under conditions with very high or very low pHs. Stability at various pHs can be measured either by standard procedures known to those in the art and/or by the methods described herein. A substantial change in pH stability is evidenced by at least about 5% or greater increase or decrease (in most embodiments, it is preferably an increase) in the half-life of the enzymatic activity, as compared to the enzymatic activity at the enzyme's optimum pH. However, it is not intended that the present invention be limited to any pH stability level nor pH range.

As used herein, "thermal stability" refers to the ability of a protein to function at a particular temperature. In general, most enzymes have a finite range of temperatures at which they will function. In addition to enzymes that work in mid-range temperatures (e.g., room temperature), there are enzymes that are capable of working in very high or very low temperatures. Thermal stability can be measured either by known procedures or by the methods described herein. A substantial change in thermal stability is evidenced by at least about 5% or greater increase or decrease (in most embodiments, it is preferably an increase) in the half-life of the catalytic activity of a mutant when exposed to given temperature However, it is not intended that the present invention be limited to any temperature stability level nor temperature range.

As used herein, the term "chemical stability" refers to the stability of a protein (e.g., an enzyme) towards chemicals that may adversely affect its activity. In some embodiments, such chemicals include, but are not limited to hydrogen peroxide, peracids, anionic detergents, cationic detergents, non-ionic detergents, chelants, etc. However, it is not intended that the present invention be limited to any particular chemical stability level nor range of chemical stability.

As used herein, the terms "purified" and "isolated" refer to the removal of contaminants from a sample. For example, polyol oxidases are purified by removal of contaminating proteins and other compounds within a solution or preparation that are not polyol oxidases. In some embodiments, recombinant polyol oxidases are expressed in bacterial or fungal host cells and these recombinant polyol oxidases are purified by the removal of other host cell constituents; the percent of recombinant polyol oxidase polypeptides is thereby increased in the sample. In particularly preferred embodiments, the polyol oxidases of the present invention are substantially purified to a level of at least about 99% of the protein component, as determined by SDS-PAGE or other standard methods known in the art.

As used herein, "protein of interest" and "polypeptide of interest" refer to a protein (e.g., an enzyme or "enzyme of interest") which is being analyzed, identified and/or modified. Naturally-occurring, as well as recombinant proteins find use in the present invention.

As used herein, "protein" refers to any composition comprised of amino acids and recognized as a protein by those of skill in the art. The terms "protein," "peptide" and polypeptide are used interchangeably herein. Wherein a peptide is a portion of a protein, those skilled in the art understand the use of the term in context.

The terms "mature form" and "mature region" refer to the final functional portion of the protein. To exemplify, a mature form of the POx of the present invention at least includes the amino acid sequence identical to SEQ ID NO:2, SEQ ID NO:4 and/or SEQ ID NO:6. In this context, the "mature form" is "processed from" a full-length POx, wherein the processing of the full-length carrageenase encompasses the removal of the signal peptide. Thus, for example, the mature form of the POx of SEQ ID NO:2 corresponds to amino acid residues 48 to 467 of SEQ ID NO:16; and the mature form of the POx of SEQ ID NO:6 corresponds to amino acid residues 28 to 480 of SEQ ID NO:37.

A "full-length" protein herein refers to a POx polypeptide that comprises a secretory signal peptide and a mature portion. The fusion POx enzymes of the invention are encoded by chimeric polynucleotides.

The term "chimeric polynucleotide" or "fusion polynucleotide" herein refer to a polynucleotide that comprises at least two separate and distinct regions that may or may not originate from the same gene. For example, a polynucleotide sequence ancoding a signal peptide linked to the polynucleotide that encodes the mature form of the polypeptide would be termed a chimeric polynucleotide. In some embodiments, a chimeric POx polynucleotide encodes a POx fusion polypeptide.

As used herein, the terms "chimeric polypeptide" and "fusion polypeptide" are used interchangeably to refer to a protein that comprises at least two separate and distinct regions that may or may not originate from the same protein. For example, a signal peptide linked to the protein of interest wherein the signal peptide is not normally associated with the protein of interest would be termed a chimeric polypeptide or chimeric protein. A "POx fusion polypeptide" or "POx chimeric polypeptide" herein refers to a polypeptide comprising the sequence of the mature form of the POx enzyme operably linked to a POx signal peptide.

The terms "signal sequence," "signal peptide" and "secretory signal peptide" refer to any sequence of nucleotides and/or amino acids which may participate in the production of the mature or fusion forms of the protein. This definition of signal sequence is a functional one, meant to include all those amino acid sequences encoded by the N-terminal portion of the protein gene, which participate in the effectuation of the secretion of the protein. A "POx signal peptide" herein refers to a signal peptide that is linked to the N-terminus of the mature form of the POx enzyme.

"Naturally-occurring" or "wild-type" refers to a POx protein or a polynucleotide encoding a POx protein having the unmodified amino acid sequence identical to that found in nature. Naturally occurring enzymes include native enzymes, such as those enzymes naturally expressed or found in the particular microorganism. A sequence that is wild-type or naturally-occurring refers to a sequence from which a variant, or a synthetic sequence is derived. The wild-type sequence may encode either a homologous or heterologous protein.

As used herein the term "expression" refers to a process by which a polynucleotide is transcribed and the resulting transcript is translated to yield a polypeptide.

As used herein, functionally and/or structurally similar proteins are considered to be "related proteins." In some embodiments, these proteins are enzymatically active on polyols. In some embodiments, these proteins are derived from a different genus and/or species, including differences between classes of organisms (e.g., a bacterial protein and a fungal protein). In some embodiments, these proteins are derived from a different genus and/or species, including differences between classes of organisms (e.g., a bacterial enzyme and a fungal enzyme). In additional embodiments, related proteins are provided from the same species. Indeed, it is not intended that the present invention be limited to related proteins from any particular source(s). In addition, the term "related proteins" encompasses tertiary structural homologs and primary sequence homologs (e.g., the polyol oxidases of the present invention). In further embodiments, the term encompasses proteins that are immunologically cross-reactive.

As used herein, the term "derivative" refers to a protein which is derived from a protein by addition of one or more amino acids to either or both the C- and N-terminal end(s), substitution of one or more amino acids at one or a number of different sites in the amino acid sequence, and/or deletion of one or more amino acids at either or both ends of the protein or at one or more sites in the amino acid sequence, and/or insertion of one or more amino acids at one or more sites in the amino acid sequence. The preparation of a protein derivative is preferably achieved by modifying a DNA sequence which encodes for the native protein, transformation of that DNA sequence into a suitable host, and expression of the modified DNA sequence to form the derivative protein.

Related (and derivative) proteins comprise "variant proteins." In some preferred embodiments, variant proteins differ from a parent protein and one another by a small number of amino acid residues. In some particularly preferred embodiments, related proteins and particularly variant proteins comprise at least about 65%, 70%, 75%, 80%, 85%, 90%, 95%, 97%, 98%, or 99% amino acid sequence identity. Additionally, a related protein or a variant protein as used herein, refers to a protein that differs from another related protein or a parent protein in the number of prominent regions. For example, in some embodiments, variant proteins have 1, 2, 3, 4, 5, or 10 corresponding prominent regions that differ from the parent protein.

In some embodiments, amino acid and polynucleotide homology is determined using methods known in the art (e.g., the ClustalW algorithm, using standard settings, with EMBOSS::water (local): Gap Open=10.0, Gap extend=0.5, using Blosum 62 (protein), or DNAfull for nucleotide sequences.)

As used herein, the term "variant(s)" as used in context of a polypeptide sequence (e.g., SEQ ID NOS:2, 4, 5, 6, 7, 8, 9, 10, 11, 12, 13, 14, 16, 28, 33, 35, 37, 38, and/or 40 refers to a polypeptide prepared from the original (i.e., parent) polypeptide, or by using the sequence information from the original (i.e., parent) polypeptide, by insertion, deletion and/or substitution of one or more amino acids in the original (i.e., parent) sequence. In some embodiments, at least one insertion, deletion, and/or substitution is made in the original (i.e., parent) sequence, while in other embodiments, preferably less than about 50 amino acids, less than about 40, less than about 30, less than about 20, or less than about 10 amino acids are modified by insertion, deletion and/or substitution of the original (i.e., parent) sequence in order to produce variant polypeptides. In some preferred embodiments, only one amino acid modification (i.e., insertion, deletion or substitution) is made, while in other preferred embodiments two amino acids are modified, and in still further embodiments, three amino acids are modified, and in yet additional embodiments, four amino acids are modified, and in still further embodiments, five amino acids are modified. It is not intended that the variants of the present invention be limited to any specific number nor type of amino acid modifications.

The terms "precursor" or "parent" polypeptide herein refer to the polypeptide that was modified to provide a variant polypeptide.

As used herein, the term "homologue(s)," when used herein in the context of a polypeptide sequence (e.g., SEQ ID NOS:2, 4, 5, 6, 7, 8, 9, 10, 11, 12, 13, 14, 16, 28, 33, 35, 37, 38, and/or 40) refers to a polypeptide which is at least about 70% homologous, more preferably at least about 80% homologous, still more preferably at least about 85% homologous, further more preferably at least about 90% homologous, even more preferably at least about 95%, more preferably about 96%, still more preferably about 97%, even more preferably about 98%, or most preferably about 99% homologous to the polypeptide sequence of interest (e.g., a polyol oxidase provided by the present invention). In some embodiments, homology between two polypeptide sequences is determined using ClustalW alignment algorithm using standard settings, as referred to herein. However, it is not intended that the present invention be limited to any particular method for determining homology.

The term "heterologous" used in this context refers to a sequence which originates from a species or strain other than the species or strain from which the polypeptide, or the parent polypeptide from which the polypeptide is derived (i.e., a variant, homologue or fragment) is naturally found, for example a heterologous signal peptide encoding polynucleotide.

As used herein, the term "fragment(s)," as used herein in the context of a polypeptide sequence (e.g., SEQ ID NOS:2, 4, 5, 6, 7, 8, 9, 10, 11, 12, 13, 14, 16, 28, 33, 35, 37, 38, and/or 40) refers to a polypeptide which consists of only a part of the original (i.e., parent) polypeptide sequence. In some embodiments, fragments comprise at least about 50%, at least about 60%, at least about 70%, at least about 80%, at least about 90%, at least about 95% of the original (i.e., parent) polypeptide sequence.

The variants, homologues and fragments provided by the present invention all retain at least some of the desired enzymatic activity of the parent enzyme, such as at least about 10%, at least about 20%, at least about 30%, at least about 40%, at least about 50%, at least about 60%, at least about 70%, at least about 80% at least about 90%, or all the enzyme activity of the parent enzyme. In some alternative embodiments, the variants and/or homologues have greater enzymatic activity than the original (i.e., parent) enzyme.

It is intended that although preferred enzymes for use in the vectors and methods of the invention are referred to herein by their specific SEQ ID NOS, the present invention encompasses enzymes which are derived from the nucleic acids which encode the corresponding amino acid SEQ ID NOS, when expressed, either in their native host species or a heterologous host species. Thus, the present invention encompasses embodiments in which the enzymes are co- or post-translationally processed.

Several methods are known in the art that are suitable for generating variants of the enzymes of the present invention, including but not limited to site-saturation mutagenesis, scanning mutagenesis, insertional mutagenesis, random mutagenesis, site-directed mutagenesis, and directed-evolution, as well as various other recombinatorial approaches.

Characterization of wild-type and mutant proteins is accomplished via any means suitable and is preferably based on the assessment of properties of interest. For example, pH and/or temperature, as well as detergent and/or oxidative stability is/are determined in some embodiments of the present invention. Indeed, it is contemplated that enzymes having various degrees of stability in one or more of these characteristics (pH, temperature, proteolytic stability, detergent stability, and/or oxidative stability) will find use.

As used herein, "expression vector" refers to a DNA construct containing a DNA sequence that is operably linked to a suitable control sequence capable of effecting the expression of the DNA in a suitable host. Such control sequences include a promoter to effect transcription, an optional operator sequence to control such transcription, a sequence encoding suitable mRNA ribosome binding sites and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. In the present specification, "plasmid," "expression plasmid," and "vector" are often used interchangeably as the plasmid is the most commonly used form of vector at present. However, the invention is intended to include such other forms of expression vectors that serve equivalent functions and which are, or become, known in the art.

In some preferred embodiments, the POx gene is ligated into an appropriate expression plasmid. The cloned POx gene is then used to transform or transfect a host cell in order to express the sorbitol oxidase gene. This plasmid may replicate in hosts in the sense that it contains the well-known elements necessary for plasmid replication or the plasmid may be designed to integrate into the host chromosome. The necessary elements are provided for efficient gene expression (e.g., a promoter operably linked to the gene of interest). In some embodiments, these necessary elements are supplied as the gene's own homologous promoter if it is recognized, (i.e., transcribed, by the host), a transcription terminator (a polyadenylation region for eukaryotic host cells) which is exogenous or is supplied by the endogenous terminator region of the sorbitol oxidase gene. In some embodiments, a selection gene such as an antibiotic resistance gene that enables continuous cultural maintenance of plasmid-infected host cells by growth in antimicrobial-containing media is also included.

As used herein, "corresponding to," refers to a residue at the enumerated position in a protein or peptide, or a residue that is analogous, homologous, or equivalent to an enumerated residue in a protein or peptide.

As used herein, "corresponding region," generally refers to an analogous position along related proteins or a parent protein.

The terms "nucleic acid molecule encoding," "nucleic acid sequence encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "POx polynucleotide" herein refers to the DNA sequence encoding a POx polypeptide.

As used herein, the term "analogous sequence" refers to a sequence within a protein that provides similar function, tertiary structure, and/or conserved residues as the protein of interest (i.e., typically the original protein of interest). For example, in epitope regions that contain an alpha helix or a beta sheet structure, the replacement amino acids in the analogous sequence preferably maintain the same specific structure. The term also refers to nucleotide sequences, as well as amino acid sequences. In some embodiments, analogous sequences are developed such that the replacement amino acids result in a variant enzyme showing a similar or improved function. In some preferred embodiments, the tertiary structure and/or conserved residues of the amino acids in the protein of interest are located at or near the segment or fragment of interest. Thus, where the segment or fragment of interest contains, for example, an alpha-helix or a beta-sheet structure, the replacement amino acids preferably maintain that specific structure.

As used herein, "homologous protein" refers to a protein (e.g., polyol oxidase) that has similar action and/or structure, as a protein of interest (e.g., a polyol oxidase from another source). It is not intended that homologs be necessarily related evolutionarily. Thus, it is intended that the term encompass the same or similar enzyme(s) (i.e., in terms of structure and function) obtained from different species. In some preferred embodiments, it is desirable to identify a homolog that has a quaternary, tertiary and/or primary structure similar to the protein of interest, as replacement for the segment or fragment in the protein of interest with an analogous segment from the homolog will reduce the disruptiveness of the change. In some preferred embodiments, the homologs are selected from SEQ ID NOS:2, 4, 5, 6, 7, 8, 9, 10, 11, 12 and 13, while in other embodiments, the homolog is SEQ ID NO:14.

As used herein, "homologous genes" refers to at least a pair of genes from different species, which genes correspond to each other and which are identical or very similar to each other. The term encompasses genes that are separated by speciation (i.e., the development of new species) (e.g., orthologous genes), as well as genes that have been separated by genetic duplication (e.g., paralogous genes). These genes encode "homologous proteins."

As used herein, "ortholog" and "orthologous genes" refer to genes in different species that have evolved from a common ancestral gene (i.e., a homologous gene) by speciation. Typically, orthologs retain the same function during the course of evolution. Identification of orthologs finds use in the reliable prediction of gene function in newly sequenced genomes.

As used herein, "paralog" and "paralogous genes" refer to genes that are related by duplication within a genome. While orthologs retain the same function through the course of evolution, paralogs evolve new functions, even though some functions are often related to the original one.

As used herein, "wild-type" and "native" proteins are those found in nature. The terms "wild-type sequence," and "wild-type gene" are used interchangeably herein, to refer to a sequence that is native or naturally occurring in a host cell. In some embodiments, the wild-type sequence refers to a sequence of interest (i.e., a sequence that is being analyzed, assessed, modified, etc.) that is the starting point of a protein engineering project. The genes encoding the naturally-occurring protein may be obtained in accord with the general methods known to those skilled in the art. The methods generally comprise synthesizing labeled probes having putative sequences encoding regions of the protein of interest, preparing genomic libraries from organisms expressing the protein, and screening the libraries for the gene of interest by hybridization to the probes. Positively hybridizing clones are then mapped and sequenced.

The term "recombinant DNA molecule" as used herein refers to a DNA molecule that is comprised of segments of DNA joined together by means of molecular biological techniques.

The term "recombinant oligonucleotide" refers to an oligonucleotide created using molecular biological manipulations, including but not limited to, the ligation of two or more oligonucleotide sequences generated by restriction enzyme digestion of a polynucleotide sequence, the synthesis of oligonucleotides (e.g., the synthesis of primers or oligonucleotides) and the like.

The degree of homology between sequences may be determined using any suitable method known in the art (See e.g., Smith and Waterman, Adv. Appl. Math., 2:482 [1981]; Needleman and Wunsch, J. Mol. Biol., 48:443 [1970]; Pearson and Lipman, Proc. Natl. Acad. Sci. USA 85:2444 [1988]; programs such as GAP, BESTFIT, FASTA, and TFASTA in the Wisconsin Genetics Software Package (Genetics Computer Group, Madison, Wis.); and Devereux et al., Nucl. Acid Res., 12:387-395 [1984]).

For example, PILEUP is a useful program to determine sequence homology levels. PILEUP creates a multiple sequence alignment from a group of related sequences using progressive, pairwise alignments. It can also plot a tree showing the clustering relationships used to create the alignment. PILEUP uses a simplification of the progressive alignment method of Feng and Doolittle, (Feng and Doolittle, J. Mol. Evol., 35:351-360 [1987]). The method is similar to that described by Higgins and Sharp (Higgins and Sharp, CABIOS 5:151-153 [1989]). Useful PILEUP parameters including a default gap weight of 3.00, a default gap length weight of 0.10, and weighted end gaps. Another example of a useful algorithm is the BLAST algorithm, described by Altschul et al., (Altschul et al., J. Mol. Biol., 215:403-410, [1990]; and Karlin et al., Proc. Natl. Acad. Sci. USA 90:5873-5787 [1993]). One particularly useful BLAST program is the WU-BLAST-2 program (See, Altschul et al., Meth. Enzymol., 266:460-480 [1996]). parameters "W," "T," and "X" determine the sensitivity and speed of the alignment. The BLAST program uses as defaults a wordlength (W) of 11, the BLOSUM62 scoring matrix (See, Henikoff and Henikoff, Proc. Natl. Acad. Sci. USA 89:10915 [1989]) alignments (B) of 50, expectation (E) of 10, M'5, N'-4, and a comparison of both strands.

As used herein, "percent (%) nucleic acid sequence identity" is defined as the percentage of nucleotide residues in a candidate sequence that is identical with the nucleotide residues of the sequence.

As used herein, the term "hybridization" refers to the process by which a strand of nucleic acid joins with a complementary strand through base pairing, as known in the art.

As used herein, the phrase "hybridization conditions" refers to the conditions under which hybridization reactions are conducted. These conditions are typically classified by degree of "stringency" of the conditions under which hybridization is measured. The degree of stringency can be based, for example, on the melting temperature (Tm) of the nucleic acid binding complex or probe. For example, "maximum stringency" typically occurs at about Tm−5° C. (5° below the Tm of the probe); "high stringency" at about 5-10° below the Tm; "intermediate stringency" at about 10-20° below the Tm of the probe; and "low stringency" at about 20-25° below the Tm. Alternatively, or in addition, hybridization conditions can be based upon the salt or ionic strength conditions of hybridization and/or one or more stringency washes. For example, 6×SSC=very low stringency; 3×SSC=low to medium stringency; 1×SSC=medium stringency; and 0.5× SSC=high stringency. Functionally, maximum stringency conditions may be used to identify nucleic acid sequences having strict identity or near-strict identity with the hybridization probe; while high stringency conditions are used to identify nucleic acid sequences having about 80% or more sequence identity with the probe. For applications requiring high selectivity, it is typically desirable to use relatively stringent conditions to form the hybrids (e.g., relatively low salt and/or high temperature conditions are used).

The phrases "substantially similar and "substantially identical" in the context of at least two nucleic acids or polypeptides typically means that a polynucleotide or polypeptide comprises a sequence that has at least about 40% identity, more preferable at least about 50% identity, yet more preferably at least about 60% identity, preferably at least about 75% identity, more preferably at least about 80% identity, yet more preferably at least about 90%, still more preferably about 95%, most preferably about 97% identity, sometimes as much as about 98% and about 99% sequence identity, compared to the reference (i.e., wild-type) sequence. Sequence identity may be determined using known programs such as BLAST, ALIGN, and CLUSTAL using standard parameters. (See e.g., Altschul, et al., J. Mol. Biol. 215:403-410 [1990]; Henikoff et al., Proc. Natl. Acad. Sci. USA 89:10915 [1989]; Karin et al., Proc. Natl. Acad. Sci. USA 90:5873 [1993]; and Higgins et al., Gene 73:237-244 [1988]). Software for performing BLAST analyses is publicly available through the National Center for Biotechnology Information. Also, databases may be searched using FASTA (Pearson et al., Proc. Natl. Acad. Sci. USA 85:2444-2448 [1988]). One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

As used herein, "equivalent residues" refers to proteins that share particular amino acid residues. For example, equivalent resides may be identified by determining homology at the level of tertiary structure for a protein (e.g., polyol oxidase) whose tertiary structure has been determined by x-ray crystallography. Equivalent residues are defined as those for which the atomic coordinates of two or more of the main chain atoms of a particular amino acid residue of the protein having putative equivalent residues and the protein of interest (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the proteins analyzed. The preferred model is the crystallographic model giving the lowest R factor for experimental diffraction data at the highest resolution available, determined using methods known to those skilled in the art of crystallography and protein characterization/analysis.

As used herein, the terms "hybrid polyol oxidases" and "fusion polyol oxidases" refer to proteins that are engineered from at least two different or "parental" proteins. In preferred embodiments, these parental proteins are homologs of one another. For example, in some embodiments, a preferred hybrid sequence or fusion protein contains the N-terminus of a protein and the C-terminus of a homolog of the protein. In some preferred embodiment, the two terminal ends are combined to correspond to the full-length active protein.

The term "regulatory element" as used herein refers to a genetic element that controls some aspect of the expression of nucleic acid sequences. For example, a promoter is a regulatory element which facilitates the initiation of transcription of an operably linked coding region. Additional regulatory elements include splicing signals, polyadenylation signals and termination signals.

As used herein, "host cells" are generally prokaryotic or eukaryotic hosts which are transformed or transfected with vectors constructed using recombinant DNA techniques known in the art. Transformed host cells are capable of either replicating vectors encoding the protein variants or expressing the desired protein variant. In the case of vectors which encode the pre- or prepro-form of the protein variant, such variants, when expressed, are typically secreted from the host cell into the host cell medium.

The term "introduced" in the context of inserting a nucleic acid sequence into a cell, means transformation, transduction or transfection. Means of transformation include protoplast transformation, calcium chloride precipitation, electroporation, naked DNA and the like as known in the art. (See, Chang and Cohen, Mol. Gen. Genet., 168:111-115 [1979]; Smith et al., Appl. Env. Microbiol., 51:634 [1986]; and the review article by Ferrari et al., in Harwood, *Bacillus*, Plenum Publishing Corporation, pp. 57-72 [1989]).

The term "promoter/enhancer" denotes a segment of DNA which contains sequences capable of providing both promoter and enhancer functions (for example, the long terminal repeats of retroviruses contain both promoter and enhancer functions). The enhancer/promoter may be "endogenous" or "exogenous" or "heterologous." An endogenous enhancer/promoter is one which is naturally linked with a given gene in the genome. An exogenous (heterologous) enhancer/promoter is one which is placed in juxtaposition to a gene by means of genetic manipulation (i.e., molecular biological techniques).

The presence of "splicing signals" on an expression vector often results in higher levels of expression of the recombinant transcript. Splicing signals mediate the removal of introns from the primary RNA transcript and consist of a splice donor and acceptor site (Sambrook et al., Molecular Cloning: A Laboratory Manual, 2nd ed., Cold Spring Harbor Laboratory Press, New York [1989], pp. 16.7-16.8). A commonly used splice donor and acceptor site is the splice junction from the 16S RNA of SV40.

The term "stable transfection" or "stably transfected" refers to the introduction and integration of foreign DNA into the genome of the transfected cell. The term "stable transfectant" refers to a cell which has stably integrated foreign or exogenous DNA into the genomic DNA of the transfected cell.

The terms "selectable marker" or "selectable gene product" as used herein refer to the use of a gene which encodes an enzymatic activity that confers resistance to an antibiotic or drug upon the cell in which the selectable marker is expressed.

As used herein, the terms "amplification" and "gene amplification" refer to a process by which specific DNA sequences are disproportionately replicated such that the amplified gene becomes present in a higher copy number than was initially present in the genome. In some embodiments, selection of cells by growth in the presence of a drug (e.g., an inhibitor of an inhibitable enzyme) results in the amplification of either the endogenous gene encoding the gene product required for growth in the presence of the drug or by amplification of exogenous (i.e., input) sequences encoding this gene product, or both. Selection of cells by growth in the presence of a drug (e.g., an inhibitor of an inhibitable enzyme) may result in the amplification of either the endogenous gene encoding the gene product required for growth in the presence of the drug or by amplification of exogenous (i.e., input) sequences encoding this gene product, or both.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the term "co-amplification" refers to the introduction into a single cell of an amplifiable marker in conjunction with other gene sequences (i.e., comprising one or more non-selectable genes such as those contained within an expression vector) and the application of appropriate selective pressure such that the cell amplifies both the amplifiable marker and the other, non-selectable gene sequences. The amplifiable marker may be physically linked to the other gene sequences or alternatively two separate pieces of DNA, one containing the amplifiable marker and the other containing the non-selectable marker, may be introduced into the same cell.

As used herein, the terms "amplifiable marker," "amplifiable gene," and "amplification vector" refer to a marker, gene or a vector encoding a gene which permits the amplification of that gene under appropriate growth conditions.

As used herein, the term "amplifiable nucleic acid" refers to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of "target" (defined below). In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

"Template specificity" is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (See e.g., Kacian et al., Proc. Natl. Acad. Sci. USA 69:3038 [1972]). Other nucleic acids are not replicated by this amplification enzyme. Similarly, in the case of T7 RNA polymerase, this amplification enzyme has a stringent specificity for its own promoters (See, Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (See, Wu and Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to amplification methods (e.g., the polymerase chain reaction), refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the methods of U.S. Pat. Nos. 4,683,195, 4,683,202, and 4,965,188, hereby incorporated by reference, which include methods for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the terms "restriction endonucleases" and "restriction enzymes" refer to bacterial enzymes, each of which cut double-stranded DNA at or near a specific nucleotide sequence.

"Recovering" a polypeptide from a culture medium refers to collecting the polypeptide in the culture medium into which it was secreted by the host cell. The polypeptide can also be recovered from a lysate prepared from the host cells and further purified. A secreted polypeptide may be recovered from the cell wall fraction prepared according to methods known in the art. One skilled in the art can readily follow known methods for isolating polypeptides and proteins in order to obtain one of the isolated polypeptides or proteins of the present invention. These include, but are not limited to, immunochromatography, HPLC, size-exclusion chromatography, ion-exchange chromatography, and immuno-affinity chromatography. See, e.g., Scopes, Protein Purification: Principles and Practice, Springer-Verlag (1994); Sambrook, et al., in Molecular Cloning: A Laboratory Manual; Ausubel et al., Current Protocols in Molecular Biology. The protein produced by a recombinant host cell comprising a secretion factor of the present invention will be secreted into the culture media.

As used herein, "compositions", "cleaning compositions" and "cleaning formulations" refer to compositions that find use in the removal of undesired compounds from items to be cleaned, such as fabric, dishes, contact lenses, other solid substrates, hair (shampoos), skin (soaps and creams), teeth (mouthwashes, toothpastes) etc. The term encompasses any materials/compounds selected for the particular type of cleaning composition desired and the form of the product (e.g., liquid, gel, granule, or spray composition), as long as the composition is compatible with the oxidase and other enzyme(s) used in the composition, and any reversible enzyme inhibitors in the composition. The specific selection of cleaning composition materials are readily made by considering the surface, item or fabric to be cleaned, and the desired form of the composition for the cleaning conditions during use.

The terms further refer to any composition that is suited for cleaning, bleaching, disinfecting, and/or sterilizing any object and/or surface. It is intended that the terms include, but are not limited to detergent compositions (e.g., liquid and/or solid laundry detergents and fine fabric detergents; hard surface cleaning formulations, such as for glass, wood, ceramic and metal counter tops and windows; carpet cleaners; oven cleaners; fabric fresheners; fabric softeners; and textile and laundry pre-spotters, as well as dish detergents).

Indeed, the term "cleaning composition" as used herein, includes unless otherwise indicated, granular or powder-form all-purpose or heavy-duty washing agents, especially cleaning detergents; liquid, gel or paste-form all-purpose washing agents, especially the so-called heavy-duty liquid (HDL) types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, car or carpet shampoos, bathroom cleaners; hair shampoos and hair-rinses; shower gels and foam baths and metal cleaners; as well as cleaning auxiliaries such as bleach additives and "stain-stick" or pre-treat types.

As used herein, the terms "detergent composition" and "detergent formulation" are used in reference to mixtures which are intended for use in a wash medium for the cleaning of soiled objects. In some preferred embodiments, the term is used in reference to laundering fabrics and/or garments (e.g., "laundry detergents"). In alternative embodiments, the term refers to other detergents, such as those used to clean dishes, cutlery, etc. (e.g., "dishwashing detergents"). It is not intended that the present invention be limited to any particular detergent formulation or composition. Indeed, it is intended that in addition to oxidase, the term encompasses detergents that contain surfactants, transferase(s), hydrolytic enzymes, oxido reductases, perhydrolases builders, bleaching agents, bleach activators, bluing agents and fluorescent dyes, caking inhibitors, masking agents, enzyme activators, enzyme inhibitors, antioxidants, and solubilizers. In some preferred embodiments, the detergent formulations include, but are not limited to those set forth in U.S. patent application Ser. Nos. 10/576,331 and 10/581,014, as well as WO 05/52161 and WO 05/056782 find use in the present invention. However, it is not intended that the present invention be limited to any particular detergent formulation(s), as any suitable detergent formulation finds use in the present invention.

As used herein, "textile materials" is a general term for fibers, yarn intermediates, yarn, fabrics, and products made from fabrics (e.g., garments and other articles).

As used herein, "fabric" encompasses any textile material. Thus, it is intended that the term encompass garments, as well as fabrics, yarns, fibers, non-woven materials, natural materials, synthetic materials, and any other textile material.

As used herein, "dishwashing composition" refers to all forms of compositions for cleaning dishware, including cutlery, including but not limited to granular and liquid forms. It is not intended that the present invention be limited to any particular type or dishware composition. Indeed, the present invention finds use in cleaning dishware (e.g., dishes, including, but not limited to plates, cups, glasses, bowls, etc.) and cutlery (e.g., utensils, including but not limited to spoons, knives, forks, serving utensils, etc.) of any material, including but not limited to ceramics, plastics, metals, china, glass, acrylics, etc. The term "dishware" is used herein in reference to both dishes and cutlery.

As used herein, "wash performance" of an enzyme refers to the contribution of an enzyme to washing that provides additional cleaning performance to the detergent without the addition of the enzyme to the composition. Wash performance is compared under relevant washing conditions.

The term "relevant washing conditions" is used herein to indicate the conditions, particularly washing temperature, time, washing mechanics, sud concentration, type of detergent and water hardness, actually used in households in a detergent market segment.

The term "improved wash performance" is used to indicate that a better end result is obtained in stain removal from items washed (e.g., fabrics or dishware and/or cutlery) under relevant washing conditions, or that less enzyme, on weight basis, is needed to obtain the same end result relative to another enzyme.

The term "retained wash performance" is used to indicate that the wash performance of an enzyme, on weight basis, is at least 80% relative to another enzyme under relevant washing conditions.

Wash performance of enzymes is conveniently measured by their ability to remove certain representative stains under appropriate test conditions. In these test systems, other relevant factors, such as detergent composition, sud concentration, water hardness, washing mechanics, time, pH, and/or temperature, can be controlled in such a way that conditions typical for household application in a certain market segment are imitated.

As used herein, the term "bleaching" refers to the treatment of a material (e.g., fabric, laundry, pulp, etc.) or surface for a sufficient length of time and under appropriate pH and temperature conditions to effect a brightening (i.e., whitening) and/or cleaning of the material. Examples of chemicals suitable for bleaching include but are not limited to $ClO_2$, $H_2O_2$, peracids, $NO_2$, etc.

As used herein, the term "disinfecting" refers to the removal of contaminants from the surfaces, as well as the inhibition or killing of microbes on the surfaces of items. It is not intended that the present invention be limited to any particular surface, item, or contaminant(s) or microbes to be removed.

As used herein, the term "perhydrolase" refers to an enzyme that is capable of catalyzing a reaction that results in the formation of sufficiently high amounts of peracid suitable for applications such as cleaning, bleaching, and disinfecting. In some preferred embodiments, the perhydrolases encompassed by the present invention include the *M. smegmatis* perhydrolase, variants and/or homologs thereof as described in PCT/US05/056782. However, it is not intended that the present invention be limited to this specific *M. smegmatis* perhydrolase, specific variants of this perhydrolase, nor specific homologs of this perhydrolase.

Polyol Oxidases

Polyols, or sugar alcohols, are polyhydric alcohols produced by hydrogenation or fermentation of different carbohydrates. Chemically, polyols are derived from mono- and disaccharides. Most polyols occur naturally in a variety of food products like vegetables, fruits and mushrooms. They are also regularly presented in fermented foods like wine or soy sauces. Polyols are therefore a normal constituent of the human diet. Polyols comprise a variety of sugar alcohols such as sorbitol, galactitol, lactitol, xylitol, and mannitol, or alcohols such as glycerol, propylene glycol and in addition to being constituents of human diet they are also commonly used in in personal care products, food applications, surfactants, vitamins, plastics and in enzyme product formulations. Polyols are converted to their corresponding sugars and peroxide (H2O2) by polyol oxidase enzymes. Thus, polyol oxidases are attractive biobleaching agents for use in detergents, personal care (e.g., toothpastes, cosmetics, etc.), and other products that incorporate polyol-containing enzyme product formulations.

The invention encompasses polyol oxidases that can be derived or isolated from *Streptomyces, Acidothermus, Arthrobacter, Brevibacterium, Frankia, Nocardia, Janibacter, Marinobacter, Burkholderia, Paracoccus, Chromabacterium, Thermobifida, Xanthomonas, Pseudomonas, Corynebacterium* and *Bacillus*. In some embodiments, the invention encompasses polol oxidases of the class E.E.1.1.3. In some preferred embodiments, the invention encompasses polyol oxidases including sorbitol oxidase (SOx), glycerol oxidase (GLOx), xylitol oxidase (XOx), and alditol oxidase (ALOx). In some preferred embodiments, the invention encompasses combining a polyol oxidase e.g. sorbitol oxidase with a second oxidase such as glucose oxidase, hexose oxidase, pyranose oxidase, glucooligosaccharide oxidase.

Sorbitol oxidase ("SOx") is an enzyme that catalyzes conversion of sorbitol to glucose and hydrogen peroxide. Sorbitol oxidases are known and used in various settings, including diagnostic methods (See e.g., Oda and Hiraga, Ann. NY Acad. Sci., 864:454-457 [1998]; and Yamashita et al J. Biosci. Bioengin., 89:350-360 [2000]). Sorbitol (D-glucitol, $C_6H_{14}O_6$, MW 182.2, CAS 50-70-4) is commonly used in personal care products, food applications, surfactants, vitamins, plastics and in enzyme product formulations. In preferred embodiments of the invention, SOx is used in cleaning, bleaching and/or disinfecting compositions.

In some particularly preferred embodiments, the sorbitol oxidase of the present invention has a higher specific activity, (or $V_{max}/K_{km}$ ratio) on sorbitol substrate, as compared to an alternative substrate under standard assay conditions (e.g, in the in vitro assay provided below) and/or using an in situ in an application media, conducted as known in the art. In some preferred alternative embodiments, the alternative substrate is xylitol. In some particularly preferred embodiments, the sorbitol oxidase of the present invention has no significant activity on the corresponding sugar product, such as glucose, xylose, galactose (3.5%), mannose (1%) or arabinose.

In some preferred embodiments, the SOx is an oxidoreductase that uses covalently bound FAD as a cofactor for oxidation of sorbitol to glucose. This enzyme offers a unique opportunity for its potential use as a biobleach agent on its own, as well as used in combination with other oxidases such as carbohydrate oxidases e.g. glucose oxidase and/or hexose oxidase (See e.g., WO 96/39851), pyranose oxidase (See e.g., WO04/100669), glucooligosaccharide oxidase and *M. nivale* carbohydrate oxidase (See e.g., WO99/31990). An advantage of the use of such combinations is due to the fact that SOx converts sorbitol to glucose, which can then be converted to gluconate by glucose oxidase and/or hexose oxidase and/or carbohydrate oxidases (e.g., *Michrodochium nivale* carbohydrate oxidase) and/or glucooligosaccharide oxidase (e.g., *Acremonium strictum* glucooligosaccharide oxidase), and/or pyranose oxidase thus generating two moles of hydrogen peroxide per mole of sorbitol, as illustrated below.

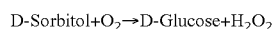

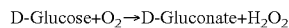

In addition, the preferred sorbitol oxidase provided by the present invention produces glucose, an aldehyde product that can be further oxidized to gluconic acid, a carboxylic acid product using other oxidases such as hexose oxidase, releasing another molecule of hydrogen peroxide from starting substrate sorbitol. Similarly oxidation of polyols such as xylitol, arabitol, mannitol, ribitol, inositol, by sorbitol oxidase, xylitol oxidase, mannitol oxidase with the assistance of atmospheric oxygen with formation of, xylose, arabinose, mannose, ribose, respectively as secondary substrate for further oxidation by other relevant oxidases such as hexose oxidase, xylose oxidase, pyranose oxidase, arabinose oxidase, mannose oxidase, and ribose oxidase is feasible.

Thus, in some embodiments, a polyol oxidase e.g. SOx can be used alone, while in other embodiments, SOx can be used in combination with at least another oxidase that catalyzes the conversion of the product of the SOx reaction. For example, SOx can be used in combination with any one or multiple sugar oxidase enzymes of the class EC1.1.3. For example, SOx can be used in combination with at least one additional sugar oxidase including but not limited to GOx and/or HOx. In other embodiments, SOx can be used in combination with other oxidases that catalyze the conversion of polyol substrates that are not the products of the SOx reaction.

In yet other embodiments, SOx can be used alone, while in other embodiments, SOx can be used in combination with other oxidase enzymes and/or enzymes that convert the $H_2O_2$ product of oxidase reactions to peracid. For example, SOx can be used in combination with a second oxidase e.g. glucose oxidase, and at least one perhydrolase enzyme. Examples of perhydrolase enzymes that can be used in combination with the POx enzymes described herein are described in PCT/05/056782. The following equation provides an example of a coupled system that finds use with the present invention.

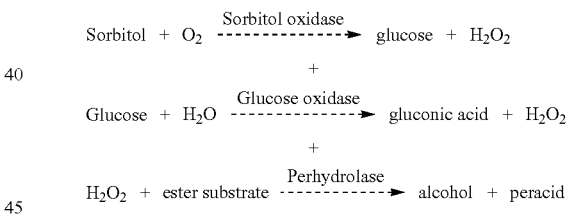

POx enzymes can also be used in combination with bleach activators such as TAED, NOBS etc., which can be activated by $H_2O_2$.

Other POx enzymes that find use in the present invention include xylitol oxidase, glycerol oxidase and alditol oxidase.

Xylitol oxidase ("XOx") is a monomeric oxidase containing one molecule of FAD per molecule of protein, and it can be derived from *Streptomyces* sp. IKD472. The enzyme catalyzes the conversion of xylitol to glucose and H2O2, and can also oxidize D-sorbitol (Yamashita et al., J. Biosci. Bioeng. 89 (2000) 350-360). Thus, the invention encompasses cleaning, disinfecting and/or antimicorbial compositions that comprise XOx. In some embodiments, the compositions of the invention comprise XOx in combination with at least one other sugar oxidase. In other embodiments, compositions of the invention comprise XOx in combination with at least one other sugar oxidase and/or a perhydrolase.

In some embodiments, the present invention encompasses a xylitol oxidase that has a higher specific activity, (or $V_{max}/K_{km}$ ratio) on xylitol substrate, as compared to sorbitol under standard assay conditions (e.g., in the in vitro assay provided herein) and/or in an in situ in an application media, conducted as known in the art. In some preferred alternative embodiments, the alternative substrate is sorbitol.

Glycerol oxidase (GLOX) is an enzyme found in the genera *Penicillium* and *Botrytis* (See e.g., Lin et al Enz. Micro. Technol., 18:383-387 [1996]; and Uwajima et al, Agric. Biol. Chem., 44:399-406 [1989]). This enzyme catalyzes the conversion of glycerol and oxygen to glyceraldehyde and hydrogen peroxide as shown below.

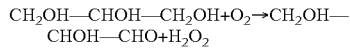

Glycerol (glycerin, $C_3H_8O_3$, MW 92.09, CAS 56-81-5) is a commonly used in enzyme product formulations, soap and detergent formulations, food and beverages, pharmaceuticals and is widely used in cosmetics and personal care applications. Thus, glycerol oxidase provides an attractive biobleaching agent for use in detergents that incorporate these glycerol-containing enzyme product formulations. Thus, the invention encompasses cleaning, disinfecting and/or antimicorbial compositions that comprise GLOx. In some embodiments, the compositions of the invention comprise GLOx in combination with at least one other polyol oxidase. In other embodiments, compositions of the invention comprise GLOx in combination with at least one other polyol oxidase and/or a perhydrolase. In other embodiments, GLOx can be combined with a bleach activator.

In some embodiments, the invention encompasses hexose oxidases ("HOx") (Sullivan, et al., Biochim. Biophys. Acta 309 (1973) 11-22; Bean et al., J. Biol. Chem. 218 (1956); Bean et al., J. Biol. Chem. 236 (1961)), which catalyze the conversion of D-glucose to D-glucono-1,5-lactone and H2O2. Hexose oxidase also utilizes other substrates including D-galactose, D-mannose, maltose, lactose and cellobiose, Thus, the invention encompasses cleaning, disinfecting and/or antimicorbial compositions that comprise HOx. In some embodiments, the compositions of the invention comprise HOx in combination with at least one other polyol oxidase. In other embodiments, compositions of the invention comprise HOx in combination with at least one other polyol oxidase and/or a perhydrolase.

In some embodiments, the compositions of the invention comprise glucose oxidase (GOx), which catalyzes the conversion of glucose to D-glucono-1,5-lactone+H2O2. Thus, GOx can utilize the product of polyol oxidase reactions as a substrate to convert glucose to the corresponding lactone and generate a second molecule of H2O2. Thus, the invention encompasses cleaning, disinfecting and/or antimicorbial compositions that comprise GOx. In some embodiments, the compositions of the invention comprise GOx in combination with at least one other polyol oxidase. In other embodiments, compositions of the invention comprise GOx in combination with at least one other polyol oxidase and/or a perhydrolase. In other embodiments, compositions of the invention comprise GOx in combination with at least one other POx and/or a bleach activator.

As indicated above, key components to peracid production by enzymatic perhydrolysis are enzyme, ester substrate, and hydrogen peroxide. In the present invention, hydrogen peroxide is generated in a coupled enzyme system that includes at least one POx to provide the $H_2O_2$ substrate for the perhydrolase. In some embodiments, the POx oxidase that can be used in cleaning compositions in combination with a perhydrolase can be a polyol oxidases of the class E.E.1.1.3. For example, enzymes (e.g., sorbitol oxidase, glucose oxidase, hexose oxidase, xylitol oxidase, alcohol oxidase, ethylene glycol oxidase, glycerol oxidase, amino acid oxidase, etc.) that can generate hydrogen peroxide also find use with ester substrates in combination perhydrolase enzymes to generate peracids. In some preferred embodiments, the invention encompasses cleaning compositions comprising a combination of a perhydrolase with a sorbitol oxidase (SOx), glycerol oxidase, a glucose oxidase (GOx), a xylitol oxidase (XOx), and/or hexose oxidase (XOx). The invention includes cleaning compositions that include combinations of one or more perhydrolases with one/or more POx enzymes. In some embodiments, the invention cleaning compositions and methods that include a perhydrolase in combination with a sorbitol oxidase and a glucose oxidase. In other embodiments, the invention provides cleaning compositions and methods that encompass a perhydrolase in combination with a sorbitol oxidase and a hexose oxidase. In yet other embodiments, the invention provides cleaning compositions and methods that encompass a perhydrolase. In yet other embodiments, the invention provides compositions and methods that encompass a perhydrolase in combination with xylitol oxidase and a pyranose oxidase. In some embodiments, the compositions of the invention comprise at least one POx enzyme and a bleach activator. The invention also provides for the use of additional sources of $H_2O_2$ that can be used with POx alone or in combination with perhydrolase enzymes. For example, chemical sources of $H_2O_2$ such as percarbonates and perborates, which spontaneously decompose to $H_2O_2$, which are included in some current washing powders find use in the present invention. One advantage of the methods of the present invention is that the generation of acid by a POx (e.g., gluconic acid in the above example) reduces the pH of a basic solution to the pH range in which the peracid is most effective in bleaching (i.e., at or below the pKa). In some preferred embodiments, the ester substrates are selected from one or more of the following acids: formic acid, acetic acid, propionic acid, butyric acid, valeric acid, caproic acid, caprylic acid, nonanoic acid, decanoic acid, dodecanoic acid, myristic acid, palmitic acid, stearic acid, and oleic acid. Importantly, the present invention provides means for effective cleaning, bleaching, and disinfecting over broad pH and temperature ranges. In some embodiments, the compositions of the invention provide effective cleaning, bleaching, and disinfecting at pH between 5.5 and 10.5. The preferred temperatures at which the composition of the invention provide effective cleaning, bleaching, and disinfecting range between 10 and 70° C. Other POx enzymes that find use in the present invention are described in PCT Applications DK2006/000590 and DK2006/000591, which are herein incorporated by reference in their entirety.

The present invention encompasses compositions and methods for expressing polyol oxidases in microorganisms. Polyol oxidases encompassed by the invention include oxidases that can react with a sample containing at least one polyol selected from the group consisting of D-sorbitol, D-mannitol, D-xylitol, and D-arabitol to produce hydrogen peroxide and D-glucose, D-mannose, D-xylose, or D-arabinose, respectively. In some embodiments, the invention encompasses polyol oxidases that are sorbitol oxidases. In other embodiments, the invention encompasses polyol oxidases that are xylitol oxidases.

In some embodiments, the polyol enzymes of the invention have specificity for D-sorbitol and D-xylitol and thus possess both sorbitol oxidase and xylitol oxidase activity. It is understood that the polyol oxidses encompassed by the invention are not limited to oxidases that utilize any one particular substrate but can utilize any one or a combination of substrates including D-sorbitol, D-xylitol, D-mannitol, D-ribitol, myo-inositol, glycerol, 1,3 propanediol and 1,2 propanediol.

The polyol oxidases of the present invention can be isolated from a number of microorganisms including but not limited to *Streptomyces* sp., *Bacillus* sp., *Acidothermus* sp., *Arthobacter* sp., and marine *Acinobacteium* sp. In some preferred embodiments, the *Streptomyces* sp. include *Streptomyces* strain H-7775, *Streptomyces avermitilis*, *Streptomyces coelicolor*, *Streptomyces lividans* and *Streptomyces* species IKD472. In other preferred embodiments, the *Acidothermus* sp. is *Acidothermus cellulolyticus* 11B (Q2E2H5). In some embodiments, the *Arthobacter* sp. is *Arthrobacter* sp. FB24 (Q4NJLO). In some embodiments, the marine *Actinobacterium* is *Actinobacterium* PHSC20C1.

In some embodiments, the invention provides for isolated recombinant polynucleotides that encode a POx. In some embodiments, the recombinant polynucleotides comprise a sequence encoding the mature form of the POx that is a wild-type sequence. In other embodiments, the recombinant polynucleotides comprise a sequence encoding the mature form of the POx that is a variant, homolog or fragment of the wild-type sequence. In some preferred embodiments, the polynucleotide sequence is the wild-type sequence of the SOx of *Streptomyces* H-7775 (e.g. SEQ ID NO:2). In other embodiments, the polynucleotide sequence encoding the POx is the wild-type sequence of the SOx from *Streptomyces lividans* (e.g. SEQ ID NO:4). In some embodiments, the polynucleotides encoding the POx enzymes of the invention are synthetic polynucleoitdes that encode the amino acid sequences of the polyol oxidases derived from the *Streptomyces* sp., *Bacillus* sp., *Acidothermus* sp., *Arthobacter* sp., and marine *Acinobacterium* sp. In some preferred embodiments, the synthetic polynucleotides encode the POx enzymes isolated from *Streptomyces* sp. including *Streptomyces* strain H-7775 (e.g. SEQ ID NO:2), *Streptomyces avermitilis* (e.g. SEQ ID NO:8), *Streptomyces coelicolor* (e.g. SEQ ID NO:9) and *Streptomyces* species IKD472 (e.g. SEQ ID NO:10). In other preferred embodiments, the synthetic polynucleotides encode the POx enzymes isolated from *Acidothermus cellulolyticus* 11B (Q2E2H5; SEQ ID NO:6). In some other embodiments, the synthetic polynucleotides encode the POx enzymes isolated from *Arthrobacter* sp. FB24 (Q4NJLO; SEQ ID NO:12). In yet other embodiments, the synthetic polynucleotides encode the POx enzymes isolated from *Actinobacterium* PHSC20C1 (e.g. SEQ ID NO:13). Other POx sequences that find use in the present invention include but are not limited to polynucleotides that encode the POx of *Acidothermus cellulolyticus* (ZP_01136416: e.g. SEQ ID NO:5), *Streptomyces avermitilis* (NP_823266; e.g. SEQ ID NO:7), *Arthrobacter* sp FB24 (ZP_00411614; e.g. SEQ ID NO:11), and *Streptomyces* sp. IKD472 (Q9KX73; e.g. SEQ ID NO:14). In some embodiments, the POx polynculeotides encode a POx enzyme that has greater SOx activity than XOx activity. In other embodiments, the POx polynucleotides encode a POx enzyme that has greater XOx activity than SOx activity when utilizing the same polyol substrate.

The invention also encompasses polynucleotide sequences, whether wild-type or synthetic that are derived from genes homologous to those of *Streptomyces* H-7775 and/or *Streptomyces lividans*. For example, the invention provides for synthetic polynucleotide sequences e.g. 1, 3, 17, 20, 29, 30, 34, and 44 which comprise sequences encoding polyol oxidases. As indicated above, "homologous genes" are genes that correspond to each other and which are identical or very similar to each other, yet are obtained. from different species. The term encompasses genes that are separated by speciation (i.e., the development of new species) (e.g., orthologous genes), as well as genes that have been separated by genetic duplication (e.g., paralogous genes). Homologous genes encode for homologous proteins.

During the development of the present invention, sorbitol oxidases were isolated from recombinant *Streptomyces lividans* strains expressing the putative sorbitol oxidase gene from *S. lividans* and also the known SOx gene from *Streptomyces* sp. H-7775 (See, Hiraga et al., Biosci. Biotech. Biochem., 61:1699-1704 [1997]). The SOx gene from *S. lividans* was identified based on the sequence derived from the *Streptomyces coelicolor* SCO6147 annotated as a putative xylitol oxidase gene. Two different synthetic genes encoding the *Streptomyces* sp. H-7775 sorbitol oxidase gene were used for intracellular expression in *E. coli* strain BL21(DE3)pLysS and extracellular expression in *S. lividans* g3s3, which is a derivative of the TK23 strain in which the cyc2 gene was deleted (Boremann et al., J. Bacteriol 178:1216-1218 (1996)). The prosthetic group is a covalently bound FAD (1 mol of FAD to 1 mol of SOx). Thus, it is a flavoprotein, with typical absorption maxima at 276, 358, and 455 nm. However, in other embodiments, the enzyme exhibits a second maximum, not at 358 but at 345, indicative of a histidine-flavin linkage. Thus, it is not intended that the present invention be limited to any particular mechanism and/or embodiment. Flavin is functionally involved in oxidation of sorbitol as observed by desired changes in UV-VIS spectra. FAD is very tightly bound with the protein and thus offers a stable enzyme for laundry and personal care (e.g., oral care) applications.

The SOx gene from *Streptomyces* species H-7775 (SEQ ID NO:1) has been described (See, Genbank accession number AB000519). Applicants have identified several homologs of the SOx from S. H-7775 using a BLAST search of the NCBI database. These include but are not limited to a xylitol oxidase from *Streptomyces avermitilis* (BAC69801; Q82LCO; SEQ ID NO:8), a xylitol oxidase from *Streptomyces coelicolor* (Q9ZBU1; SEQ ID NO:9), a xylitol oxidase from *Streptomyces* sp. IKD472 (Q9KX73; SEQ ID NO:10), a putative xylitol oxidase from *Acidothermus cellulolyticus* 11B (Q2E2H5; SEQ ID NO:6), and a FAD-linked oxidase from *Arthrobacter* sp FB24 (ZP00411614; SEQ ID NO:11), a FAD-linked oxidase from *Arthrobacter* sp FB24 (YP_833485; Q4NJLO; SEQ ID NO: 12), a putative xylitol oxidase from marine *Actinobacterium* PHSC20C1 (GenBank Accession no. ZP_01129132) and a xylitol oxidase from *Streptomyces* sp. IKD472 (GenBank Accession no. Q9KX73; SEQ ID NO:14). As discussed above, in some embodiments, the invention encompasses polynucleotide sequences that encode POx that are homologous to that of S. H7775 (SEQ ID NO:2). Thus, the invention encompasses POx enzyme encodes by polynucleotide homologs of SEQ ID NO: 2.

The sorbitol oxidase gene from *Streptomyces* species H-7775 (Genbank accession number AB000519) comprises a 1260 bp open reading frame (ORF) encoding a protein having 420 amino acids with theoretical MW of 45,158 Daltons. The enzyme is stable for 24 hours at 30° C., between pH 7.5-10 with an optimum temperature of 50° C. at pH 7.5. It is also heat stable up to 55° C.

The nearest homolog identified for this enzyme is xylitol oxidase (with 55% homology). SOx is an efficient enzyme for multiple applications, including detergents, fabric care, home care, oral care (e.g., dental whitening, antimicrobial and/or cleaning), personal care, textile processing, food processing and industrial cleaning. In addition, in some embodiments, SOx can catalyze other substrates. Thus, this enzyme uses wide spectrum of substrates, providing flexibility in substrate usage in various applications. It is noted that many of these substrates are present in typical detergent formulations, or can be added to them. The synthetic gene sequence (neutral codons) and the corresponding amino acid sequence of sorbitol oxidase from *Streptomyces* sp. H-7775 are known. These sequences are set forth in SEQ ID NOS:1 and 2, respectively, as shown below. It is noted that the amino acid sequence provided by P97011 (*Streptomyces* sp.) has been reported to be the same as that of *Streptomyces* sp. H-7775.

SEQ ID NO. 1 is the synthetic gene cloned in an *E. coli* expression vector pET24a and expressed in *E. coli* strain BL21(DE3)pLysS.

Thus, in some embodiments, the invention provides for polynculeotides encoding a wild-type SOx derived from *Streptomyces* H-7775 (SEQ ID NO:1)

```
                                                     (SEQ ID NO: 1)
GGTACCCATA TGACCCCTGC TGAAAAAAAC TGGGCCGGCA ATATCACTTT

CGGTGCAAAG AGACTTTGCG TTCCACGTTC TGTCAGAGAG CTGCGCGAAA

CAGTTGCTGC CAGTGGAGCA GTGAGACCTT TGGGAACGCG GCACTCCTTT

AACACTGTCG CTGACACCTC AGGTGATCAT GTTTCTTTGG CCGGTCTCCC

GAGAGTCGTT GACATTGATG TGCCAGGCAG GGCTGTTAGC CTGTCGGCAG

GACTTAGATT CGGTGAGTTT GCTGCCGAAT TGCATGCTCG AGGTCTCGCC

CTGGCAAATC TGGGCTCACT TCCCCACATT TCTGTCGCTG GGGCCGTGGC

AACCGGCACA CATGGAAGTG GAGTGGGTAA CCGTTCCTTG GCCGGTGCTG

TCAGAGCACT GAGCCTCGTT ACTGCTGATG GCGAGACACG CACCCTTAGG

CGTACTGACG AAGATTTTGC CGGGGCTGTC GTGTCTCTGG GCGCATTGGG

AGTTGTGACG TCGCTTGAGT TGGACCTCGT TCCTGCCTTC GAAGTCAGAC

AGTGGGTGTA CGAGGATCTG CCAGAAGCTA CACTTGCCGC CAGATTTGAC

GAGGTTATGT CCGCTGCATA TAGCGTCAGT GTGTTCACGG ATTGGAGACC

GGGTCCTGTT GGACAAGTCT GGCTCAAACA ACGAGTTGGC GACGAAGGGG

CTAGATCAGT ATGCCCGCA GAGTGGCTGG GTGCCAGATT GGCTGATGGA

CCACGTCACC CTGTTCCGGG ATGCCAGCC GGTAATTGTA CTGCACAGCA

AGGCGTTCCG GGCCCTTGGC ATGAAAGACT GCCCCACTTC CGCATGGAAT

TTACCCCATC CAACGGTGAC GAGTTGCAGT CGGAGTATTT TGTCGCTAGG

GCTGATGCCG TTGCCGCCTA CGAAGCTCTT GCACGCCTCC GCGACAGAAT

CGCACCTGTC CTGCAAGTGT CTGAGTTGCG TACAGTCGCT GCCGACGATC

TGTGGCTTTC ACCGGCTCAT GGAAGAGATA GCGTGGCCTT CCACTTTACC

TGGGTTCCAG ACGCTGCCGC AGTCGCTCCT GTGGCCGGTG CAATTGAGGA

AGCTCTCGCC CCCTTTGGCG CAAGACCGCA TGGGGGAAG GTTTTCTCTA

CTGCTCCCGA GGTCCTGCGA ACGTTGTACC CACGCTATGC CGACTTTGAG

GAACTTGTGG GACGTCACGA TCCTGAAGGC ACCTTCAGGA ACGCCTTTCT

CGATCGCTAC TTCCGGCGTT AATAAGGATC CGAGCTC (GENBANK ACCESSION NO. BAA19135; SEQ ID NO: 2)
MTPAEKNWAGNITFGAKRLCVPRSVRELRETVAASGAVRPLGTRHSFNTVADTSGDHV

SLAGLPRVVDIDVPGRAVSLSAGLRFGEFAAELHARGLALANLGSLPHISVAGAVATGTH

GSGVGNRSLAGAVRALSLVTADGETRTLRRTDEDFAGAVVSLGALGVVTSLELDLVPAF

EVRQWVYEDLPEATLAARFDEVMSAAYSVSVFTDWRPGPVGQVWLKQRVGDEGARSV

MPAEWLGARLADGPRHPVPGMPAGNCTAQQGVPGPWHERLPHFRMEFTPSNGDELQ

SEYFVARADAVAAYEALARLRDRIAPVLQVSELRTVAADDLWLSPAHGRDSVAFHFTWV

PDAAAVAPVAGAIEEALAPFGARPHWGKVFSTAPEVLRTLYPRYADFEELVGRHDPEGT

FR NAFLDRYFRR
```

The nucleic and amino acid sequences of the putative sorbitol oxidases in *Streptomyces lividans* and *Streptomyces coelicolor* are provided below (SEQ ID NOS:3 and 4, respectively). The addition of the NcoI cloning site at the start methionine resulted in amino acid change from serine to glycine of the second amino acid residue at the N-terminus. This is the gene cloned and expressed as an intracellular protein in *Streptomyces lividans* g3s3 showing both sorbitol and xylitol oxidase activities, as described herein.

(SEQ ID NO: 3)
```
GCCATGGGCG ACATCACGGT CACCAACTGG GCCGGCAACA
TCACGTACAC GGCGAAGGAA CTGCTGCGGC CGCACTCCCT
GGACGCGCTG CGGGCCCTGG TGGCGGACAG CGCCAGGGTG
CGGGTGCTGG GCAGCGGGCA CTCCTTCAAC GAGATCGCCG
AGCCGGGCGA CGGGGGTGTC CTGCTGTCGC TGGCGGGCCT
GCCGTCCGTG GTGGACGTGG ACACGGCGGC CCGTACGGTG
CGGGTCGGCG GCGGTGTGCG GTACGCGGAG CTGGCCCGGG
TGGTGCACGC GCGGGGCCTG GCGCTGCCGA ACATGGCCTC
GCTGCCGCAC ATCTCGGTCG CCGGGTCGGT GGCCACCGGC
ACCCACGGTT CGGGGGTGGG CAACGGTTCG CTGGCCTCGG
TGGTGCGCGA GGTGGAGCTG GTCACCGCGG ACGGTTCGAC
CGTGGTGATC GCGCGGGGCG ACGAGCGGTT CGGCGGGGCG
GTGACCTCGC TCGGCGCGCT GGGCGTGGTG ACGTCGCTCA
CACTCGACCT GGAGCCGGCG TACGAGATGG AACAGCACGT
CTTCACCGAG CTGCCGCTGG CCGGGTTGGA CCCGGCGACG
TTCGAGACGG TGATGGCGGC GGCGTACAGC GTGAGTCTGT
TCACCGACTG GCGGGCGCCC GGTTTCCGGC AGGTGTGGCT
GAAGCGGCGC ACCGACCGGC CGCTGGACGG TTTCCCGTAC
GCGGCCCCGG CCGCCGAGAA GATGCATCCG GTGCCGGGCA
TGCCCGCGGT GAACTGCACG GAGCAGTTCG GGGTGCCGGG
GCCCTGGCAC GAGCGGCTGC CGCACTTCCG CGCGGAGTTC
ACGCCCAGCA GCGGTGCCGA GTTGCAGTCG GAGTACCTGA
TGCCCCGGGA GCACGCCCTG GCCGCCCTGC ACGCGATGGA
CGCGATACGG GAGACGCTCG CGCCGGTGCT CCAGACCTGC
GAGATCCGCA CGGTCGCCGC CGACGCGCAG TGGCTGAGCC
CGGCGTACGG GCGGGACACC GTGGCCGCGC ACTTCACCTG
GGTCGAGGAC ACGGCGGCGG TGCTGCCGGT GGTGCGGCGG
CTGGAGGAGG CGCTCGTCCC CTTCGCGGCC CGTCCGCACT
GGGGGAAGGT GTTCACCGTC CCGGCGGGCG AGCTGCGTGC
GCTGTACCCG CGGCTGGCCG ACTTCGGGGC GCTGGCCGGG
GCGCTGGACC CGGCGGGGAA GTTCACCAAC GCGTTCGTGC
GCGGGGTGCT CGCGGGCTGA GGATCCAT
```

(SEQ ID NO: 4)
```
MGDITVTNWA GNITYTAKEL LRPHSLDALR ALVADSARVR
VLGSGHSFNE IAEPGDGGVL LSLAGLPSVV DVDTAARTVR
VGGGVRYAEL ARVVHARGLA LPNMASLPHI SVAGSVATGT
HGSGVGNGSL ASVVREVELV TADGSTVVIA RGDERFGGAV
TSLGALGVVT SLTLDLEPAY EMEQHVFTEL PLAGLDPATF
ETVMAAAYSV SLFTDWRAPG FRQVWLKRRT DRPLDGFPYA
APAAEKMHPV PGMPAVNCTE QFGVPGPWHE RLPHFRAEFT
PSSGAELQSE YLMPREHALA ALHAMDAIRE TLAPVLQTCE
IRTVAADAQW LSPAYGRDTV AAHFTWVEDT AAVLPVVRRL
EEALVPFAAR PHWGKVFTVP AGELRALYPR LADFGALAGA
LDPAGKFTNA FVRGVLAG
```

The sequences of other sorbitol oxidases that are homologs of SEQ ID NO:2 or 4 are encompassed by the invention and include those set forth below. It is understood that any homolog of the SOx of SEQ ID NOs: 2 or 4 that retains sorbitol and/or xylitol oxidase activity is encompassed by the invention.

*Acidothermus cellulolyticus* (ZP_01136416)

(SEQ ID NO: 5)
```
MDGGKRCRDG TPQPPAPSEQ VTPSAAASLR AAYDVEVSAP RLRNWAGNIA
FRPRRYVQPRDLDELVEIIRVSDQVRVLGTGHSFNPIADTTGTLISLDHLPREVRVMPGR
TAVSAGTRYGDLAFPLHEAG WALANVGSLP HISIAGACAT ATHGSGDRNG
CLATAVAGMTGVDGTCRVFHLTAESPEFPGAVVHLGALGAVTEIELVTEPTFTVRQWVY
EDAPLDNVFADLDDVTSAAYSVSIFTTWDPPTARQIWLKERVAAGRPDPPA
RRWGGRLAER DHNPVPGMPP ENCTPQLGRIGPWHERLPHF RLDVTPSAGD
ELQSEYFVPRAAAVEAYRALRHIGSRIAPVLQISEIRTVAADELWLSPAYHRPSVAFHFT
WIADEEAVRPVVSEVERALAPLQPRPHWGKLFTMDPAVVRAAYPRFDDFV
ALAERYDPEG KFQNDFLRRF FAG
```

*Acidothermus cellulolyticus* (11B Q2E2H5)

(SEQ ID NO: 6)
```
MDGGKRCRDG TPQPPAPSEQ VTPSAAASLR AAYDVEVSAP RLRNWAGNIA
FRPRRYVQPR DLDELVEIIR VSDQVRVLGT GHSFNPIADT TGTLISLDHL
PREVRVMPGR TAVSAGTRYG DLAFPLHEAG WALANVGSLP HISIAGACAT
```

-continued

```
ATHGSGDRNG CLATAVAGMT GVDGTCRVFH LTAESPEFPG AVVHLGALGA

VTEIELVTEP TFTVRQWVYE DAPLDNVFAD LDDVTSAAYS VSIFTTWDPP

TARQIWLKER VAAGRPDPPA RRWGGRLAER DHNPVPGMPP ENCTPQLGRI

GPWHERLPHF RLDVTPSAGD ELQSEYFVPR AAAVEAYRAL RHIGSRIAPV

LQISEIRTVA ADELWLSPAY HRPSVAFHFT WIADEEAVRP VVSEVERALA

PLQPRPHWGK LFTMDPAVVR AAYPRFDDFV ALAERYDPEG KFQNDFLRRF FAG
```

*Streptomyces avermitilis* (NP_823266)
(SEQ ID NO: 7)

```
MTDAGTALTN WAGNITYSAK ELHRPQSLDA LRALVADSAK VRVLGSGHSF

NEIAEPGADGVLLSLTALPP SVEVDTAART VRVAGGVRYA ELARVVHGHG

LALPNMASLP HISVAGSVATGTHGSGVTNG SLASAVREVE LVTADGSAVR

IGRGDDRFDG AVTALGALGV VTALTLDLEPDYRVAQQVFT ELPLAGLDFD

AVAASAYSVS LFTGWRTSGF AQVWLKRRTD RPSADFPWAAPATEAMHPVP

GMPAVNCTQQ FGVPGPWHER LPHFRAEFTP SSGAELQSEY LLPRPYALDA

LHALDAVRET VAPVLQICEV RTVAADAQWL SPAYGRDTVA LHFTWVEDLA

AVLPVVRRVEEALDPFDPRP HWGKVFAVPA RVLRGRYPRL GDFRALVDSL

DPGGKFTNAF VREVLGSGDRPS
```

*Streptomyces avermitilis* (Q82LCO)
(SEQ ID NO: 8)

```
MTDAGTALTN WAGNITYSAK ELHRPQSLDA LRALVADSAK VRVLGSGHSF

NEIAEPGADG VLLSLTALPP SVEVDTAART VRVAGGVRYA ELARVVHGHG

LALPNMASLP HISVAGSVATGTHGSGVTNG SLASAVREVE LVTADGSAVR

IGRGDDRFDG AVTALGALGV VTALTLDLEP DYRVAQQVFT ELPLAGLDFD

AVAASAYSVS LFTGWRTSGF AQVWLKRRTD RPSADFPWAA PATEAMHPVP

GMPAVNCTQQ FGVPGPWHER LPHFRAEFTP SSGAELQSEY LLPRPYALDA

LHALDAVRET VAPVLQICEV RTVAADAQWL SPAYGRDTVA LHFTWVEDLA

AVLPVVRRVE EALDPFDPRP HWGKVFAVPA RVLRGRYPRL GDFRALVDSL

DPGGKFTNAF VREVLGSGDR PS
```

*Streptomyces coelicolor* (Q9ZBU1)
(SEQ ID NO: 9)

```
MSDITVTNWA GNITYTAKEL LRPHSLDALR ALVADSARVR VLGSGHSFNE

IAEPGDGGVLLSLAGLPSVV DVDTAARTVR VGGGVRYAEL ARVVHARGLA

LPNMASLPHI SVAGSVATGTHGSGVGNGSL ASVVREVELV TADGSTVVIA

RGDERFGGAV TSLGALGVVT SLTLDLEPAYEMEQHVFTEL PLAGLDPATF

ETVMAAAYSV SLFTDWRAPG FRQVWLKRRT DRPLDGFPYAAPAAEKMHPV

PGMPAVNCTE QFGVPGPWHE RLPHFRAEFT PSSGAELQSE

YLMPREHALAALHAMDAIRE TLAPVLQTCE IRTVAADAQW LSPAYGRDTV

AAHFTWVEDT AAVLPVVRRLEEALVPFAAR PHWGKVFTVP AGELRALYPR

LADFGALAGA LDPAGKFTNA FVRGVLAG
```

*Streptomyces* sp. IKD472/FERM P-14339 (Q9KX73)
(SEQ ID NO: 10)

```
MSTAVTNWAG NITYTAKEVH RPATAEELAD VVARSAWGAC AGAAGHSFNE

IADPGPDGVLLRLDALPAETDVDTTARTVR VRGGGVRYAELARVVHAHGLALPNMASLPH

ISVAGSVATGTHGSGVTNGPLAAPVREVELVTADGSQVRIAPGERRFGGAVTSLGALGV
```

-continued

```
VTALTLDLEPAFEVGQHLFTELPLRGLDFETVAAAGYSVSLFTDWREPGFRQVWLKRRT

DQELPDFPWARPATVALHPVPGMPAENCTQQFGVPGPWHERLP HFRAEFTPSS

GAELQSEYLL PRAHALDALDAVDRIRDTVA PVLQTCEVRT VAPDEQWLGP

SHGRDTVALH FTWVKDTEAV LPVVRRLEEALDAFDPRPHW GKVFTTSAAA

LRARYPRLAD FRALARELDP SGKFTNTFLR DLLDG
```

Arthrobacter sp. FB24 (ZP_00411614)
(SEQ ID NO: 11)
```
MRTVSELPGL SGSTGAGSSA PELNWAGNYR YTAASIHRPR

TLEEVQEVVAGASKIRALGSRHSFNAIADS PGSLVSLEDL DPGIRIDAAT

RTVTVSGGTR YGTLAEQLES AGFALSNLASLPHISVAGAI ATATHGSGDA

NGNLATSVAA LELVAADGTV HRLNRGSSPG FDGAVVGLGALGVVTKVTLD

IEPTFTVRQD VFEALPWDTV LGNFDAVTSS AYSVSLFTDW SGDDVAQAWL

KSRLSGSAAS SDAGSTLAGE AFAAGTFFGG TRAGVARHPL PGVSAENCTE

QLGVPGSWSERLAHFRMAFT PSSGEELQSE FFVRREHAVA AIGELRALSD

RITPLLLVSE IRTVAADKLWLSTAYGQDSV GFHFTWKQRQ DEVEKVLPVM

EEALAPFNAR PHWGKLFHAG ADAVAELYPRFSDFKDLAER MDPEQKFRNE

FLARKVFGN
```

Arthrobacter sp. FB 24
(Q4NJL0; GenBank Accession no. YP_833485)
(SEQ ID NO: 12)
```
MRTVSELPGL SGSTGAGSSA PELNWAGNYR YTAASIHRPR TLEEVQEVVA

GASKIRALGS RHSFNAIADS PGSLVSLEDL DPGIRIDAAT RTVTVSGGTR

YGTLAEQLES AGFALSNLAS LPHISVAGAI ATATHGSGDA NGNLATSVAA

LELVAADGTV HRLNRGSSPG FDGAVVGLGA LGVVTKVTLD IEPTFTVRQD

VFEALPWDTV LGNFDAVTSS AYSVSLFTDW SGDDVAQAWL KSRLSGSAAS

SDAGSTLAGE AFAAGTFFGG TRAGVARHPL PGVSAENCTE QLGVPGSWSE

RLAHFRMAFT PSSGEELQSE FFVRREHAVA AIGELRALSD RITPLLLVSE

IRTVAADKLW LSTAYGQDSV GFHFTWKQRQ DEVEKVLPVM EEALAPFNAR

PHWGKLFHAG ADAVAELYPR FSDFKDLAER MDPEQKFRNE FLARKVFGN
```

Marine Actinobacterium PHSC20C1 (ZP_01129132)
(SEQ ID NO: 13)
```
MLTNQTNWAG NLTYNAKAIM QPTNVDELQE LVARLPRVRA LGTRHSFTDI

ADTPGTLMSLANMPPNIHID TTAMTASVTG GTSYGLLMSE LQSNGFALHN

TGSLPHISVA GATATATHGSGDGNGILSTA IAALDVVTAD GSLVTVDRAS

DHLPALAVGL GAFGVIARVT LDIEPTYRVRQDVYRFAPWE TVLEQLDDIM

ASAYSVSLLA DFGSPTVAQI WLKTRLGVGD DPEVAPTLFGGIWYDDSDEL

APQNVNQRAS IPGPWSERMP HFRLDGEPSN GGDELQSEYY

VRREHGVQALEALRGLGAQI SPHLLISEIR TAAADSLWMS PAYGQDVLCI

GFTWAKHPAE VTALLPEIEATLAPFAPRQH WGKLFSFSRD IIAERFPRVA

DFTELRDQYD PQRKFWNPFL ERTLGAP
```

In additional embodiments, xylitol oxidases find use in the present invention. The following sequence is a xylitol oxidase.

```
Streptomyces sp. IKD472 (Q9KX73)
                                          (SEQ ID NO: 14)
MSTAVTNWAG NITYTAKEVH RPATAEELAD VVARSAWGAC

AGAAGHSFNE IADPGPDGVL LRLDALPAET DVDTTARTVR

VGGGVRYAEL ARVVHAHGLA LPNMASLPHI SVAGSVATGT

HGSGVTNGPL AAPVREVELV TADGSQVRIA PGERRFGGAV

TSLGALGVVT ALTLDLEPAF EVGQHLFTEL PLRGLDFETV

AAAGYSVSLF TDWREPGFRQ VWLKRRTDQE LPDFPWARPA

TVALHPVPGM PAENCTQQFG VPGPWHERLP HFRAEFTPSS

GAELQSEYLL PRAHALDALD AVDRIRDTVA PVLQTCEVRT

VAPDEQWLGP SHGRDTVALH FTWVKDTEAV LPVVRRLEEA

LDAFDPRPHW GKVFTTSAAA LRARYPRLAD FRALARELDP

SGKFTNTFLR DLLDG
```

In some embodiments, the POx enzymes of the invention are encoded by chimeric polynucloetides that comprise a polynucleotide that encodes the mature form of the POx enzyme that is operably linked to a polynucleotide that encodes a signal peptide. In some embodiments, the chimeric polynucleotide is a synthetic chimeric polynucleotide. In other embodiments, the chimeric polynucleotide comprises a wild-type sequence that encodes the signal peptide and a synthetic sequence that encodes the mature form of the POx enzyme.

In prokaryotes two pathways for protein translocation across the cytoplasmic membrane have been recognized. In most bacteria the general secretory (Sec) pathway is the best-characterized route for protein export. Proteins exported by this pathway are translocated across the membrane in an unfolded state through a membrane-embedded translocon to which they are targeted by cleavable N-terminal signal peptides (Mori et al., (2001) *Trends in Microbiology* 9:494-500). More recently a second general export pathway has been described, which is designated the twin-arginine translocation (Tat) pathway and reference is made to US 2002/0110860; WO 03/079007; Berks, B. C. (1996) *Mol. Microbiol.* 22:393-404 and Tjalsma et al., (2000) *Microbiol. & Molecul. Bio. Reviews* 64:515-547.

The choice of signal sequence largely depends on the host cell used. As noted above, in certain embodiments, a *Streptomyces* and/or a *Bacillus* host cell is employed, the signal sequence may be any sequence of amino acids that is capable of directing the fusion protein into the TAT or SEC pathway of the *Streptomyces* and/or *Bacillus* host cell.

In some embodiments, signal sequences that may be employed include the signal sequences of proteins that are secreted from wild-type *Bacillus* cells. Such signal sequences include the signal sequences encoded by α-amylase, protease, (e.g., aprE or subtilisin E), or β-lactamase genes. Exemplary signal sequences include, but are not limited to, the signal sequences encoded by an α-amylase gene, an subtilisin gene, a β-lactamase gene, a neutral protease gene (e.g., nprT, nprS, nprM), or a prsA gene from any suitable *Bacillus* species, including, but not limited to *B. stearothermophilus, B. licheniformis, B. lentus, B. subtilis,* and *B. amyloliquefaciens*. In some embodiments, the signal sequence is encoded by the aprE gene of *B. subtilis* (See e.g., Appl. Microbiol. Biotechnol., 62:369-73 [2003]). Further signal peptides find use in the present invention (See e.g., Simonen and Palva, Micro. Rev., 57:109-137 [1993]; etc.). A preferred signal peptide encompassed by the invention is the signal peptide of the *Bacillus circulans* cyclomaltodextrin glucanotransferase (cgt) precursor (Accession no. P43379; SEQ ID NO:36).

In other embodiments, the signal sequence that may be employed includes is a signal sequences of a protein that is secreted from the wild-type *Streptomyces* host cells. Such signal sequences include the signal sequence encoded by the *S. coelicolor* SCO6772 gene (SEQ ID NO:15), the signal sequence encoded by the *S. coelicolor* celA gene (EMBL accession no. AL939132.1; SEQ ID NO: 27); the signal sequence encoded by the *S. coelicolor* secreted endoglucanase gene SCO7363 (SEQ ID NO:31), or the signal sequence encoded by the *S. coelicolor* possible secreted protein gene SCO0624 (SEQ ID NO: 39). Other signal peptides encoded by the *Streptomyces* sp. genes are described in WO2007/071996 and in Widdick et al. (Science 103:17927-17932 (2006).

In some embodiments, the POx polynucleotides encode mature POx polypeptides and/or POx fusion polypepitdes that share at least about 65% amino acid sequence identity, preferably at least about 70% amino acid sequence identity, more preferably at least about 75% amino acid sequence identity, still more preferably at least about 80% amino acid sequence identity, more preferably at least about 85% amino acid sequence identity, even more preferably at least about 90% amino acid sequence identity, more preferably at least about 92% amino acid sequence identity, yet more preferably at least about 95% amino acid sequence identity, more preferably at least about 97% amino acid sequence identity, still more preferably at least about 98% amino acid sequence identity, and most preferably up to about 99% amino acid sequence identity with the amino acid sequence of the precursor POx protein and have comparable or enhanced production activity, as compared to the precursor polypeptide.

As will be understood by the skilled artisan, due to the degeneracy of the genetic code, a variety of POx polynucleotides encode fusion and mature POx proteins. In some other embodiments of the present invention, polynucleotides comprising a nucleotide sequence having at least about 70% sequence identity, at least about 75% sequence identity, at least about 80% sequence identity, at least about 85% sequence identity, at least about 90% sequence identity, at least about 92% sequence identity, at least about 95% sequence identity, at least about 97% sequence identity, at least about 98% sequence identity and at least about 99% sequence identity to the polynucleotide sequence of SEQ ID NOS:2, 4, 5, 6, 7, 8, 9, 10, 11, 12, 13, 14, 16, 28, 33, 35, 37, 38, and/or 40, are provided.

In some embodiments, the percent identity shared by polynucleotide sequences is determined by direct comparison of the sequence information between the molecules by aligning the sequences and determining the identity by methods known in the art. In some embodiments, the percent identity (e.g., amino acid sequence, nucleic acid sequence, and/or gene sequence) is determined by a direct comparison of the sequence information between two molecules by aligning the sequences, counting the exact number of matches between the two aligned sequences, dividing by the length of the shorter sequence, and multiplying the result by 100. Readily available computer programs find use in these analyses including those described above. Programs for determining nucleotide sequence identity are available in the Wisconsin Sequence Analysis Package, Version 8 (Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above.

An example of an algorithm that is suitable for determining sequence similarity is the BLAST algorithm, which is described in Altschul, et al., J. Mol. Biol., 215:403-410 (1990). Software for performing BLAST analyses is publicly available through the National Center for Biotechnology Information. This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a wordlength (W) of 11, the BLOSUM62 scoring matrix (See, Henikoff & Henikoff, *Proc. Natl. Acad. Sci. USA* 89:10915 (1989)) alignments (B) of 50, expectation (E) of 10, M'5, N'-4, and a comparison of both strands.

The BLAST algorithm then performs a statistical analysis of the similarity between two sequences (See e.g., Karlin and Altschul, Proc. Nat'l. Acad. Sci. USA 90:5873-5787 [1993]). One measure of similarity provided by the BLAST algorithm is the smallest sum probability (P(N)), which provides an indication of the probability by which a match between two nucleotide or amino acid sequences would occur by chance. For example, a nucleic acid is considered similar to a serine protease nucleic acid of this invention if the smallest sum probability in a comparison of the test nucleic acid to a serine protease nucleic acid is less than about 0.1, more preferably less than about 0.01, and most preferably less than about 0.001. Where the test nucleic acid encodes a serine protease polypeptide, it is considered similar to a specified serine protease nucleic acid if the comparison results in a smallest sum probability of less than about 0.5, and more preferably less than about 0.2.

In some embodiments of the present invention, sequences were analyzed by BLAST and protein translation sequence tools. In some experiments, the preferred version was BLAST (Basic BLAST version 2.0). The program chosen was "BlastX", and the database chosen was "nr." Standard/default parameter values were employed.

Several methods are known in the art that are suitable for generating variant polynucleotide sequences of the POx enzymes of the present invention, include but are not limited to site-saturation mutagenesis, scanning mutagenesis, insertional mutagenesis, deletion mutagenesis, random mutagenesis, site-directed mutagenesis, and directed-evolution, as well as various other recombinatorial approaches.

This invention further provides expression vectors comprising at least a fragment of the polynucleotides set forth above and host cells or organisms transformed with these expression vectors. Useful vectors include plasmids, cosmids, lambda phage derivatives, phagemids, and the like, that are well known in the art. Accordingly, the invention also provides a vector including a polynucleotide of the invention and a host cell containing the polynucleotide. In general, the vector contains an origin of replication functional in at least one organism, convenient restriction endonuclease sites, and a selectable marker for the host cell.

Preferably, a polynucleotide in a vector is operably linked to a control sequence that is capable of providing for the expression of the coding sequence by the host cell, i.e. the vector is an expression vector. The control sequences may be modified, for example, by the addition of further transcriptional regulatory elements to make the level of transcription directed by the control sequences more responsive to transcriptional modulators. The control sequences may in particular comprise promoters.

In some embodiments, in the vector, the nucleic acid sequence encoding for the POx signal peptide or the POx signal peptide fusion polypeptide is operably combined with a suitable promoter sequence. The promoter can be any DNA sequence having transcription activity in the host organism of choice and can be derived from genes that are homologous or heterologous to the host organism. Examples of suitable promoters for directing the transcription of the modified nucleotide sequence, such as modified enzyme nucleic acids, in a bacterial host include the promoter of the *Streptomyces coelicolor* agarase gene dagA promoters, GI and A4 promoters, the promoters of the *Bacillus licheniformis* alpha-amylase gene (amyL), the aprE promoter of *Bacillus subtilis*, the promoters of the *Bacillus stearothermophilus* maltogenic amylase gene (amyM, the promoters of the *Bacillus amyloliquefaciens* alpha-amylase gene (amyQ), the promoters of the *Bacillus subtilis* xylA and xylB genes and a promoter derived from a *Lactococcus* sp.-derived promoter including the P170 promoter.

A mature POx or a POx fusion polypeptide of the invention can be expressed by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the POx polynucleotides can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, e.g., Ausubel, et al. (eds.) CURRENT PROTOCOLS IN MOLECULAR BIOLOGY, John Wiley & Sons, 1992). A POx signal peptide-encoding nucleic acid can be cloned into an expression vector such that the fusion moiety e.g. polypeptide of interest, is linked in-frame to the POx signal peptide. An expression vector comprising a polynucleotide encoding a POx signal peptide can be any vector capable of expressing the polynucleotide encoding the mature form of the POx polypeptide or the POx signal peptide fused to the mature portion of the POx polypepitde in a selected host organism, and the choice of vector will depend on the host cell into which the expression vector is introduced. Thus, in some embodiments, the invention provides expression vectors that comprise a nucleotide sequence encoding a POx signal peptide, as recited herein, operably linked to a nucleotide sequence encoding a heterologous POx polypeptide. In another embodiment, the vectors of the invention comprise a polynucleotide sequence that encodes a POx polypeptide that lacks a signal peptide.

In some preferred embodiments, the POx polynucleotide is ligated into an appropriate expression plasmid. The cloned POx gene is then used to transform or transfect a host cell in order to express the POx gene. This plasmid may replicate in hosts in the sense that it contains the well-known elements necessary for plasmid replication or the plasmid may be designed to integrate into the host chromosome. The necessary elements are provided for efficient gene expression (e.g., a promoter operably linked to the gene of interest). In some embodiments, these necessary elements are supplied as the gene's own homologous promoter if it is recognized, (i.e., transcribed, by the host), a transcription terminator (a polyadenylation region for eukaryotic host cells) which is exogenous or is supplied by the endogenous terminator region of the POx gene. In some embodiments, a selection gene such as an antibiotic resistance gene that enables continuous cultural maintenance of plasmid-infected host cells by growth in antimicrobial-containing media is also included.

The mature POx polypeptides or POx fusion polypeptides may, in addition, can comprise a tag sequence that is fused to the C-terminus of the POx fusion polypeptide to generate a tagged POx fusion polypeptide. Such tag sequences can be used to identify transformants and/or to facilitate the purification of recombinant Tat fusion polypeptides. For example, the POx fusion polypeptide it may be expressed to contain a tag such as those of maltose binding protein (MBP), glutathione-S-transferase (GST) or thioredoxin (TRX), or as a His tag. Kits for expression and purification of such fusion proteins are commercially available from New England BioLab (Beverly, Mass.), Pharmacia (Piscataway, N.J.) and Invitrogen, respectively. The POx fusion polypeptide can also be tagged with an epitope and subsequently purified by using a specific antibody directed to such epitope. One such epitope ("FLAG®") is commercially available from Kodak (New Haven, Conn.). Another tag that can be used in the invention is the c-myc tag, as is described in the examples.

It is intended that although preferred enzymes for use in the vectors and methods of the invention are referred to herein by their specific SEQ ID NOS, the present invention encompasses enzymes which are derived from the nucleic acids which encode the corresponding amino acid SEQ ID NOS, when expressed, either in their native host species or a heterologous host species. Thus, the present invention encompasses embodiments in which the enzymes are co- or post-translationally processed.

The chimeric polynucleotides of the invention encode POx fusion proteins that are directed to a secretory pathway which leads to the secretion of the mature forms of the POx enzymes. In some embodiments, the fusion polypeptide comprises a Tat signal peptide that is the secretory leader sequence of polypeptides that are naturally expressed by *Streptomyces* and/or *Bacillus* that is operably linked to a mature form of a POx polypeptide. In some embodiments, the signal peptide is a TAT signal peptide. In other embodiments, the signal peptide is a SEC signal peptide. In some embodiments, the fusion proteins of the invention comprise a signal peptide encoded by the *S. coelicolor* SCO6772 gene (SEQ ID NO:15), the signal sequence encoded by the *S. coelicolor* celA gene (EMBL accession no. AL939132.1; SEQ ID NO: 27); the signal sequence encoded by the *S. coelicolor* secreted endoglucanase gene SCO7363 (SEQ ID NO:31), or the signal sequence encoded by the *S. coelicolor* possible secreted protein gene SCO0624 (SEQ ID NO: 39). In yet other embodiments, the fusion proteins of the invention comprise SEC signal peptide of the *Bacillus circulans* cyclomaltodextrin glucanotransferase (cgt) precursor (Accession no. P43379; SEQ ID NO:36). It is understood that any signal peptide capable of directing the fusion protein of the invention to a secretory pathway finds use in the present invention.

The mature forms of the POx enzymes of the invention can be the POx enzymes identified from a number of microorganisms including but not limited to *Streptomyces* sp., *Bacillus* sp., *Acidothermus* sp., *Arthobacter* sp., and marine *Acinobacteium* sp. In some preferred embodiments, the *Streptomyces* sp. include *Streptomyces* strain H-7775, *Streptomyces lividans*, *Streptomyces avermitilis*, *Streptomyces coelicolor* and *Streptomyces* species IKD472. In other preferred embodiments, the *Acidothermus* sp. is *Acidothermus cellulolyticus* 11B (Q2E2H5). In some embodiments, the *Arthobacter* sp. is *Arthrobacter* sp. FB24 (Q4NJLO). In some embodiments, the marine *Actinobacterium* is *Actinobacterium* PHSC20C1.

POx enzymes encompassed by the invention include homologous or heterologous POx proteins. POx enzymes of interest include full-length POx polypeptides that are naturally synthesized with a signal peptide, the mature form of the full-length POx polypeptides, and POx polypeptides that naturally lack a signal peptide.

The mature POx polypeptides and/or the POx fusion polypeptides may, in addition, comprise a tag sequence that is fused to the C-terminus of the mature POx polypeptide and the POx fusion polypeptide to generate a tagged mature POx polypeptide of POx fusion polypeptide. Such tag sequences can be used to identify transformants and/or to facilitate the purification of recombinant POx fusion polypeptides.

For example, the POx fusion polypeptide it may be expressed to contain a tag such as those of maltose binding protein (MBP), glutathione-S-transferase (GST) or thioredoxin (TRX), or as a His tag. Kits for expression and purification of such fusion proteins are commercially available from New England BioLab (Beverly, Mass.), Pharmacia (Piscataway, N.J.) and Invitrogen, respectively. The Tat fusion polypeptide can also be tagged with an epitope and subsequently purified by using a specific antibody directed to such epitope. One such epitope ("FLAG®") is commercially available from Kodak (New Haven, Conn.). Another tag that can be used in the invention is the c-myc tag.

Some preferred embodiments of fusion proteins include the fusion protein of SEQ ID NO:16 which comprises the mature form of *Streptomyces* species H-7775 (SEQ ID NO:2) operably linked (fused) to the signal peptide of *Streptomyces coelicolor* gene SCO6772 (SEQ ID NO:15); the fusion protein of SEQ ID NO:28 which comprises the mature form of *Streptomyces* species H-7775 (SEQ ID NO:2) operably linked (fused) to the signal peptide of *Streptomyces coelicolor* celA gene (EMBL Accession No. AL939132.1; SEQ ID NO:27). Other preferred embodiments of fusion proteins include the fusion protein of SEQ ID NO:38, which comprises the signal peptide of the *Bacillus* cgt precursor (SEQ ID NO:36) fused to the mature form of the POx protein of *Streptomyces* species H-7775 (SEQ ID NO:2); the fusion protein of SEQ ID NO:35, which comprises the signal peptide of the secreted endoglucanase from *Streptomyces coelicolor* SCO 7363 (SEQ ID NO:31) fused to the mature form of the POx protein of *Acidothermus cellulolyticus* (SEQ ID NO:6); the fusion protein of SEQ ID NO:37, which comprises the signal peptide of the signal peptide of the *Bacillus* cgt precursor (SEQ ID NO:36) fused to the mature form of the POx protein of *Acidothermus cellulolyticus* (SEQ ID NO:6); the fusion protein of SEQ ID NO:40, which comprises the signal peptide of the secreted protein *Streptomyces coelicolor* SCO0624 (SEQ ID NO:39) fused to the mature form of the POx protein of *Arthrobacter* sp. gene FB24 (Q4NJLO; SEQ ID NO:11).

In some embodiments, the POx enzyme of the invention is expressed without a signal peptide. Any POx expressed in the absence of a signal peptide will not be translocated to the outside of the host cell, but will remain confined to the intracellular milieu. Examples of POx enzymes that are expressed intracellularly include the POx enzyme from *Streptomyces* sp. H-7775 (SEQ ID NO:2), the POx enzyme of *Streptomyces lividans* (SEQ ID NO:4) and the POx enzyme of *Acidothermus* sp. 11B (SEQ ID NO:6).

The invention encompasses POx proteins that are related to the POx polypeptide of SEQ ID NO:2, 4, 5, 6, 7, 8, 9, 10, 11, 12, 13, 14, 16, 28, 33, 35, 37, 38, and/or 40. In some embodiments, the invention encompasses variant proteins of SEQ ID NO:2, 4, 5, 6, 7, 8, 9, 10, 11, 12, 13, 14, 16, 28, 33, 35, 37, 38, and/or 40. In some preferred embodiments, variant proteins differ from a parent protein and one another by a small number of amino acid residues. The number of differing amino acid residues may be one or more, preferably 1, 2, 3, 4, 5, 10, 15, 20, 30, 40, 50, or more amino acid residues. In some preferred embodiments, the number of different amino acids between variants is between 1 and 10. In some particularly preferred embodiments, related proteins and particularly variant proteins share at least about 70%, about 75%, about 80%, about 85%, about 90%, about 95%, about 97%, about 98%, or about 99% amino acid sequence identity with the amino acid sequence of the precursor POx and have comparable or enhanced POx activity of the precursor polypeptide.

In preferred embodiments, the invention encompasses variants of POx proteins of SEQ ID NO: 2, 4, 5, 6, 7, 8, 9, 10, 11, 12, 13, 14, 16, 28, 33, 35, 37, 38, and/or 40. As used herein, the term "variant(s)" as used in context of a polypeptide sequence refers to a polypeptide prepared from the original (i.e., parent) polypeptide, or by using the sequence information from the original (i.e., parent) polypeptide, by insertion, deletion and/or substitution of one or more amino acids in the original (i.e., parent) sequence. In some embodiments, at least one insertion, deletion, and/or substitution is made in the original (i.e., parent) sequence, while in other embodiments, preferably less than about 50 amino acids, less than about 40, less than about 30, less than about 20, or less than about 10 amino acids are modified by insertion, deletion and/or substitution of the original (i.e., parent) sequence in order to produce variant polypeptides. In some preferred embodiments, only one amino acid modification (i.e., insertion, deletion or substitution) is made, while in other preferred embodiments two amino acids are modified, and in still further embodiments, three amino acids are modified, and in yet additional embodiments, four amino acids are modified, and in still further embodiments, five amino acids are modified. It is not intended that the variants of the present invention be limited to any specific number nor type of amino acid modifications.

In other preferred embodiments, the invention encompasses homologues of the POx polypeptides of SEQ ID NO: 2, 4, 5, 6, 7, 8, 9, 10, 11, 12, 13, 14, 16, 28, 33, 35, 37, 38, and/or 40. The homologs of the POx polypeptides have are at least about 70% homologous, more preferably at least about 80% homologous, still more preferably at least about 85% homologous, further more preferably at least about 90% homologous, even more preferably at least about 95%, more preferably about 96%, still more preferably about 97%, even more preferably about 98%, or most preferably about 99% homologous to the polypeptide sequence of interest (e.g., a sorbitol oxidase provided by the present invention). In some embodiments, homology between two polypeptide sequences is determined using ClustalW alignment algorithm using standard settings, as referred to herein. However, it is not intended that the present invention be limited to any particular method for determining homology.

The variants, homologues and fragments provided by the present invention all retain at least some of the desired enzymatic activity of the parent enzyme, such as at least about 10%, at least about 20%, at least about 30%, at least about 40%, at least about 50%, at least about 60%, at least about 70%, at least about 80% at least about 90%, or all the enzyme activity of the parent enzyme. In some alternative embodiments, the variants and/or homologues have greater enzymatic activity than the original (i.e., parent) enzyme.

The POx enzymes of the present invention were found to be thermally stable and stable over a wide pH range. For example the POx of SEQ ID NO:4 was found to have SOx activity at pH ranging from pH3.5 to 5.5, from pH 5.5-6.7, from pH 6-8, and from pH 7.6-9.0 at a temperature of 25° C. In preferred embodiments, the POx enzyme of the invention exhibits maximal activity at pH 5.5, pH 6.0 and pH 8.0. The POx of the invention retain at least 60% activity, more preferable at least 70% activity, more preferably at least 80% activity, more preferably at least 90% activity, more preferably at least 95% activity. Indeed, the pH profiles of the sorbitol oxidases of the present invention are compatible with the pHs necessarily used in industry, as well as detergents and other cleaning agents.

It is contemplated that the oxidases of the present invention will find use in numerous applications, including but not limited to cleaning compositions (e.g., laundry and dish detergents, etc.), personal care (e.g., oral care, skin care, etc.), textile processing, diagnostics (e.g., medical diagnostic methods), biosensors, and other suitable applications.

Suitable host cells for use in the present invention are members of those genera capable of being utilized for industrial biosynthetic production of desired POx enzymes. Accordingly, host cells can include prokaryotes belonging to the genera *Escherichia, Corynebacterium, Brevibacterium, Acidothermus, Arthrobacter, Bacillus, Pseudomonas, Streptomyces, Staphylococcus*, or *Serratia*. Eukaryotic host cells can also be utilized, with yeasts of the genus *Saccharomyces* or *Schizosaccharomyces* being included.

More specifically, prokaryotic host cells suitable for use in the present invention include, but are not limited to, *Escherichia coli, Bacillus brevis, Bacillus cereus, Bacillus mesentericus, B. licheniformis, B. lentus, B. subtilis, B. amyloliquefaciens, B. lentus, B. brevis, B. stearothermophilus, B. alkalophilus, B. coagulans, B. circulans, B. pumilus, B. thuringiensis, B. clausii, B. megaterium, S. lividans, Streptomyces aureofaciens, Strepbomyces avermitilis, Streptomyces coelicolor, Streptomyces griseus, Streptomyces kasugensis, Streptomyces murinus, S. rubiginosus*, and *S. griseus*. In preferred embodiments, the host cells for use in the present invention include *Streptomyces* sp. H-7775, *S. lividans, E. coli, Acidothermus* and *B. subtilis*. In some preferred embodiments, the host cells are *Streptomyces*, in other embodiments, the host cells are *E. coli*, in yet other embodiments, the host cells are *Acidothermus*, and in still other embodiments, the host cells are *Bacillus*. Indeed, it is not intended that the present invention be limited to any particular species of host cells, as various organisms find use as host cells of the present invention.

The present invention provides host cells comprising a recombinant expression vector comprising at least one polynucleotide sequence encoding at least one polypeptide selected from SEQ ID NOS:2, 4, 5, 6, 7, 8, 9, 10, 11, 12, 13, 14, 15, 16, 28, 33, 35, 37, 38, and/or 40 or homologues, fragments or variants thereof. In alternative embodiments, the host cells comprise at least one polynucleotide sequence encoding at least one polypeptide selected from SEQ ID NOS: SEQ ID NOS:2, 4, 5, 6, 7, 8, 9, 10, 11, 12, 13, 14, 15, 16, 28, 33, 35, 37, 38, and/or 40 or homologues, fragments or variants thereof. In some embodiments, polynucleotide sequence encoding at least one polypeptide selected from SEQ ID NOS:2, 4, 5, 6, 7, 8, 9, 10, 11, 12, 13, 14, 15, 16, 28, 33, 35, 37, 38, and/or 40 or homologues, fragments or variants thereof is present in the genome of the host cell. In other embodiments, polynucleotide sequence encoding at least one polypeptide selected from SEQ ID NOS:2, 4, 5, 6, 7, 8, 9, 10, 11, 12, 13, 14, 15, 16, 28, 33, 35, 37, 38, and/or 40 or homologues, fragments or variants thereof is present in a vector that replicates autonomously in the host cell.

In some embodiments, the invention provides E. coli host cells comprising a polynucleotide that encodes a POx polypeptide of SEQ ID NOS:2, 4, 5, 6, 7, 8, 9, 10, 11, 12, 13, 14, 15, 16, 28, 33, 35, 37, 38, and/or 40. In preferred embodiments, the E. coli host cell comprises a POx polypeptide that encodes a POx protein of SEQ ID NO:2 or 4. In other embodiments, host cells of the invention are S. lividans cells that comprise a polynucleotide that encodes a POx polypeptide of SEQ ID NOS:2, 4, 5, 6, 7, 8, 9, 10, 11, 12, 13, 14, 15, 16, 28, 33, 35, 37, 38, and/or 40. In preferred embodiments, the S. lividans host cell comprises a POx polypeptide that encodes a POx protein of SEQ ID NO:2, 4, 6 and/or 11, 16, 28, 35 and/or 40. In yet other embodiments, host cells of the invention are B. subtilis cells that comprise a polynucleotide that encodes a POx polypeptide of SEQ ID NOS:2, 4, 5, 6, 7, 8, 9, 10, 11, 12, 13, 14, 15, 16, 28, 33, 35, 37, 38, and/or 40. In preferred embodiments, the B. subtilis host cell comprises a POx polypeptide that encodes a POx protein of SEQ ID NO:2, 6 and/or 38.

In some preferred embodiments, the expression of the at least one polypeptide having oxidase activity is extracellular, while in other embodiments, the expression is intracellular.

Host cells transformed with POx polynucleotide sequences encoding heterologous or homologous protein may be cultured under conditions suitable for the expression and recovery of the encoded protein from cell culture.

The present invention provides methods of using the above-described cells for the production of at least one recombinant POx polypeptide. In some embodiments, the methods include culturing a host cell of the invention to produce a POx protein. In some embodiments, the methods include providing a recombinant expression vector that contains a POx polynucleotide that encodes a POx enzyme; transforming the host cell with the expression vector to produce a transformed host cell; and growing the transformed host cell under conditions suitable for the expression of the at least one polypeptide; and recovering the at least one polypeptide expressed by the transformed host cell. In some additional embodiments and as discussed above, the protein is secreted into the culture medium. In yet further embodiments, the methods comprise the step of recovering the protein from the culture medium. Alternatively, the methods comprise the step of recovering the protein from within the host cell. Preferred embodiments provide for the production of at least one recombinant polypeptide, wherein said at least one polypeptide exhibits oxidase activity, wherein the polypeptide comprises SEQ ID NOS:2, 4, 5, 6, 7, 8, 9, 10, 11, 12, 13, 14, 15, 16, 28, 33, 35, 37, 38, and/or 40 or homologues, fragments or variants thereof, comprising: (a) providing: a recombinant expression vector, wherein said expression vector comprises at least one polynucleotide sequence encoding at least one of said polypeptides selected from SEQ ID NOS: 2, 4, 5, 6, 7, 8, 9, 10, 11, 12, 13, 14, 15, 16, 28, 33, 35, 37, 38, and/or 40 or homologues, fragments or variants thereof; and a host cell; (b) transforming the host cell with the expression vector to produce a transformed host cell; (c) growing the transformed host cell under conditions suitable for the expression of at least one polypeptide; and (d) recovering at least one polypeptide expressed by the transformed host cell. In some preferred embodiments, the oxidase activity is polyol oxidase activity. In some particularly preferred embodiments, the oxidase activity is sorbitol oxidase activity, while in some alternative particularly preferred embodiments, the oxidase activity is xylitol oxidase activity.

In some preferred embodiments, the POx protein expressed by the host cells is recovered by the removal of other host cell constituents in the growth media using any convenient method (e.g., by precipitation, centrifugation, affinity, filtration) or any other suitable method known in the art. For example, affinity chromatography (Tilbeurgh et al., FEBS Lett., 16:215 [1984]); ion-exchange chromatographic methods (Goyal et al., Biores. Technol., 36:37 [1991]; Fliess et al., Eur. J. Appl. Microbiol. Biotechnol. 17:314 [1983]; Bhikhabhai et al., J. Appl. Biochem., 6:336 [1984]; and Ellouz et al., Chromatography 396:307 [1987]), including ion-exchange using materials with high resolution power (Medve et al., J. Chromatography A 808:153 [1998]; hydrophobic interaction chromatography (Tomaz and Queiroz, J. Chromatography A 865:123 [1999]; two-phase partitioning (Brumbauer et al., Bioseparation 7:287 [1999]); ethanol precipitation; reverse phase HPLC; chromatography on silica or on a cation-exchange resin such as DEAE; chromatofocusing; SDS-PAGE; ammonium sulfate precipitation; and gel filtration (e.g., using SEPHADEX G-75), find use in the present invention. In particularly preferred embodiments, the sorbitol oxidases of the present invention are substantially purified to a level of at least about 99% of the protein component, as determined by SDS-PAGE or other standard methods known in the art.

The invention also encompasses POx fusion polypeptides that comprise a signal peptide and a heterologous peptide and a polypeptide domain that will facilitate purification of POx enzymes (Kroll D J et al (1993) DNA Cell Biol 12:441-53). Such purification facilitating domains include, but are not limited to, metal chelating peptides such as histidine-tryptophan modules that allow purification on immobilized metals (Porath J (1992) Protein Expr Purif 3:263-281), protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen, San Diego Calif.) between the purification domain and the heterologous protein can be used to facilitate purification. In some particular embodiments, the sorbitol oxidase is used without purification from the other components in the culture medium. In some embodiments, the components of the culture medium are simply concentrated and then used without further purification of the POx protein from the other components of the growth medium in order to produce a cleaning and/or other composition.

In some embodiments, recombinant POx are expressed in bacterial or fungal host cells and these recombinant POx are purified by the removal of other host cell constituents; the percent of recombinant POx polypeptides is thereby increased in the sample. In particularly preferred embodiments, the POx of the present invention are substantially purified to a level of at least about 99% of the protein component, as determined by SDS-PAGE or other standard methods known in the art.

Means for determining the levels of secretion of a heterologous or homologous protein in a gram-positive host cell and detecting secreted proteins include, using either polyclonal or monoclonal antibodies specific for the protein.

Examples include enzyme-linked immunosorbent assay (ELISA), radioimmunoassay (RIA) and fluorescent activated cell sorting (FACS). These and other assays are described, among other places, in Hampton R et al (1990, Serological Methods, a Laboratory Manual, APS Press, St Paul Minn.) and Maddox D E et al (1983, J Exp Med 158:1211).

A wide variety of labels and conjugation techniques are known by those skilled in the art and can be used in various nucleic and amino acid assays. Means for producing labeled hybridization or PCR probes for detecting specific polynucleotide sequences include oligo labeling, nick translation, end-labeling or PCR amplification using a labeled nucleotide. Alternatively, the nucleotide sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. The enzymatic activity of a secreted SOx-fusion polypeptide can be determined by contacting the secreted polypeptide with a substrate and detecting the reaction product produced by the action of the enzyme on the substrate. In addition, verifying that the correct enzyme or other reporter molecule is secreted can be accomplished by performing mass spectroscopy of the secreted protein.

In some embodiments, the host cells are cultured under batch, fed-batch or continuous fermentation conditions. Classical batch fermentation methods use a closed system, wherein the culture medium is made prior to the beginning of the fermentation run, the medium is inoculated with the desired organism(s), and fermentation occurs without the subsequent addition of any components to the medium. In certain cases, the pH and oxygen content, but not the carbon source content, of the growth medium is altered during batch methods. The metabolites and cell biomass of the batch system change constantly up to the time the fermentation is stopped. In a batch system, cells usually progress through a static lag phase to a high growth log phase and finally to a stationary phase where growth rate is diminished or halted. If untreated, cells in the stationary phase eventually die. In general terms, the cells in log phase produce most protein.

A variation on the standard batch system is the "fed-batch fermentation" system. In this system, nutrients (e.g., a carbon source, nitrogen source, $O_2$, or other nutrient) are only added when their concentration in culture falls below a threshold. Fed-batch systems are useful when catabolite repression is apt to inhibit the metabolism of the cells and where it is desirable to have limited amounts of nutrients in the medium. Measurement of the actual nutrient concentration in fed-batch systems is estimated on the basis of the changes of measurable factors such as pH, dissolved oxygen and the partial pressure of waste gases such as $CO_2$. Batch and fed-batch fermentations are common and known in the art.

Continuous fermentation is an open system where a defined culture medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth and/or end product concentration. For example, in some embodiments, a limiting nutrient such as the carbon source or nitrogen source is maintained at a fixed rate and all other parameters are allowed to moderate. In other systems, a number of factors affecting growth are altered continuously while the cell concentration, measured by media turbidity, is kept constant. Continuous systems strive to maintain steady state growth conditions. Thus, cell loss due to medium being drawn off may be balanced against the cell growth rate in the fermentation. Methods of modulating nutrients and growth factors for continuous fermentation processes as well as techniques for maximizing the rate of product formation are known to those of skill in the art and find use in the production of the POx enzymes of the present invention.

The POx protein produced using the above described methods finds use in any product containing a POx, including, but not limited to cleaning compositions, (e.g., fabric cleaning compositions, such as laundry detergents, surface cleaning compositions, dish cleaning compositions and automatic dishwasher detergent compositions; See e.g., WO0001826, which is incorporated by reference herein), bleaching and disinfecting compositions.

The cleaning compositions and cleaning additives of the present invention require an effective amount of the POx enzymes provided by the present invention. The required level of enzyme may be achieved by the addition of one or more POx enzymes, variants, homologues, and/or other enzymes or enzyme fragments having the activity of the POx enzymes of the present invention. Typically, the cleaning compositions of the present invention comprise at least 0.1 ppm to about 10 ppm, from about 0.5 to about 2 ppm, or from about 1 to about 5 ppm. In some preferred embodiments, the cleaning compositions of the present invention comprise about 0.2 to about 1 ppm of POx enzymes. The cleaning compositions that comprise at least one POx enzyme in combination with a perhydrolase enzyme comprise an effective amount of POx enzyme as recited herein and an effective amount of perhydrolase that comprises about 0.1 to about 10 ppm, about 0.5 to about 10 ppm or about 1 to about 5 ppm of perhydrolase. In preferred embodiments, the amount of perhydrolase contained in the cleaning compositions is from about 0.2 of about 1 ppm. In some embodiments, the cleaning compositions comprise a perhydrolase substrate as recited above in amounts from about 0.2 to about 20 mM, or from about 0.5 to about 15 mM, from about 1 to about 10 mM. In preferred embodiments, the amount of perhydrolase substrate contained in the cleaning composition comprises from about 1 to about 5 mM of perhydrolase substrate.

In some particular embodiments, the POx protein is used in an POx-containing laundry detergent comprising from about 1% to about 80%, e.g., about 5% to about 50% (by weight) of surfactant, which may be a non-ionic surfactant, cationic surfactant, an anionic surfactant or a zwitterionic surfactant, or any mixture thereof (e.g., a mixture of anionic and non-ionic surfactants). Exemplary surfactants include: alkyl benzene sulfonate (ABS), including linear alkyl benzene sulfonate and linear alkyl sodium sulfonate, alkyl phenoxy polyethoxy ethanol (e.g., nonyl phenoxy ethoxylate or nonyl phenol), diethanolamine, triethanolamine and monoethanolamine. Exemplary surfactants that find use in laundry detergents are known in the art (See e.g., U.S. Pat. Nos. 3,664,961, 3,919,678, 4,222,905, and 4,239,659).

The laundry detergent may be in solid, liquid, gel or bar form, and may further contain a buffer such as sodium carbonate, sodium bicarbonate, or detergent builder, bleach, bleach activator, various enzymes, an enzyme stabilizing agent, suds booster, suppresser, anti-tarnish agent, anti-corrosion agent, soil suspending agent, soil release agent, germicide, pH adjusting agent, non-builder alkalinity source, chelating agent, organic or inorganic filler, solvent, hydrotrope, optical brightener, dye or perfumes. In some preferred embodiments, the laundry detergent comprises in addition to the POx enzymes of the present invention, at least one further enzyme (e.g., hemicellulase, peroxidase, protease, cellulase, xylanase, lipase, phospholipase, esterase, cutinase, pectinase, keratinase, reductase, oxidase, phenoloxidase, lipoxygenase, ligninase, pullulanase, tannase, pentosanase, mannanase, β-glucanase, arabinosidase, hyaluronidase, chondroitinase, laccase, and amylases, or mixtures thereof).

The POx protein of the present invention finds use in any suitable composition useful for cleaning a variety of surfaces in need of stain removal. Such cleaning compositions include detergent compositions for cleaning hard surfaces, unlimited in form (e.g., liquid, gel, bar and granular formation); detergent compositions for cleaning fabrics, unlimited in form (e.g., granular, liquid, gel and bar formulations); dishwashing compositions (unlimited in form); oral cleaning compositions, unlimited in form (e.g., dentifrice, toothpaste, gel and mouthwash formulations); denture cleaning compositions, unlimited in form (e.g., liquid, gel or tablet); and contact lens cleaning compositions, unlimited in form (e.g., liquid, tablet).

In some embodiments, the cleaning compositions of the present invention comprise an effective amount of a POx, alone or in combination with other POx enzymes and/or a perhydrolase enzyme as recited above. In one embodiment, the cleaning composition comprises a POx of SEQ ID NO:2, 4, 5, 6, 7, 8, 9, 10, 11, 12, 13, 14, 15, 16, 28, 33, 35, 37, 38, and/or 40. In one embodiment, the cleaning composition comprises a POx of SEQ ID NO:2, 4, 5, 6, 7, 8, 9, 10, 11, 12, 13, 14, 15, and/or 16. In one preferred embodiment, the cleaning composition comprises a POx of SEQ ID NO:2, 4, 6, and/or 11.

In yet other embodiments, the cleaning composition comprises a POx of SEQ ID NO:2, 4, 5, 6, 7, 8, 9, 10, 11, 12, 13, 14, 15, 16, 28, 33, 35, 37, 38, and/or 40 in combination with at least one additional enzyme including enzymes that are hemicellulases, peroxidases, proteases, cellulases, xylanases, lipases, phospholipases, esterases, cutinases, pectinases, keratinases, reductases, oxidases, oxidoreductases, perhydrolases, phenoloxidases, lipoxygenases, ligninases, pullulanases, tannases, pentosanases, mannanases, β-glucanases, arabinosidases, hyaluronidases, chondroitinases, laccases, and amylases. In yet other embodiments, the cleaning composition comprises a POx of SEQ ID NO:2, 4, 5, 6, 7, 8, 9, 10, 11, 12, 13, 14, 15, and/or 16 in combination with at least one additional enzyme including enzymes that are hemicellulases, peroxidases, proteases, cellulases, xylanases, lipases, phospholipases, esterases, cutinases, pectinases, keratinases, reductases, oxidases, oxidoreductases, perhydrolases, phenoloxidases, lipoxygenases, ligninases, pullulanases, tannases, pentosanases, mannanases, β-glucanases, arabinosidases, hyaluronidases, chondroitinases, laccases, and amylases. In another preferred embodiments, the cleaning composition comprises a POx of SEQ ID NO:2, 4, 6, and/or 11 in combination with at least one additional enzyme including enzymes that are hemicellulases, peroxidases, proteases, cellulases, xylanases, lipases, phospholipases, esterases, cutinases, pectinases, keratinases, reductases, oxidases, oxidoreductases, perhydrolases, phenoloxidases, lipoxygenases, ligninases, pullulanases, tannases, pentosanases, mannanases, β-glucanases, arabinosidases, hyaluronidases, chondroitinases, laccases, and amylases. In another embodiment, the cleaning composition comprises a POx of SEQ ID NO:2, 4, 5, 6, 7, 8, 9, 10, 11, 12, 13, 14, 15, 16, 28, 33, 35, 37, 38, and/or 40 in combination with a perhydrolase. In another embodiment, the cleaning composition comprises a POx of SEQ ID NO:2, 4, 5, 6, 7, 8, 9, 10, 11, 12, 13, 14, 15, and/or 16 in combination with a perhydrolase. In a preferred embodiment, the cleaning composition comprises a POx of SEQ ID NO:2, 4, 6, and/or 11 in combination with a perhydrolase. In another embodiment, the cleaning composition comprises a POx of SEQ ID NO:2, 4, 5, 6, 7, 8, 9, 10, 11, 12, 13, 14, 15, 16, 28, 33, 35, 37, 38, and/or 40 in combination with a bleach activator. In another embodiment, the cleaning composition comprises a POx of SEQ ID NO:2, 4, 5, 6, 7, 8, 9, 10, 11, 12, 13, 14, 15, and/or 16 in combination with a bleach activator. In a preferred embodiment, the cleaning composition comprises a POx of SEQ ID NO:2, 4, 6, and/or 11 in combination with a bleach activator.

In some embodiments, the cleaning compositions of the present invention comprise one or more detergent enzymes which provide cleaning, bleaching and/or disinfecting benefits. Examples of suitable enzymes include, but are not limited to, hemicellulases, peroxidases, proteases, cellulases, xylanases, lipases, phospholipases, esterases, cutinases, pectinases, keratinases, reductases, carrageenases, phenoloxidases, lipoxygenases, ligninases, pullulanases, tannases, pentosanases, mannanases, β-glucanases, arabinosidases, hyaluronidase, chondroitinase, laccase, and amylases, or mixtures thereof. In some embodiments, a combination of enzymes is used (i.e., a "cocktail") comprising conventional applicable enzymes like protease, lipase, cutinase and/or cellulase in conjunction with the POx or POx-perhydrolase combination in the presence or absence of a bleach activator.

In some embodiments, the cleaning compositions also comprise, in addition to the proteins described herein, one or more cleaning composition materials compatible with the POx protein. As described herein, the term "cleaning composition material," refers any liquid, solid or gaseous material selected for the particular type of cleaning composition desired and the form of the product (e.g., liquid, granule, bar, spray, stick, paste, gel), which materials are also compatible with the POx or POx-perhydrolase combinations used in the composition either in the presence or absence of a bleach activator. The specific selection of cleaning composition materials are readily made by considering the surface material to be cleaned, the desired form of the composition for the cleaning condition during use (e.g., through the wash detergent use). As used herein, "non-fabric cleaning compositions" include hard surface cleaning compositions, dishwashing compositions, oral cleaning compositions, denture cleaning compositions and contact lens cleaning compositions.

The POx protein finds use with various conventional ingredients to provide fully-formulated hard-surface cleaners, dishwashing compositions, fabric laundering compositions, and the like. Such compositions find use in the form of liquids, granules, bars and the like. In some embodiments, such compositions are formulated as modern "concentrated" detergents which contain as much as about 30% to about 60% by weight of surfactants.

In some embodiments, the cleaning compositions of the present invention comprise various anionic, nonionic, zwitterionic, etc., surfactants. Such surfactants are typically present at levels of from about 5% to about 35% of the compositions. Surfactants include nonionic, anionic, cationic, anionic or zwitterionic detergents (See e.g., U.S. Pat. Nos. 4,404,128 and 4,261,868). A suitable detergent formulation is that described in U.S. Pat. No. 5,204,015 (previously incorporated by reference). Those in the art are familiar with the different formulations which find use as cleaning compositions. As indicated above, in some preferred embodiments, the detergent compositions of the present invention employ a surface active agent (i.e., surfactant) including anionic, nonionic and ampholytic surfactants well known for their use in detergent compositions. Some surfactants suitable for use in the present invention are described in British Patent Application No. 2 094 826 A, incorporated herein by reference. In some embodiments, mixtures surfactants are used in the present invention.

Suitable anionic surfactants for use in the detergent composition of the present invention include linear or branched alkylbenzene sulfonates; alkyl or alkenyl ether sulfates having linear or branched alkyl groups or alkenyl groups; alkyl or alkenyl sulfates; olefin sulfonates; alkane sulfonates and the like. Suitable counter ions for anionic surfactants include alkali metal ions such as sodium and potassium; alkaline earth metal ions such as calcium and magnesium; ammonium ion; and alkanolamines having 1 to 3 alkanol groups of carbon number 2 or 3.

Ampholytic surfactants that find use in the present invention include quaternary ammonium salt sulfonates, betaine-type ampholytic surfactants, and the like. Such ampholytic surfactants have both the positive and negative charged groups in the same molecule.

Nonionic surfactants that find use in the present invention generally comprise polyoxyalkylene ethers, as well as higher fatty acid alkanolamides or alkylene oxide adduct thereof, fatty acid glycerine monoesters, and the like.

In some preferred embodiments, the surfactant or surfactant mixture included in the detergent compositions of the present invention is provided in an amount from about 1 weight percent to about 95 weight percent of the total detergent composition and preferably from about 5 weight percent to about 45 weight percent of the total detergent composition. In various embodiments, numerous other components are included in the compositions of the present invention. Many of these are described below. It is not intended that the present invention be limited to these specific examples. Indeed, it is contemplated that additional compounds will find use in the present invention. The descriptions below merely illustrate some optional components.

In some embodiments of the present invention, the composition contains from about 0 to about 50 weight percent of one or more builder components selected from the group consisting of alkali metal salts and alkanolamine salts of the following compounds: phosphates, phosphonates, phosphonocarboxylates, salts of amino acids, aminopolyacetates high molecular electrolytes, non-dissociating polymers, salts of dicarboxylic acids, and aluminosilicate salts. Examples of suitable divalent sequestering agents are disclosed in British Patent Application No. 2 094 826 A, the disclosure of which is incorporated herein by reference.

In additional embodiments, compositions of the present invention contain from about 1 to about 50 weight percent, preferably from about 5 to about 30 weight percent, based on the composition of one or more alkali metal salts of the following compounds as the alkalis or inorganic electrolytes: silicates, carbonates and sulfates as well as organic alkalis such as triethanolamine, diethanolamine, monoethanolamine and triisopropanolamine.

The cleaning compositions herein may contain a chelating agent, Suitable chelating agents include copper, iron and/or manganese chelating agents and mixtures thereof. When a chelating agent is used, the cleaning composition may comprise from about 0.1% to about 15% or even from about 3.0% to about 10% chelating agent by weight of the subject cleaning composition.

In yet additional embodiments of the present invention, the compositions contain from about 0.1 to about 5 weight percent of one or more of the following compounds as antiredeposition agents: polyethylene glycol, polyvinyl alcohol, polyvinylpyrrolidone and carboxymethylcellulose. In some preferred embodiments, a combination of carboxymethylcellulose and/or polyethylene glycol are utilized with the composition of the present invention as useful dirt removing compositions.

The use of the POx enzymes of the present invention are used in combination with additional bleaching agent(s) such as sodium percarbonate, sodium perborate, sodium sulfate/hydrogen peroxide adduct and sodium chloride/hydrogen peroxide adduct and/or a photo-sensitive bleaching dye such as zinc or aluminum salt of sulfonated phthalocyanine further improves the detergent effects. In additional embodiments, the POx enzymes of the present invention are used in combination with bleach boosters (e.g., TAED and/or NOBS).

The cleaning compositions can comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof.

In addition to the ingredients described above, perfumes, buffers, preservatives, dyes and the like also find use with the present invention. Other ingredients useful in detergent cleaning compositions also find use in the compositions herein, including other active ingredients, carriers, hydrotropes, processing aids, dyes or pigments, solvents for liquid formulations, etc. If an additional increment of sudsing is desired, suds boosters such as the $C_{10}$-$C_{16}$ alkylamides also find use in the compositions, typically at about 1% to about 10% levels.

In some embodiments, the detergent compositions comprise water and/or other solvents as carriers. For example, in some embodiments, low molecular weight primary or secondary alcohols (e.g., methanol, ethanol, propanol, and isopropanol) are suitable. Monohydric alcohols are preferred for solubilizing surfactants, but polyols such as those containing from about 2 to about 6 carbon atoms and from about 2 to about 6 hydroxy groups (e.g., 1,3-propanediol, ethylene glycol, glycerine, and 1,2-propanediol) also find use. In such embodiments, the compositions typically contain from about 5% to about 90%, or typically from about 10% to about 50% of such carriers.

In some embodiments, the detergent compositions provided herein are formulated such that during use in aqueous cleaning operations, the wash water will have a pH between about 5.5 and about 10.5. In some preferred embodiments, the pH of the wash water is between about pH 5 and pH 7. In other preferred embodiments the pH of the wash water is between about pH 7 and pH 10.5. Finished products thus are typically formulated at this range. Techniques for controlling pH at recommended usage levels include the use of buffers, alkalis, acids, etc., and are well known to those skilled in the art.

Various bleaching compounds, such as the percarbonates, perborates and the like, also find use in such compositions, typically at levels from about 1% to about 15% by weight. In some embodiments, such compositions also contain bleach activators such as tetraacetyl ethylenediamine, nonanoyloxybenzene sulfonate, and the like, which are also known in the art. Usage levels typically range from about 1% to about 10% by weight.

Various soil release agents, especially of the anionic oligoester type, various chelating agents, especially the aminophosphonates and ethylenediaminedisuccinates, various clay soil removal agents, especially ethoxylated tetraethylene pentamine, various dispersing agents, especially polyacrylates and polyasparatates, various brighteners, especially anionic brighteners, various suds suppressors, especially silicones and secondary alcohols, various fabric softeners, especially smectite clays, and the like, all find use in various embodiments of the present compositions, at levels ranging from about 1% to about 35% by weight. Standard formularies and published patents contain multiple, detailed descriptions of such conventional materials.

Enzyme stabilizers also find use in the cleaning compositions of the present invention. Such stabilizers include, but are not limited to propylene glycol (preferably from about 1% to about 10%), sodium formate (preferably from about 0.1% to about 1%), and calcium formate (preferably from about 0.1% to about 1%).

The cleaning compositions of the present invention are formulated into any suitable form and prepared by any suitable process chosen by the formulator, (See e.g., U.S. Pat. No. 5,879,584, U.S. Pat. No. 5,691,297, U.S. Pat. No. 5,574,005, U.S. Pat. No. 5,569,645, U.S. Pat. No. 5,565,422, U.S. Pat. No. 5,516,448, U.S. Pat. No. 5,489,392, U.S. Pat. No. 5,486,303, U.S. Pat. No. 4,515,705, U.S. Pat. No. 4,537,706, U.S. Pat. No. 4,515,707, U.S. Pat. No. 4,550,862, U.S. Pat. No. 4,561,998, U.S. Pat. No. 4,597,898, U.S. Pat. No. 4,968,451, U.S. Pat. No. 5,565,145, U.S. Pat. No. 5,929,022, U.S. Pat. No. 6,294,514, and U.S. Pat. No. 6,376,445, all of which are incorporated herein by reference for some non-limiting examples). When formulating the hard surface cleaning compositions and fabric cleaning compositions of the present invention, the formulator may wish to employ various builders at levels from about 5% to about 50% by weight. Typical builders include the 1-10 micron zeolites, polycarboxylates such as citrate and oxydisuccinates, layered silicates, phosphates, and the like. Other conventional builders are listed in standard formularies.

Other optional ingredients include chelating agents, clay soil removal/antiredeposition agents, polymeric dispersing agents, bleaches, brighteners, suds suppressors, solvents and aesthetic agents.

In some preferred embodiments, the cleaning compositions of the present invention find use in cleaning surfaces and/or fabrics. In some embodiments, at least a portion of the surface and/or fabric is contacted with at least one embodiment of the cleaning compositions of the present invention, in neat form or diluted in a wash liquor, and then the surface and/or fabric is optionally washed and/or rinsed. For purposes of the present invention, "washing" includes, but is not limited to, scrubbing, and mechanical agitation. In some embodiments, the fabric comprises any fabric capable of being laundered in normal consumer use conditions. In some preferred embodiments, the cleaning compositions of the present invention are used at concentrations of from about 500 ppm to about 15,000 ppm in solution. In some embodiments in which the wash solvent is water, the water temperature typically ranges from about 5° C. to about 70° C. In some preferred embodiments for fabric cleaning, the water to fabric mass ratio is typically from about 1:1 to about 30:1.

In order to further illustrate the present invention and advantages thereof, the following specific Examples are given with the understanding that they are being offered to illustrate the present invention and should not be construed in any way as limiting its scope.

EXPERIMENTAL

The following Examples are provided in order to demonstrate and further illustrate certain preferred embodiments and aspects of the present invention and are not to be construed as limiting the scope thereof.

In the experimental disclosure which follows, the following abbreviations apply: ° C. (degrees Centigrade); rpm (revolutions per minute); $H_2O$ (water); HCl (hydrochloric acid); aa (amino acid); by (base pair); kb (kilobase pair); kD (kilodaltons); gm (grams); μg and ug (micrograms); mg (milligrams); ng (nanograms); μl and ul (microliters); ml (milliliters); mm (millimeters); nm (nanometers); μm and um (micrometer); M (molar); mM (millimolar); μM and uM (micromolar); U (units); V (volts); MW (molecular weight); sec (seconds); min(s) (minute/minutes); hr(s) (hour/hours); $MgCl_2$ (magnesium chloride); NaCl (sodium chloride); $OD_{280}$ (optical density at 280 nm); $OD_{600}$ (optical density at 600 nm); EFT ("effective fermentation time"); HDL (Heavy Duty Detergent Liquid); EtOH (ethanol); PBS (phosphate buffered saline [150 mM NaCl, 10 mM sodium phosphate buffer, pH 7.2]); SDS (sodium dodecyl sulfate); Tris (tris (hydroxymethyl)aminomethane); TAED (N,N,N'N'-tetraacetylethylenediamine); w/v (weight to volume); v/v (volume to volume); GOx and GOx (glucose oxidase); AOX and AOx (alcohol oxidase); COX and Cox (choline oxidase); HOx and HOx (hexose oxidase); SOx and SOx (sorbitol oxidase); PMS (phenazine methosulfate); NCBI (National Center for Biotechnology Information); ATCC (American Type Culture Collection, Manassas, Va.); Geneart (Geneart, Regesburg, Germany); Invitrogen (Invitrogen, Inc., Carlsbad, Calif.); Stratagene (Stratagene, Inc., San Diego, Calif.); Biospringer (Biospringer, Inc., Cedex, France); BASF (BASF, Mt. Olive, N.J.); and Sigma (Sigma-Aldrich Chemical Co., St. Louis, Mo.).

In the following Examples various growth media were used. In these Examples, the TS medium was composed of 16 g Difco tryptone, 4 g Difco soytone, 20 g caseine (hydrolysate) (Sigma), and 5 g $K_2HPO_4$ brought to 1 liter. After autoclaving, 50% filtered sterilized glucose was added to a final concentration of 1.5%. The "Production Medium" was composed of 2.4 g citric acid*$H_2O$; 8.3 g yeast extract (Biospringer); 2.4 g $(NH_4)_2SO_4$; 72.4 g $MgSO_4$*$7H_2O$; 0.1 g $CaCl_2$*$2H_2O$; 0.3 ml Mazu DF204 (BASF); 5 ml *Streptomyces* modified trace elements (1 liter stock solution contains: 250 g citric acid*$H_2O$; 3.25 g $FeSO_4$*$7H_2O$; 5 g $ZnSO_4$*$7H_2O$; 5 g $MnSO_4$*$H_2O$; 0.25 g $H_3BO_3$); 10 g glucose, adjust volume to 1 liter and the pH was adjusted to 6.9, with NaOH. The R5 medium used was the standard R5 medium commonly used to grow *Streptomyces*.

Example 1

Construction of Strains Expressing Sorbitol Oxidase of *Streptomyces* sp. H-7775 in *Streptomyces lividans*

In this Example, methods used to construct the strain that produced the sorbitol oxidase used in the development of the present invention are described. The protein sequence (SEQ ID NO:2) of the sorbitol oxidase was obtained from the published amino acid sequence (See e.g., Hiraga et al., Biosci.

Biotechnol. Biochem., 62: 4347-353 [1998]). The signal sequence of the twin-arginine pathway of the *Streptomyces ceolicolor* SCO6772 gene (SEQ ID NO:15) was obtained from complete genome sequence of *Streptomyces coelicolor*.

(SEQ ID NO: 15)
MTEVSRRKLMKGAAVSGGALALPALGAPPATAAPAAGPEDLPGPAAA

The sorbitol oxidase was expressed in *Streptomyces* as a fusion protein of the signal sequence of the SCO6772 protein (SEQ ID NO:15) and sorbitol oxidase (SEQ ID NO:2). A restriction site for NcoI was introduced at the 5' end of DNA for cloning purposes, which resulted addition of an amino acid glycine residue at position 2 (See, SEQ ID NO:16).

(SEQ ID NO: 16)
MGTEVSRRKLMKGAAVSGGALALPALGAPPATAAPAAGPEDLPGPAAAMTPAEKNWA

GNITFGAKRLCVPRSVRELRETVAASGAVRPLGTRHSFNTVADTSGDHVSLAGLPRVVD

IDVPGRAVSLSAGLRFGEFAAELHARGLALANLGSLPHISVAGAVATGTHGSGVGNRSL

AGAVRALSLVTADGETRTLRRTDEDFAGAVVSLGALGVVTSLELDLVPAFEVRQWVYED

LPEATLAARFDEVMSAAYSVSVFTDWRPGPVGQVWLKQRVGDEGARSVMPAEWLGAR

LADGPRHPVPGMPAGNCTAQQGVPGPWHERLPHFRMEFTPSNGDELQSEYFVARADA

VAAYEALARLRDRIAPVLQVSELRTVAADDLWLSPAHGRDSVAFHFTWVPDAAAVAPVA

GAIEEALAPFGARPHWGKVFSTAPEVLRTLYPRYADFEELVGRHDPEGTFRNAFLDRYF

RR

A restriction site for BamHI was also introduced at the 3' end of DNA for cloning purposes. The codons of the fusion gene were optimized for expression in *Streptomyces lividans*. DNA was synthesized by Geneart. The DNA fragment spanning the two restriction sites (i.e., from NcoI to BamHI (SEQ ID NO:17)) was cloned into *Streptomyces* expression plasmid pKB105 (See, U.S. patent application Ser. No. 11/303,650, filed Dec. 16, 2005, incorporated by reference in its entirety) which was cut with BamHI completely and NcoI partially.

(SEQ ID NO: 17)
CCATGGGCACCGAGGTCTCCCGCCGCAAGCTGATGAAGGGCGCGGCGGT

GTCGGGCGGCGCGCTGGCGCTGCCGGCCCTCGGCGCCCCGCCCGCCACC

GCGGCGCCGGCCGCCGGCCCCGAGGACCTCCCGGGCCCCGCCGCCGCCA

TGACCCCGGCCGAGAAGAACTGGGCCGGCAACATCACCTTCGGCGCCAA

GCGCCTGTGCGTCCCGCGCTCCGTCCGCGAGCTGCGCGAGACCGTGGCC

GCCTCCGGCGCCGTGCGCCCGCTGGGCACCCGCCACTCGTTCAACACCG

TCGCCGACACCTCCGGCGACCACGTGTCGCTGGCCGGCCTGCCGCGCGT

CGTCGACATCGACGTCCCGGGCCGGGCCGTGTCCCTGTCCGCCGGCCTG

CGCTTCGGCGAGTTCGCCGCCGAGCTGCACGCCCGCGGCCTGGCCCTGG

CCAACCTGGGCTCCCTGCCGCACATCTCCGTGGCGGGCGCGGTCGCCAC

CGGCACCCACGGCTCCGGCGTCGGCAACCGCTCCCTGGCGGGCGCCGTC

CGCGCCCTGTCCCTGGTCACCGCCGACGGCGAGACCCGCACCCTGCGCC

GCACCGACGAGGACTTCGCCGGCGCCGTCGTGTCCCTGGGCGCCCTGGG

CGTCGTCACCTCCCTGGAGCTGGACCTGGTCCCGGCCTTCGAGGTCCGC

CAGTGGGTCTACGAGGACCTGCCCGAGGCCACCCTGGCCGCCCGCTTCG

ACGAGGTCATGTCCGCCGCCTACTCCGTGTCCGTGTTCACCGACTGGCG

CCCGGGCCCGGTCGGCCAGGTCTGGCTGAAGCAGCGCGTCGGCGACGAG

GGCGCCCGCTCCGTCATGCCCGGCCGAGTGGCTGGGCGCCCGCCTGGCCG

ACGGCCCGCGCCACCCGGTCCCCGGCATGCCCGCCGGCAACTGCACCGC

CCAGCAGGGCGTCCCGGGCCCGTGGCACGAGCGCCTGCCGCACTTCCGC

ATGGAGTTCACCCCGTCCAACGGCGACGAGCTGCAGTCCGAGTACTTCG

TCGCCCGCGCGGACGCCGTCGCGGCCTACGAGGCGCTGGCCCGCCTGCG

CGACCGCATCGCCCCGGTCCTGCAGGTCTCCGAGCTGCGCACCGTCGCC

GCCGACGACCTGTGGCTGTCCCCGGCCCACGGCCGCGACTCCGTCGCCT

TCCACTTCACCTGGGTCCCGGACGCCGCCGCCGTCGCCCCGGTCGCCGG

CGCCATCGAGGAGGCCCTGGCCCCGTTCGGCGCCCGCCCGCACTGGGGC

AAGGTGTTCTCCACCGCCCCCGAGGTCCTGCGCACCCTGTACCCGCGCT

ACGCCGACTTCGAGGAGCTGGTCGGCCGCCACGACCCCGAGGGCACCTT

CCGCAACGCCTTCCTCGACCGCTACTTCCGCCGCTGAGGATCC

The expression plasmid (pKB105-TAT-SOx7775; FIG. 1; SEQ ID NO:29) was transformed into *Streptomyces lividans* strain g3s3 (See, U.S. patent application Ser. No. 11/305,650, supra) and three transformants were selected and grown in TS medium for 2-3 days in the presence of 50 ug/ml thiostrepton at 30° C. Cells were then transferred to a production medium free of antimicrobials and growth was continued for another three days. Then, 1 ml of the culture was transferred to each of two culture tubes and the cells were removed by centrifugation under conditions sufficient to separate the cells from the supernatants. The supernatants obtained from these two culture tubes were tested in enzyme activity assays.

pKB105 TAT-SOx7775 (9495 bps):

(SEQ ID NO: 29)

ctagagatcgaacttcatgttcgagttcttgttcacgtagaagccggagatgtgagaggtgatctggaactgctcaccctcgtt gtggtgacctggaggtaaagcaagtgacccttctggcggaggtggtaaggaacggggttccacggggagagagagatgg ccttgacggtcttgggaaggggagcttcggcgcggggaggatggtcttgagagaggggagctagtaatgtcgtacttgg acagggagtgctccttctccgacgcatcagccacctcagcggagatggcatcgtgcagagacagaccccggaggtaac catgggcaccgaggtgtcccgccggaaactcatgaaaggcgccgcggtgtccggcggcgcgctggcgctgcccgcgctc ggcgcaccgccggcgacggccgcgcccgccgcaggccccgaggacctccccggccccgcagcggcgatgaccccgg ccgagaagaactgggccggcaacatcaccttcggcgccaagcgcctgtgcgtcccgcgctccgtccgcgagctgcgcga gaccgtggccgcctccggcgccgtgcgcccgctgggcacccgccactcgttcaacaccgtcgccgacacctccggcgac cacgtgtcgctggccggcctgccgcgcgtcgtcgacatcgacgtcccgggccgggccgtgtccctgtccgcgggcctgcgc ttcggcgagttcgccgccgagctgcacgcccgcgcctggccctggccaacctgggctccctgccgcacatctccgtggcg ggcgcggtcgccaccggcacccacggctccggcgtcggcaaccgctccctggcgggcgccgtccgcgccctgtccctggt caccgccgacgcgagaccgcaccctgcgccgcaccgacgaggacttcgccggcgccgtcgtgtccctgggcgccctg ggcgtcgtcacctccctggagctggacctggtcccggccttcgaggtccgccagtgggtctacgaggacctgcccgaggcc accctggccgcccgcttcgacgaggtcatgtccgccgcctaccgtgtccgtgttcaccgactggcgcccgggccggtcg gccaggtctggctgaagcagcgcgtcggcgacgagggcgcccgctccgtcatgccggccgagtggctgggcgcccgcct ggccgacggccgcgccacccggtccccggcatgcccgccggcaactgcaccgcccagcagggcgtcccgggcccgt ggcacgagcgcctgccgcacttccgcatggagttcaccccgtccaacggcgacgagctgcagtccgagtacttcgtcgccc gcgcggacgccgtcgcggcctacgaggcgctggcccgcctgcgcgaccgcatcgccccggtcctgcaggtctccgagct gcgcaccgtcgccgccgacgacctgtggctgtccccggcccacggccgcgactccgtcgccttccacttcacctgggtccc ggacgccgccgcgtcgccccggtcgccggcgccatcgaggaggccctggccccgttcggcgcccgcccgcactgggg caaggtgttctccaccgccccgaggtcctgcgcaccctgtacccgcgctacgccgacttcgaggagctggtcggccgcca cgaccccgagggcaccttccgcaacgccttcctcgaccgctacttccgccgctgaggatccgcgagcggatcggctgacc ggagcggggaggaggacgggcggccggcggaaaagtccgccggtccgctgaatcgctccccgggcacggacgtggc agtatcagcgccatgtccggcatatcccagccctccgcatgcaagcttggcactggccgtcgttttacaacgtcgtgactggg aaaaccctggcgttacccaacttaatcgccttgcagcacatcccccttcgccagctggcgtaatagcgaagaggcccgca ccgatcgcccttcccaacagttgcgcagcctgaatggcgaatggcgcctgatgcggtattttctccttacgcatctgtgcggatt tcacaccgcatatggtgcactctcagtacaatctgctctgatgccgcatagttaagccagccccgacacccgccaacacccg ctgacgcgccctgacgggcttgtctgctcccggcatccgcttacagacaagctgtgaccgtctccgggagctgcatgtgtcaa gaggttttcaccgtcatcaccgaaacgcgcgagacgaaagggcctcgtgatacgcctatttttataggttaatgtcatgataat aatggtttcttagacgtcaggtggcacttttcggggaaatgtgcgcggaaccccctatttgtttatttttctaaatacattcaaatatgt atccgctcatgagacaataaccctgataaatgcttcaataatattgaaaaaggaagagtatgagtattcaacatttccgtgtcg cccttattccctttttttgcggcattttgccttcctgttttttgctcacccagaaacgctggtgaaagtaaaagatgctgaagatcagttg ggtgcacgagtgggttacatcgaactggatctcaacagcggtaagatccttgagagttttcgccccgaagaacgttttccaat gatgagcacttttaaagttctgctatgtggcgcggtattatcccgtattgacgccgggcaagagcaactcggtcgccgcataca ctattctcagaatgacttggttgagtactcaccagtcacagaaaagcatcttacggatggcatgacagtaagagaattatgca gtgctgccataaccatgagtgataacactgcggccaacttacttctgacaacgatcggaggaccgaaggagctaaccgcttt tttgcacaacatgggggatcatgtaactcgccttgatcgttgggaaccggagctgaatgaagccataccaaacgacgagcg tgacaccacgatgcctgtagcaatggcaacaacgttgcgcaaactattaactggcgaactacttactctagcttcccggcaa caattaatagactggatggaggcggataaagttgcaggaccacttctgcgctcggcccttccggctggctggtttattgctgat aaatctggagccggtgagcgtgggtctcgcggtatcattgcagcactggggccagatggtaagccctcccgtatcgtagttat -continued

```
ctacacgacggggagtcaggcaactatggatgaacgaaatagacagatcgctgagataggtgcctcactgattaagcattg gtaactgtcagaccaagtttactcatatatactttagattgatttaaaacttcatttttaatttaaaaggatctaggtgaagatccttttt gataatctcatgaccaaaatcccttaacgtgagttttcgttccactgagcgtcagaccccgtagaaaagatcaaaggatcttctt gagatcctttttttctgcgcgtaatctgctgcttgcaaacaaaaaaaccaccgctaccagcggtggtttgtttgccggatcaaga gctaccaactctttttccgaaggtaactggcttcagcagagcgcagataccaaatactgtccttctagtgtagccgtagttaggc caccacttcaagaactctgtagcaccgcctacatacctcgctctgctaatcctgttaccagtggctgctgccagtggcgataag tcgtgtcttaccgggttggactcaagacgatagttaccggataaggcgcagcggtcgggctgaacggggggttcgtgcaca cagcccagcttggagcgaacgacctacaccgaactgagatacctacagcgtgagctatgagaaagcgccacgcttcccg aagggagaaaggcggacaggtatccggtaagcggcagggtcggaacaggagagcgcacgagggagcttccagggg gaaacgcctggtatctttatagtcctgtcgggtttcgccacctctgacttgagcgtcgatttttgtgatgctcgtcaggggcgg agcctatggaaaaacgccagcaacgcggcctttttacggttcctggccttttgctggccttttgctcacatgttctttcctgcgttatc ccctgattctgtggataaccgtattaccgcctttgagtgagctgataccgctcgccgcagccgaacgaccgagcgcagcgag tcagtgagcgaggaagcggaagagcgcccaatacgcaaaccgcctctccccgcgcgttggccgattcattaatgcagctg gcacgacaggtttcccgactggaaagcgggcagtgagcgcaacgcaattaatgtgagttagctcactcattaggcacccca ggctttacactttatgcttccggctcgtatgttgtgtggaattgtgagcggataacaatttcacacaggaaacagctatgaccatg attacgccgaattcggggcatgcctgcaggagtgggggaggcacgatggccgctttggtcgacctcaacgagacgatgaag ccgtggaacgacaccaccccggcggccctgctggaccacacccggcactacaccttcgacgtctgatcatcactgacgaa tcgaggtcgaggaaccgagcgtccgaggaacacaggcgcttatcggttggccgcgagattcctgtcgatcctctcgtgcag cgcgattccgaggg aaacggaaacgttgagagactcggtctggctcatcatggggatggaaaccgaggcggaagacgc ctcctcgaacaggtcggaaggcccaccctttttcgctgccgaacagcaaggccagccgatccggattgtccccgagttccttc acggaaatgtcgccatccgccttgagcgtcatcagctgcataccgctgtcccgaatgaaggcgatggcctcctcgcgaccg gagagaacgacgggaagggagaagacgtaacctcggctggcccttttggagacgccggtccgcgatgctggtgatgtcac tgtcgaccaggatgatccccgacgctccgagcgcgagcgacgtgcgtactatcgcgccgatgttcccgacgatcttcacccc gtcgagaacgacgacgtccccacgccggctcgcgatatcgccgaacctggccgggcgagggacgcgggcgatgccga atgtcttggccttccgctcccccttgaacaactggttgacgatcgaggagtcgatgaggcggaccggtatgttctgccgcccgc acagatccagcaactcagatggaaaaggactgctgtcgctgccgtagacctcgatgaactccaccccggccgcgatgctgt gcatgagggggctcgacgtcctcgatcaacgttgtctttatgttggatcgcgacggcttggtgacatcgatgatccgctgcaccg cgggatcggacggatttgcgatggtgtccaactcagtcatggtcgtcctaccggctgctgtgttcagtgacgcgattcctggggt gtgacacccctacgcgacgatggcggatggctgccctgaccggcaatcaccaacgcaaggggaagtcgtcgctctctggca aagctccccgctcttccccgtccgggacccgcgcggtcgatccccgcatatgaagtattcgccttgatcagtcccggtggacg cgccagcggcccgccggagcgacggactccccgacctcgatcgtgtcgccctgagcgtccacgtagacgttgcgtgaga gcaggactgggccgccgccgaccgcaccgccctcaccaccgaccgcgaccgcgccatggccgccgccgacggcctgg tcgccgccgccgcccgcggttcggcgcctgacccgaccaaccccgcggggcgccggcacttcgtgctggcgcccgc ccccacccaccaggagaccgaccatgaccgacttcgacggacgcctgaccgaggggaccgtgaacctggtccaggacc ccaacggcggtggctggtccgccactgcgctgagcccggttgcgactgggccgacttcgccggaccgctcggcttccagg gcctcgtggccatcgctcgccgacacacgcactgaccgcacgtcaaagcccgccggataccggcggggctctcttcgg ccctccaagtcacaccagcccaaggggcgtcggagtggcggagggaacctctggcccgattggtgccaggattccca ccagaccaaagagcaacgggccggacttcgcacctccgacccgtccgctcccagactcgcgcccttagccgggcgag acaggaacgttgctcgtgcccagagtacggagcgatgccgaggcattgccagatcggcccgccgggccccgctgccact gcgggaccgcaattgcccacacaccgggcaaacggccgcgtatctactgctcagaccgctgccggatggcagcgaagc
```

-continued

```
gggcgatcgcgcgtgtgacgcgagatgccgcccgaggcaaaagcgaacaccttgggaaagaaacaacagagtttcccg
caccccctccgacctgcggtttctccggacggggtgg atggggagagcccgagaggcgacagcctctgggaagtaggaag
cacgtcgcggaccgaggctgcccgactgcggaaagccgcccggtacagccgccgccggacgctgtggcggatcagcg
gggacgccgcgtgcaagggctgcggccgcgccctgatggaccctgcctccgcgtgatcgtcgcccagacggcggccg
gaacgtccgtggtcctgggcctgatgcggtgcgggcggatctggctctgcccggtctgcgccgccacgatccggcacaagc
gggccgaggagatcaccgccgccgtggtcgagtggatcaagcgcgggggggaccgcctacctggtcaccttcacggcccg
ccatgggcacacggaccggctcgcggacctcatggacgccctccagggcacccggaagacgccggacagcccccggc
ggccgggcgcctaccagcgactgatcacgggcggcacgtgggccggacgccgggccaaggacgggcaccgggccgc
cgaccgcgagggcatccgagaccggatcgggtacgtcggcatgatccgcgcgaccgaagtcaccgtggggcagatcaa
cggctggcaccgcacatccacgcgatcgtcctggtcggcggccggaccgaggggggagcggtccgcgaagcagatcgt
cgccaccttcgagccgaccggcgccgcgctcgacgagtggcaggggcactggcggtccgtgtggaccgccgccctgcgc
aaggtcaaccccgccttcacgcccgacgaccggcacggcgtcgacttcaagcggctggagaccgagcgcgacgccaac
gacctcgccgagtacatcgccaagacccaggacgggaaggcgcccgccctcgaactcgcccgcgccgacctcaagac
ggcgaccggcgggaacgtcgcccgttcgaactcctcggacggatcggggacctgaccggcggcatgaccgaggacga
cgccgccggggtcggctcgctggagtggaacctctcgcgctggcacgagtacgagcgggcaacccggggacgccgggc
catcgaatggacccgctacctgcggcagatgctcgggctcgacggcggcgacaccgaggccgacgacctcgatctgctc
ctggcggccgacgccgacggcggggagctgcgggccggggtcgccgtgaccgaggacggatggcacgcggtcacccg
ccgcgccctcgacctcgaggcgacccgggccgccgaaggcaaggacggcaacgaggattcggcggccgtgggcgaa
cgggtgcgggaggtcctggcgctggccgacgcggccgacacagtggtggtgctcacggcgggggaggtggccgaggcg
tacgccgacatgctcgccgccctcgcccagcgccgcgaggaagcaactgcacgccgacggcgagagcaggacgacg
accaggacgacgacgccgacgaccgccaggagcgggccgccggcacatcgcccggctcgcaagtgggcccacttcg
cactaactcgctccccccgccgtacgtcatcccggtgacgtacggcggggtcggtgacgtacgcggcgacggcggccg
gggtcgaagccgcgggagtaatcctgggattactcgcccggggtcggccccgccggcacttcgtgcaggcggtacctcgc
gcccgactcgcctcgctacgagacgtgccgcgtacggtcgtcggccatgagcaccaccaccccccagggacgccgacgg
cgcgaagctctgcgcctggtgcggctcggagatcaagcaatccggcgtcggccggagccgggactactgccgccgctcct
gccgccagcgggcgtacgaggcccggcgccagcgcgaggcgatcgtgtccgccgtggcgtcggcagtcgctcgccgag
atacgtcacgtgacgaaatgcagcagccttccattccgtcacgtgacgaaactcgggccgcaggtcagagcacggttccgc
ccgctccggccctgccggaccccccggctgcagctcgcccggccgccggtcccccctgccgtccggcccgtcccagaggca
gcgtcggcggctcctgcctcccccgcccggcgccgaccgggaccccgcaaaccccttgatccgctgtcgggggtgatcact
acggtgggtgccgaagtgatcacggggaggactgatgcaccaccaggaccgggaccaggaccaggcgttagcggcag
tgctggccgcactgctcctggtcggcgggacgctgatcgtgcgggagctcctgggcctgtggcccgccgtggcggtcggcat
ggcgcccgccctcgccctctacggaggcccgcccgcggcccgccggatagccgtcgcggtcgaggtccgccggttccgc
cggcatcttgcccaccacgatcgggcagccggatgaccggccacgacggagccgcacggctgaccagctcgacggccg
ccacctcatcgcggcagcaggtgctccccagcaacccacgacggggctcagggtcgcctcacgcggctcagcaccgcg
acggcggggtacggcgctccgggaggctgacaggcgctcagacggccgcgtagggccgcgagtcccccacccctccc
cgctgccctgtcggcgagcacaacggcgatgcccgcagtcggcggagcaggcgccacgtaaaccgcccaccgatgccg
cccccgtcgtgtgcgcgggccggtcggcggccgggccggagcggggcgaagacaggagcgtcggccgggccgtgggc
cggggccgcgcggcccgctcgcgggccgccttgatgacgtagggaaagttgtaccgcaaaaaacgcagcctgaactagtt
gcgatcct
```

Two oligos (SEQ ID NO:18 and SEQ ID NO:19) were obtained from Invitrogen.

(SEQ ID NO: 18)
GCGCTAGCCGGCCCCCCGGCACAGGCCATGACCCCGGCCGAGAAGAACT
GGG (SEQ ID NO: 19)
CAGGAAACAGCTATGAC

The primers were used in PCR to amplify sorbitol oxidase gene and to fuse the sorbitol oxidase gene to the celA signal sequence. The PCR reaction mixture containing DNA, dNTPs, primer and 4% DMSO in 1× buffer was heated to 98° C. for 4 minutes to denature the DNA templates. Herculase® II enzyme (Stratagene) was added to the tube and PCR reaction was performed in 30 cycles of 98° C. for 30 seconds, 62° C. for 30 seconds and 72° C. for 1 minute and 8 seconds. The final extension at 72° C. was done for 5 minutes and the reaction was chilled to 4° C.

The resulting PCR fragment contained a portion of the celA signal sequence, the sorbitol oxidase gene, and a portion of vector sequence containing two restriction enzyme sites (SEQ ID NO:20).

(SEQ ID NO: 20)
GCGCTAGCCGGCCCCCCGGCACAGGCCATGACCCCGGCCGAGAAGAACT
GGGCCGGCAACATCACCTTCGGCGCCAAGCGCCTGTGCGTCCCGCGCTC
CGTCCGCGAGCTGCGCGAGACCGTGGCCGCCTCCGGCGCCGTGCGCCCG
CTGGGCACCCGCCACTCGTTCAACACCGTCGCCGACACCTCCGGCGACC
ACGTGTCGCTGGCCGGCCTGCCGCGCGTCGTCGACATCGACGTCCCGGG
CCGGGCCGTGTCCCTGTCCGCCGGCCTGCGCTTCGGCGAGTTCGCCGCC
GAGCTGCACGCCCGCGGCCTGGCCCTGGCCAACCTGGGCTCCCTGCCGC
ACATCTCCGTGGCGGGCGCGGTCGCCACCGGCACCCACGGCTCCGGCGT
CGGCAACCGCTCCCTGGCGGGCGCCGTCCGCGCCCTGTCCCTGGTCACC
GCCGACGGCGAGACCCGCACCCTGCGCCGCACCGACGAGGACTTCGCCG

GCGCCGTCGTGTCCCTGGGCGCCCTGGGCGTCGTCACCTCCCTGGAGCT
GGACCTGGTCCCGGCCTTCGAGGTCCGCCAGTGGGTCTACGAGGACCTG
CCCGAGGCCACCCTGGCCGCCCGCTTCGACGAGGTCATGTCCGCCGCCT
ACTCCGTGTCCGTGTTCACCGACTGGCGCCCGGGCCCGGTCGGCCAGGT
CTGGCTGAAGCAGCGCGTCGGCGACGAGGGCGCCCGCTCCGTCATGCCG
GCCGAGTGGCTGGGCGCCCGCCTGGCCGACGGCCCGCGCCACCCGGTCC
CCGGCATGCCCGCCGGCAACTGCACCGCCCAGCAGGGCGTCCCGGGCCC
GTGGCACGAGCGCCTGCCCGCACTTCCGCATGGAGTTCACCCCGTCCAAC
GGCGACGAGCTGCAGTCCGAGTACTTCGTCGCCCGCGCGGACGCCGTCG
CGGCCTACGAGGCGCTGGCCCGCCTGCGCGACCGCATCGCCCCGGTCCT
GCAGGTCTCCGAGCTGCGCACCGTCGCCGCCGACGACCTGTGGCTGTCC
CCGGCCCACGGCCGCGACTCCGTCGCCTTCCACTTCACCTGGGTCCCGG
ACGCCGCCGCCGTCGCCCCGGTCGCCGGCGCCATCGAGGAGGCCCTGGC
CCCGTTCGGCGCCCGCCCGCACTGGGGCAAGGTGTTCTCCACCGCCCCC
GAGGTCCTGCGCACCCTGTACCCGCGCTACGCCGACTTCGAGGAGCTGG
TCGGCCGCCACGACCCCGAGGGCACCTTCCGCAACGCCTTCCTCGACCG
CTACTTCCGCCGCTGAGGATCCGAGCTCCAGCTTTTGTTCCCTTTAGTG
AGGGTTAATTGCGCGCTTGGCGTAATCATGGTCATAGCTGTTTCCTG

Figure 2:
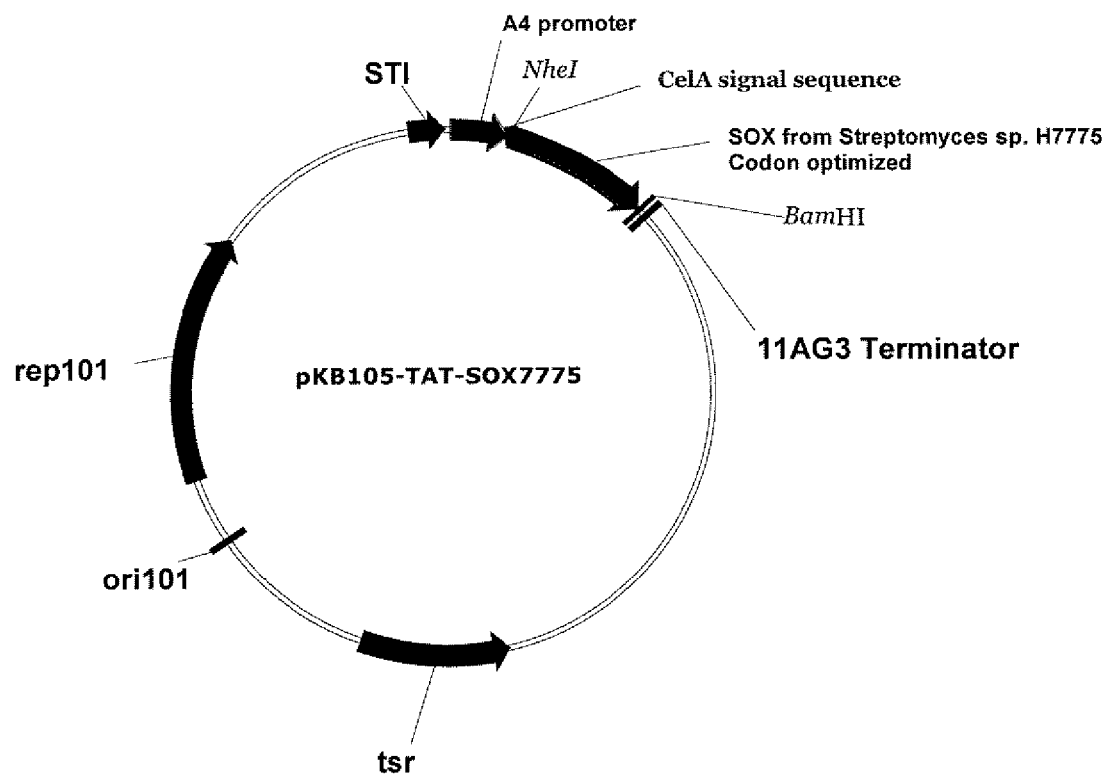
FIG. 2 provides a map of expression plasmid pKB105-CelA-SOx-7775 (SEQ ID NO:30).

The PCR fragment was digested with restriction enzymes NheI and BamHI to remove the vector sequence portion. The resulting fragment was then cloned to expression vector pKB105 to generate the plasmid "pKB105-CelA-SOx7775" (See, FIG. 2; SEQ ID NO: 30). The expression plasmid was transformed into *Streptomyces lividans* strain g3s3 and three transformants were selected and grown in TS medium for 2-3 days in the presence of 50 ug/ml thiostrepton at 30° C. Cells were then transferred to a production medium free of antibiotics and growth was continued for another three days. Then, 1 ml sample was transferred to each of two new culture tubes and cells were removed and the enzyme was purified as described in Example 5.

pKB105-celA-SOx7775 (9489 bps):

(SEQ ID NO: 30)
ctagagatcgaacttcatgttcgagttcttgttcacgtagaagccggagatgtgagaggtgatctggaactgctcaccctcgttg
gtggtgacctggaggtaaagcaagtgacccttctggcggaggtggtaaggaacggggttccacggggagagagagatgg
ccttgacggtcttgggaaggggagcttcggcgcggggaggatggtcttgagagaggggagctagtaatgtcgtacttgg
acagggagtgctccttctccgacgcatcagccacctcagcggagatggcatcgtgcagagacagaccccccggaggtaac
catgggctttgggagcgctcccatcgcgttgtgtccgcttcgcacgaggaggaacgctttgaaacgccttttggccctgctcgc
gaccggcgtgtcgatcgtcggcctgactgcgctagccggcccccggcacaggccatgaccccggccgagaagaactg
ggccggcaacatcaccttcggcgccaagcgcctgtgcgtcccgcgctccgtccgcgagctgcgcgagaccgtggccgcct
ccggcgccgtgcgcccgctgggcacccgccactcgttcaacaccgtcgccgacacctccggcgaccacgtgtcgctggcc
ggcctgccgcgcgtcgtcgacatcgacgtcccgggccgggccgtgtccctgtccgccggcctgcgcttcggcgagttcgcc
gccgagctgcacgcccgcggcctggccctggccaacctgggctccctgccgcacatctccgtggcgggcgcggtcgccac
cggcacccacggctccggcgtcggcaaccgctccctggcgggcgccgtccgcgccctgtccctggtcaccgccgacggc
gagacccgcaccctgcgccgcaccgacgaggacttcgccggcgccgtcgtgtccctgggcgccctgggcgtcgtcacctc -continued

```
cctggagctggacctggtcccggccttcgaggtccgccagtgggtctacgaggacctgcccgaggccaccctggccgccc
gcttcgacgaggtcatgtccgccgcctaccccgtgtccgtgttcaccg actggcgcccgggcccggtcggccaggtctggctg
aagcagcgcgtcggcgacgagggcgcccgctccgtcatgccggccgagtggctgggcgcccgcctggccgacggcccg
cgccacccggtccccggcatgcccgccggcaactgcaccgcccagcagggcgtcccgggcccgtggcacgagcgcctg
ccgcacttccgcatggagttcaccccgtccaacggcgacgagctgcagtccgagtacttcgtcgcccgcgcggacgccgtc
gcggcctacgaggcgctggcccgcctgcgcgaccgcatcgccccggtcctgcaggtctccgagctgcgcaccgtcgccgc
cgacgacctgtggctgtccccggcccacggccgcgactccgtcgccttccacttcacctgggtcccggacgccgccgccgt
cgccccggtcgccggcgccatcgaggaggccctggcccccgttcggcgcccgcccgcactggggcaaggtgttctccacc
gccccgaggtcctgcgcacccgtacccgcgctacgccgacttcgaggagctggtcggccgccacgaccccgagggca
ccttccgcaacgccttcctcgaccgctacttccgccgctgaggatccgcgagcggatcggctgaccggagcggggaggag
gacgggcggccggcggaaaagtccgccggtccgctgaatcgctccccgggcacggacgtggcagtatcagcgccatgtc
cggcatatcccagcccctccgcatgcaagcttggcactggccgtcgttttacaacgtcgtgactgggaaaaccctggcgttacc
caacttaatcgccttgcagcacatccccctttcgccagctggcgtaatagcgaagaggccccgcaccgatcgcccttcccaac
agttgcgcagcctgaatggcgaatggcgcctgatgcggtattttctccttacgcatctgtgcggtatttcacaccgcatatggtgc
actctcagtacaatctgctctgatgccgcatagttaagccagccccgacacccgccaacacccgctgacgcgccctgacgg
gcttgtctgctcccggcatccgcttacagacaagctgtgaccgtctccgggagctgcatgtgtcaagaggttttcaccgtcatca
ccgaaacgcgcgagacgaaagggcctcgtgatacgcctatttttataggttaatgtcatgataataatggtttcttagacgtcag
gtggcacttttcggggaaatgtgcgcggaacccctatttgtttatttttctaaatacattcaaatatgtatccgctcatgagacaata
accctgataaatgcttcaataatattgaaaaaggaagagtatgagtattcaacatttccgtgtcgcccttattcccttttttgcggc
attttgccttcctgtttttgctcacccagaaacgctggtgaaagtaaaagatgctgaagatcagttgggtgcacgagtgggttac
atcgaactggatctcaacagcggtaagatccttgagagttttcgccccgaagaacgttttccaatgatgagcacttttaaagttc
tgctatgtggcgcggtattatcccgtattgacgccgggcaagagcaactcggtcgccgcatacactattctcagaatgacttgg
ttgagtactcaccagtcacagaaaagcatcttacgg atggcatgacagtaagagaattatgcagtgctgccataaccatgag
tgataacactgcgccaacttacttctgacaacgatcggaggaccgaaggagctaaccgcttttttgcacaacatgggggatc
atgtaactcgccttgatcgttgggaaccggagctgaatgaagccataccaaacgacgagcgtgacaccacgatgcctgtag
caatggcaacaacgttgcgcaaactattaactggcgaactacttactctagcttcccggcaacaattaatagactggatgga
ggcggataaagttgcaggaccacttctgcgctcggcccttccggctggctggtttattgctgataaatctggagccggtgagcg
tgggtctcgcggtatcattgcagcactggggccagatggtaagccctcccgtatcgtagttatctacacgacggggagtcagg
caactatggatgaacgaaatagacagatcgctgagataggtgcctcactgattaagcattggtaactgtcagaccaagtttac
tcatatatactttagattgatttaaaacttcatttttaatttaaaaggatctaggtgaagatcctttttgataatctcatgaccaaaatc
ccttaacgtgagttttcgttccactgagcgtcagaccccgtagaaaagatcaaaggatcttcttgagatcctttttttctgcgcgta
atctgctgcttgcaaacaaaaaaaccaccgctaccagcggtggtttgtttgccggatcaagagctaccaactctttttccgaag
gtaactggcttcagcagagcgcagataccaaatactgtccttctagtgtagccgtagttaggccaccacttcaagaactctgta
gcaccgcctacatacctcgctctgctaatcctgttaccagtggctgctgccagtggcgataagtcgtgtcttaccgggttggact
caagacgatagttaccggataaggcgcagcggtcgggctgaacggggggttcgtgcacacagcccagcttggagcgaa
cgacctacaccgaactgagatacctacagcgtgagctatgagaaagcgccacgcttcccgaagggagaaaggcggaca
ggtatccggtaagcggcagggtcggaacaggagagcgcacgagggagcttccaggggaaacgcctggtatctttatagt
cctgtcgggtttcgccacctctgacttgagcgtcgatttttgtgatgctcgtcagggggggcggagcctatggaaaaacgccagc
aacgcggcctttttacggttcctggccttttgctggccttttgctcacatgttctttcctgcgttatcccctgattctgtggataaccgtat
taccgcctttgagtgagctgataccgctcgccgcagccgaacgaccgagcgcagcgagtcagtgagcgaggaagcgga
agagcgcccaatacgcaaaccgcctctccccgcgcgttggccgattcattaatgcagctggcacgacaggtttcccgactg
```

-continued

```
gaaagcgggcagtgagcgcaacgcaattaatgtgagttagctcactcattaggcacccaggctttacactttatgcttccgg ctcgtatgttgtgtgg aattgtgagcggataacaatttcacacaggaaacagctatgaccatgattacgccgaattcggggcat gcctgcaggagtggggaggcacgatggccgctttggtcgacctcaacgagacgatgaagccgtggaacgacaccaccc cggcggccctgctggaccacaccggcactacaccttcgacgtctgatcatcactgacgaatcgaggtcgaggaaccgag cgtccgaggaacacaggcgcttatcggttggccgcgagattcctgtcgatcctctcgtgcagcgcgattccgagggaaacg gaaacgttg agagactcggtctggctcatcatggggatggaaaccgaggcggaagacgcctcctcgaacaggtcggaag gcccaccctttttcgctgccgaacagcaaggccagccgatccggattgtcccgagttccttcacggaaatgtcgccatccgc cttgagcgtcatcagctgcataccgctgtcccgaatgaaggcgatggcctcctcgcgaccggagagaacgacgggaagg gagaagacgtaacctcggctggccctttggagacgccggtccgcgatgctggtgatgtcactgtcgaccaggatgatcccc gacgctccgagcgcgagcgacgtgcgtactatcgcgccgatgttcccgacgatcttcaccccgtcgagaacgacgacgtc cccacgccggctcgcgatatcgccgaacctggccgggcgagggacgcgggcgatgccgaatgtcttggccttccgctccc ccttgaacaactggttgacgatcgaggagtcgatgaggcggaccggtatgttctgccgcccgcacagatccagcaactcag atggaaaaggactgctgtcgctgccgtagacctcgatgaactccaccccggccgcgatgctgtgcatgaggggctcgacgt cctcgatcaacgttgtctttatgttggatcgcgacggcttggtg acatcgatgatccgctgcaccgcgggatcggacggatttgc gatggtgtccaactcagtcatggtcgtcctaccggctgctgtgttcagtgacgcgattcctggggtgtgacaccctacgcgacg atggcggatggctgccctgaccggcaatcaccaacgcaaggggaagtcgtcgctctctggcaaagctccccgctcttcccc gtccgggacccgcgcggtcgatccccgcatatgaagtattcgccttgatcagtcccggtggacgcgccagcggcccgccg gagcgacggactccccgacctcgatcgtgtcgccctgagcgtccacgtagacgttgcgtgagagcaggactgggccgccg ccgaccgcaccgccctcaccaccgaccgcgaccgcgccatggccgccgccgacggcctggtcgccgccgccgcccgc cggttcggcgcctgacccgaccaaccccgcggggcgccggcacttcgtgctggcgccccgccccaccccaccaggag accgaccatgaccgacttcgacggacgcctgaccgaggggaccgtgaacctggtccaggaccccaacggcggtggctg gtccgcccactgcgctgagcccggttgcgactgggccgacttcgccggaccgctcggcttccagggcctcgtggccatcgct cgccgacacacgcactgaccgcacgtcaaagcccgccggatacccggcggggctctcttcggccctccaagtcacacc agccccaaggggcgtcgggagtggcggagggaacctctggcccgattggtgccaggattcccaccagaccaaagagca acgggccggacttcgcacctccgacccgtccgctcccagactcgcgccccttagccgggcgagacaggaacgttgctcgt gcccagagtacggagcgatgccgaggcattgccagatcggcccgccgggccccgctgccactgcgggaccgcaattgc ccacacaccgggcaaacggccgcgtatctactgctcagaccgctgccggatggcagcgaagcgggcgatcgcgcgtgtg acgcgagatgccgcccgaggcaaaagcgaacaccttgggaaagaaacaacagagtttcccgcacccctccgacctgcg gtttctccggacggggtggatggggagagcccgagaggcgacagcctctgggaagtaggaagcacgtcgcggaccgag gctgcccgactgcggaaagccgcccggtacagccgccgccggacgctgtggcggatcagcggggacgccgcgtgcaa gggctgcggccgcgccctgatggaccctgcctccggcgtgatcgtcgcccagacggcggccgaacgtccgtggtcctgg gcctgatgcggtgcgggcggatctggctctgcccggtctgcgccgccacgatccggcacaagcgggccgaggagatcac cgccgccgtggtcgagtggatcaagcgcgggggaccgcctacctggtcaccttcacggcccgccatgggcacacggac cggctcgcggacctcatggacgccctccagggcacccggaagacgccggacagccccggcggccgggcgcctacca gcgactgatcacgggcggcacgtgggccggacgccgggccaaggacgggcaccggccgccgaccgcgagggcatc cgagaccggatcgggtacgtcggcatgatccgcgcgaccgaagtcaccgtggggcagatcaacggctggcacccgcac atccacgcgatcgtcctggtcggcggccgg accgaggggagcggtccgcgaagcagatcgtcgccaccttcgagccga ccggcgccgcgctcgacgagtggcaggggcactggcggtccgtgtggaccgccgccctgcgcaaggtcaaccccgcctt cacgcccgacgaccggcacggcgtcgacttcaagcggctggagaccgagcgcgacgccaacgacctcgccgagtaca tcgccaagacccaggacgggaaggcgcccgccctcgaactcgcccgcgccgacctcaagacggcgaccggcgggaa
```

-continued

```
cgtcgcccgttcgaactcctcggacggatcggggacctgaccggcggcatgaccgaggacgacgccgccggggtcgg ctcgctggagtggaacctctcgcgctggcacgagtacgagcgggcaacccggggacgccgggccatcgaatggacccg ctacctgcggcagatgctcgggctcgacggcggcgacaccgaggccgacgacctcgatctgctcctggcggccgacgcc gacggcggggagctgcgggccggggtcgccgtgaccgaggacggatggcacgcggtcacccgccgcgccctcgacct cgaggcgacccgggccgccgaaggcaaggacggcaacgaggattcggcggccgtgggcgaacgggtgcgggaggtc ctggcgctggccgacgcggccgacacagtggtggtgctcacggcgggggaggtggccgaggcgtacgccgacatgctc gccgccctcgcccagcgccgcgaggaagcaactgcacgccgacggcgagagcaggacgacgaccaggacgacgac gccgacgaccgccaggagcgggccgcccggcacatcgcccggctcgcaagtgggcccacttcgcactaactcgctcccc cccgccgtacgtcatcccggtgacgtacggcggggtcggtgacgtacgcggcgacggcggccgggggtcgaagccgcg ggagtaatcctgggattactcgcccggggtcggccccgccggcacttcgtgcaggcggtacctcgcgcccgactcgcctcg ctacgagacgtgccgcgtacggtcgtcggccatgagcaccaccaccccccaggacgccgacggcgcgaagctctgcgc ctggtgcggctcggagatcaagcaatccggcgtcggccgg agccgggactactgccgccgctcctgccgccagcgggcg tacgaggcccggcgccagcgcgaggcgatcgtgtccgccgtggcgtcggcagtcgctcgccgagatacgtcacgtgacg aaatgcagcagccttccattccgtcacgtgacgaaactcgggccgcaggtcagagcacggttccgcccgctccggccctgc cggaccccggctgcagctcgcccggccgccggtcccctgccgtccggcccgtcccagaggcagcgtcggcggctcct gcctccccgcccggcgccgaccgggacccgcaaacccttgatccgctgtcggggtgatcactacggtgggtgccgaa gtgatcacggggaggactgatgcaccaccaggaccgggaccaggaccaggcgttagcggcagtgctggccgcactgct cctggtcggcgggacgctgatcgtgcgggagctcctgggcctgtggcccgccgtggcggtcggcatggcgcccgccctcg ccctctacgaggcccgcccgcggcccgccggatagccgtcgcggtcgaggtccgccggttccgccggcatcttgcccac cacgatcgggcagccggatgaccggccacgacggagccgcacggctgaccagctcgacggccgccacctcatcgcgg cagcaggtgctccccagcaacccacgacgggctcagggtcgcctcacgcggctcagcaccgcgacggcgggggtac ggcgctccgggaggctgacaggcgctcagacggccgcgtagggccgcgagtcccccacccctccccgctgccctgtcgg cgagcacaacggcgatgcccgcagtcggcggagcaggcgccacgtaaaccgcccaccgatgccgccccccgtcgtgtgc gcgggccggtcggcggccgggccggagcggggcgaagacaggagcgtcggccgggccgtgggccgggccgcgcgg cccgctcgcgggccgccttgatgacgtagggaaagttgtaccgcaaaaaacgcagcctgaactagttgcgatcct
```

Example 2

Identification of Genes with Sequence Identity/Similarity to the *Streptomyces* sp. H7775 SOx Gene In this Example, experiments conducted to identify genes with sequence identity/similarity with the *Streptomyces* sp. H-7775 sorbitol oxidase gene are described. In these experiments, homologues encoding polyol oxidases (e.g., sorbitol and xylitol oxidase) were identified using the primary sequences of two functionally characterized polyol oxidases, namely *Streptomyces* sp. H-7775 sorbitol oxidase described herein and the *Streptomyces* sp. IKD472/FERM P-14339 xylitol oxidase as queries in BLAST analyses on the non-redundant (nr) protein database of the National Center for Biotechnology Information. Putative polyol oxidases were identified from different species of *Streptomyces, Acidothermus, Arthrobacter, Brevibacterium, Frankia, Nocardia, Janibacter, Marinobacter, Burkholderia, Paracoccus, Chromabacterium, Thermobifida, Xanthomonas, Pseudomonas, Corynebacterium* and *Bacillus*. In addition, the UniProtKB/TrEMBL/Swiss-Prot databases were also searched for genes which function as sorbitol or xylitol oxidases. In addition to the *Streptomyces* sp. IKD472/FERM P-14339 xylitol oxidase, the following were identified as xylitol oxidases in these searches: XYOA STRCO (Q9ZBU1) from *Streptomyces coelicolor*, XYOA STRSI (Q9KX73) from *Streptomyces* sp. strain IKD472/FERM P-14339; Q2E2H5 ACICE from *Acidothermus cellulolyticus* 11B; and Q82LC0 STRAW from *Streptomyces avermitilis*.

In additional experiments, the genes encoding polyol oxidases (e.g., sorbitol oxidase/xylito I oxidase) were obtained by utilizing sequenced genomes to generate and screen genomic libraries of culturable organisms. In additional embodiments, novel polyol oxidase genes are obtained from microbes that are unculturable by generating and screening metagenomic libraries.

One example of such a metagenome is the complex microbial consortia derived from different soil sources. The microbiome metagenome database (JGI-DOE, USA) was searched for sequences with sequence identity to the SOx gene using the Function search: Genes in EC:1.1.3.41—Xylitol oxidase, resulted in the identification of five FAD/FMN-containing dehydrogenases and one probable xylitol oxidase. The following table (Table 1) provides various polyol oxidases identified in searches in which the *Streptomyces* sp. H7775 SOx gene was used to query the Quick BLAST P.

TABLE 1

Polyol Oxidases

| UniProt Accession Numbers | Protein Name | Source Species Name |
|---|---|---|
| P97011 | Sorbitol oxidase [SOx] SEQ ID NO: 1 | Streptomyces sp |
| Q9ZBU1 | Probable xylitol oxidase (EC 1.1.3.41) SEQ ID NO: 9 | Streptomyces coelicolor |
| Q2E2H5 | Putative xylitol oxidase SEQ ID NO: 6 | Acidothermus cellulolyticus 11B |
| Q82LC0 | Putative xylitol oxidase SEQ ID NO: 8 | Streptomyces avermitilis |
| Q4NJL0 | FAD linked oxidase N-terminal SEQ ID NO: 12 | Arthrobacter sp. FB24 |
| Q9KX73 | Xylitol oxidase (EC 1.1.3.41) SEQ ID NO: 10 | Streptomyces sp. IKD472 |
| Q412H8 | FAD linked oxidase, N-terminal | Kineococcus radiotolerans SRS30216 |

Example 3

Expression of the *Streptomyces lividans* Sorbitol Oxidase Gene in *Streptomyces lividans* Strain g3s3

In this Example, experiments conducted to express the *S. lividans* sorbitol oxidase gene in *S. lividans* are described. Based on in silico analyses, two other *Streptomyces* species (*S. coelicolor* and *S. avermitilis*) were identified as having putative xylitol oxidase genes. The locus containing the *Streptomyces coelicolor* putative XOx gene (SCO6147) sequence was retrieved from the sequence database. The corresponding *S. lividans* gene was isolated using primers N2: 5' ctccagacgcgccgggtaggtttc (SEQ ID NO: 23), Is-n2 5' ctgct-gcgccgaccactgaccc (SEQ ID NO:24) and genomic DNA from *S. lividans* as template. The protocol suggested by the manufacturer for GC-rich templates was followed in a PCR reaction consisting of the Platinum Pfx DNA polymerase with the Enhancer solution (Invitrogen). Two parallel PCR reactions were carried out. The first PCR reaction (reaction #1) utilized primers designated as us-sco1 5' gcccatatgagcgacatcacggt-cacc (SEQ ID NO:21) and Is-sco1 5' ggatcctcagcccgcgagcac-ccc (SEQ ID NO:22). The previous PCR product was used as the template. The PCR reaction product was a 1.269 kb PCR fragment. The PCR conditions used were: 30 cycles of denaturation at 94° C. for 55 seconds, annealing at 55° C. for 55 seconds, followed by extension for 1-2 minutes at 68° C. The polymerase used was Platinum Pfx DNA polymerase plus enhancer solution (Invitrogen). The resulting PCR product was cloned directly in an *E. coli* vector PCR Blunt TOPO (Invitrogen) and the sequence of the cloned SOx gene verified by DNA sequencing using primers provided in the kit.

The second PCR reaction (reaction #2) utilized primers us-s1 5'gccatgggcgacatcacggtcaccaac (SEQ ID NO:25) and Is-s1 5' atggatcctcagcccgcgagcacccc (SEQ ID NO:26) were used in a PCR reaction using the previous PCR product as template and the same conditions as above.

Figure 4:
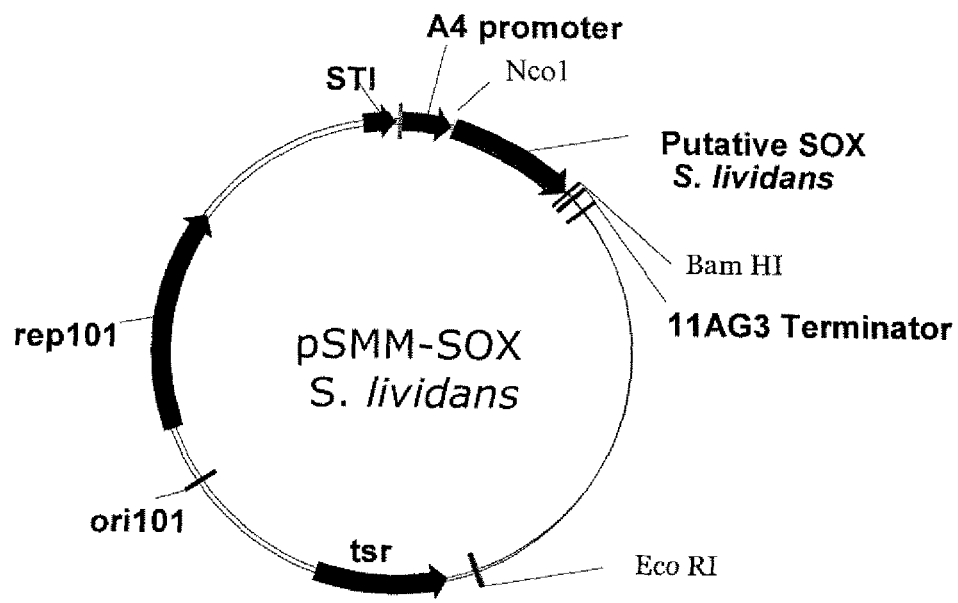
FIG. 4 provides a map of expression plasmid pSMM-SOx S. lividans.
Figure 5:
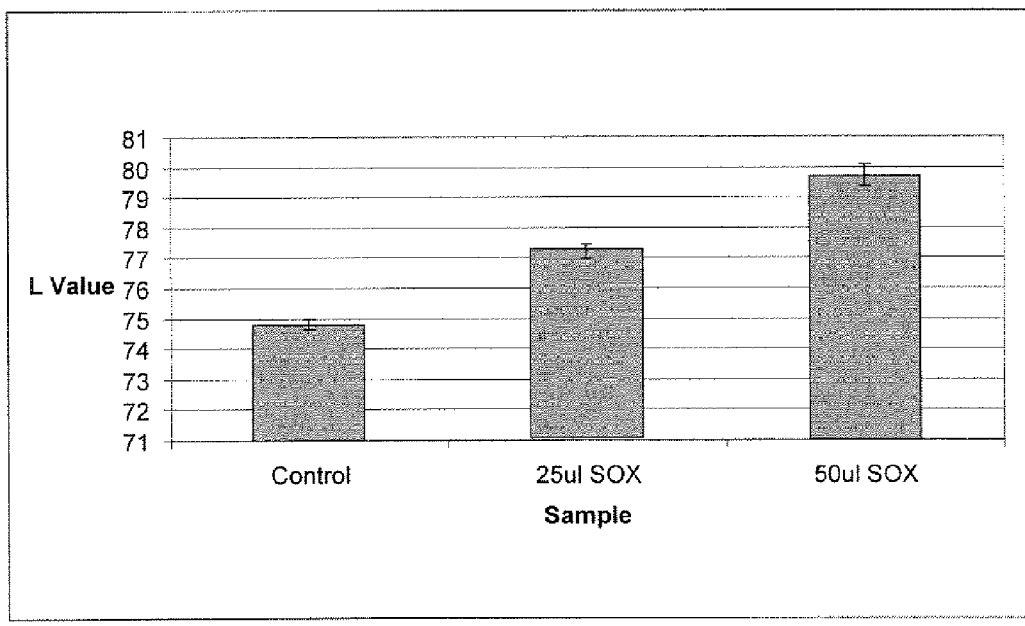
FIG. 5 provides a graph showing the results of a washing study to determine the ability of sorbitol oxidase to remove tea stains on cotton discs.
Figure 6:
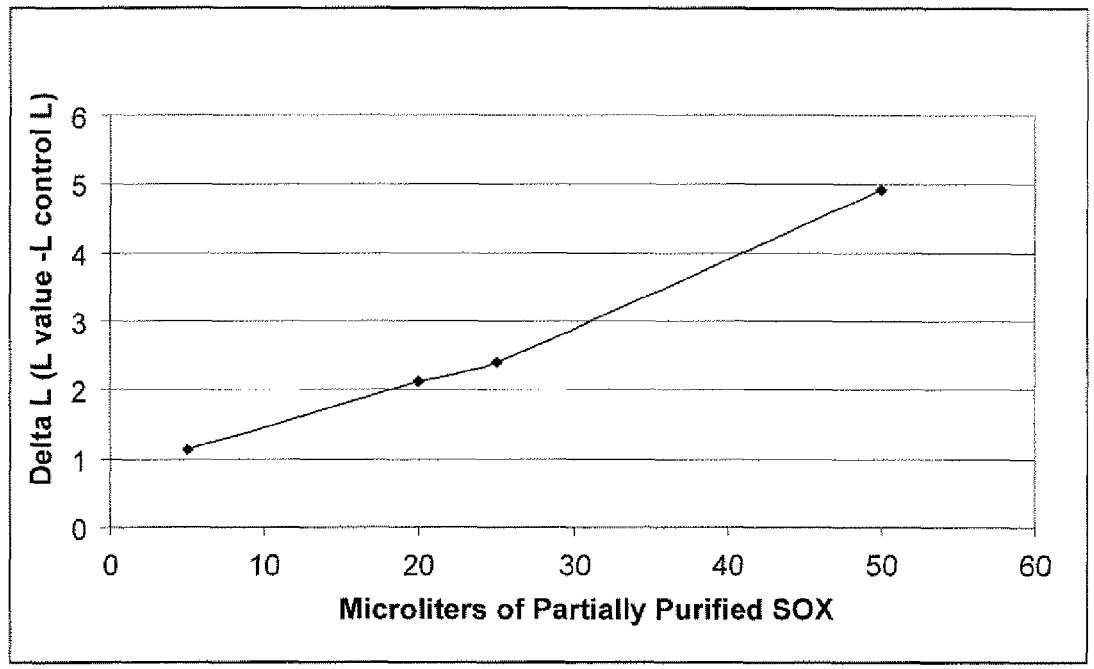
FIG. 6 provides a graph showing the results of a SOx dose study for bleaching of tea stains on cotton discs.
Figure 7:
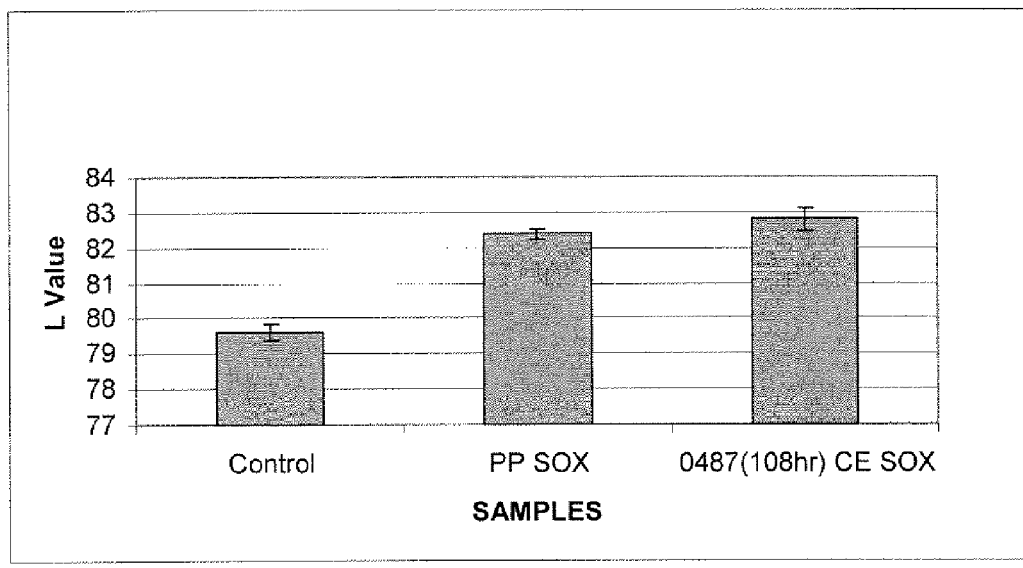
FIG. 7 provides a graph showing the results of a washing and bleaching performance study of sorbitol oxidase to remove of wine stains on cotton discs.
Figure 8:
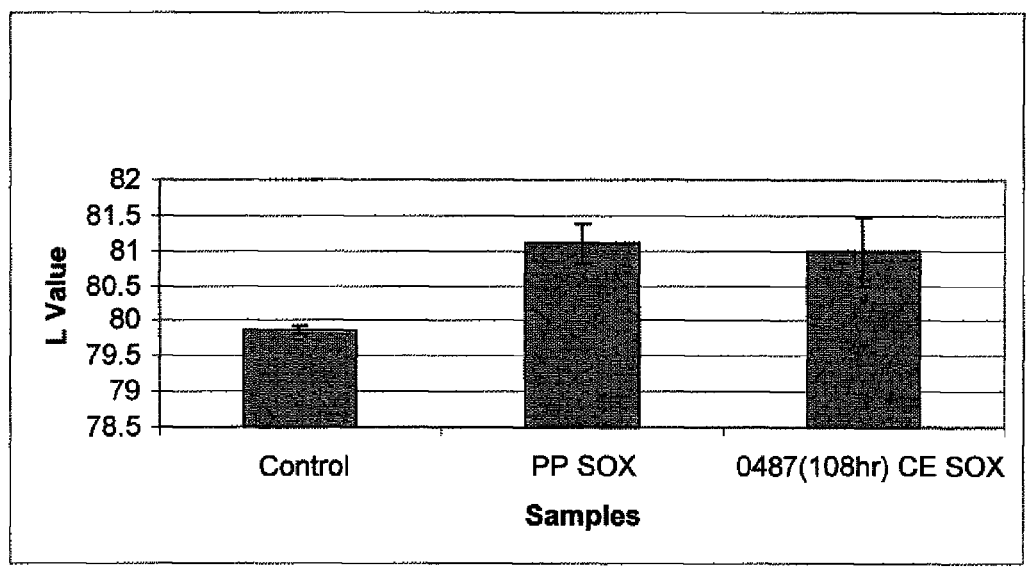
FIG. 8 provides a graph showing the results of a bleaching performance study of the ability of sorbitol oxidase to remove blueberry stains on cotton discs.

The 1.268 kb PCR product was digested with NcoI and BamHI, and the resulting fragment was cloned directly into an NcoI (partial digest) and BamHI digested *Streptomyces* vector pKB105. The final construct was the expression vector designated as pSMM-SOx (*S. lividans*) is shown in FIG. 4. Five ul of plasmid DNA was used to transform *Streptomyces* g3s3 protoplasts using methods known in the art.

The transformation reaction product was plated on R5 plates and incubated at 32° C. for 18 hours. A soft nutrient agar overlay containing thiostrepton at 50 ug/ml was then poured on the plates and the plates were incubated for an additional 3 days. Single colonies were used to inoculate a 250 ml flask with 20 ml TS-G media containing thiostrepton at 50 ug/ml. After 3 days of cultivation with shaking at 30° C., 2 ml aliquots were used to inoculate a 250 ml flask containing the *Streptomyces* Production Medium (See, above).

The cell pellets was collected by centrifugation, resuspended in buffer and disrupted, as described in Example 2. Table 2 shows the SOx activities present in the cell-free extracts derived from the different *Streptomyces* transformants. Twenty different transformants containing four DNAs encoding the SOx gene were analyzed for SOx activity, as described above. The results are provided in Table 2.

TABLE 2

SOx Activities of Twenty Different *Streptomyces* Transformants

| | SOx Activity (units/mg) | | | |
|---|---|---|---|---|
| Transformant | SOx DNA # 17 | DNA # 20 | DNA # 22 | DNA # 24 |
| 1 | 11.38 | 8.03 | 10.89 | 13.60 |
| 2 | 6.77 | 13.14 | 12.38 | 10.38 |
| 3 | 8.88 | 16.81 | 8.55 | 17.03 |
| 4 | 9.37 | 12.32 | 16.30 | 18.28 |
| 5 | 7.34 | 11.68 | 0.02 | 18.14 |

The activity of the SOx produced intracellularly by the *E. coli* host cells was greater than the activity of the SOx fusion protein produced extracellularly by other host cells as described in Examples

Example 4

Expression of the *Streptomyces* sp. H-7775 in *E. coli*

Figure 3:
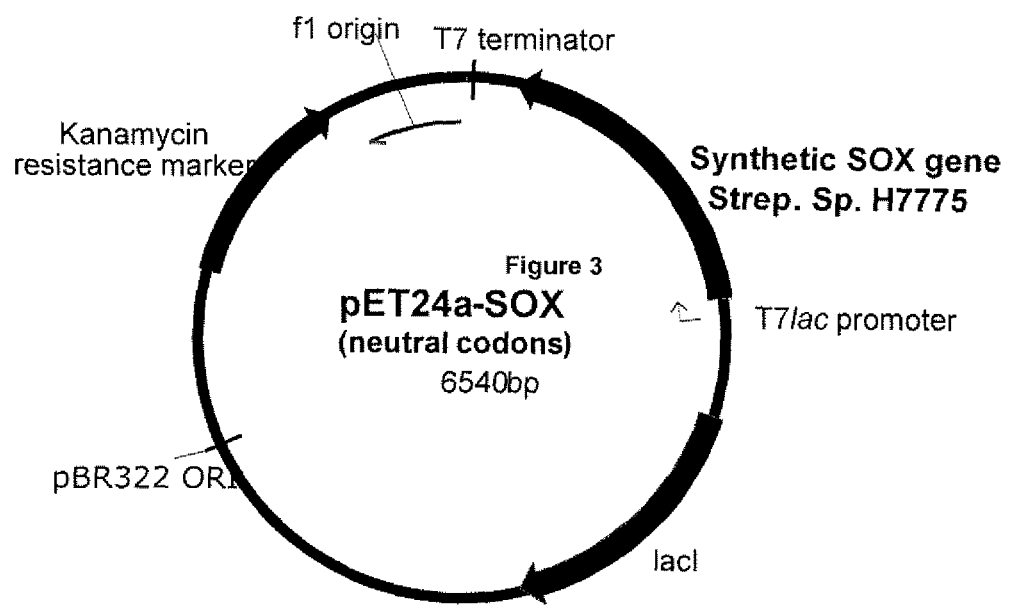
FIG. 3 provides a map of expression plasmid pet24a-SOx (neutral codons).

In this Example, methods for construction of an expression system for the expression of *Streptomyces* sp. H-7775 sorbitol oxidase (SOx) are described. A synthetic gene (with neutral codons) encoding the H-7775 SOx gene was used to express the sorbitol oxidase gene in *E. coli* strain BL21(DE3)pLysS. The expression vector pET 24a with the SOx gene was cloned as Nde1+BamH1 fragment. The resulting plasmid (See, FIG. 3) was transformed into competent *E. coli* Top10 cells (Invitrogen) according to the manufacturers protocol. Kanamycin resistant transformants containing the 1.2 kb SOx gene were identified by the direct colony PCR method using the TAQ Ready-to-go PCR beads (Amersham) using the PCR reaction conditions as suggested by the manufacturer. The following primers were used: us-sco1 5' gcccatatgagcgacatcacggtcacc (SEQ ID NO:21) and Is-sco1 5' ggatcctcagcccgcgagcacccc (SEQ ID NO:22) in the PCR reaction.

The SOx positive transformants were cultivated and plasmid DNA was isolated. Plasmid DNA containing the cloned SOx gene was then used to the commercially available BL21 (DE3)pLysS competent cells (cat. #200132; Stratagene) and following the protocol in the instruction manual.

The entire transformation reaction was directly used to inoculate 250 ml flasks containing 25 ml LB, containing kanamycin (50 ug/ml) and chloramphenicol (34 ug/ml). The cultures were incubated overnight with shaking at 37° C. For each transformant, a 2 liter flask containing 500 mls of LB containing kanamycin (50 ug/ml) and chloramphenicol (34 ug/ml) was then inoculated with 25 mls of the overnight culture and was further allowed to grow for 2 hours to reach approximately $OD_{600}$ values of 0.4-0.6 (mid logarithmic phase). Then, IPTG at a final concentration of 1 mM was added to the cultures. The cultures were further incubated for an additional 2 hours and then harvested by centrifugation. The resulting pellets were resuspended in phosphate buffer and the cells were passed through a French press for cell disruption/lysis. The SOx activity was determined using 10 ul cell lysate and 990 ul assay reagent (100 mM potassium phosphate, pH 7, 1% Sorbitol, 5 mM ABTS, 10 U/ml HRP) and incubated at 37° C. for 3 minutes.

Example 5

Purification of Sorbitol Oxidase

In this Example, methods used to purify sorbitol oxidase produced by *S. lividans* (SEQ ID NO:4) are described. Sorbitol oxidase from *Streptomyces lividans* is localized in mycelia. Thus, the enzyme was isolated by cell lysis using a French press from cell-extract in 100 mM Kpi buffer, potassium phosphate, pH 7.0. The cell extract was heated to 50° C. for one hour, followed by centrifugation sufficient to remove the debris. The cell lysate supernatant was then mixed with ammonium sulfate to 32% saturation to precipitate the protein fraction containing sorbitol oxidase. The protein precipitate was kept at 4° C. overnight and then was separated from mother liquor by centrifugation 10,000 RPM using Sorvall centrifuge and SLA-1500 Sorvall rotor.

The protein precipitate was then washed with 32% saturated ammonium sulfate solution. The washed protein precipitate was dissolved back in Kpi buffer and the insoluble material was discarded. The soluble fraction was dialyzed against 25 mM Kpi buffer, pH 7.0, overnight and then further purified using affinity chromatography on the reactive orange resin (Prometic). This partially purified sorbitol oxidase preparation and fermentation broth cell lysate (EFT of 108 hrs) were used as samples in experiments for biobleaching. The molecular weight of the enzyme was determined to be ~45,000 Da by SDS-PAGE gel electrophoresis. The prosthetic group is a covalently bound FAD (1 mol of FAD to 1 mol of SOx).

Example 6

Stability and Bleaching Performance of SOx in HDL Laundry Wash Conditions

In this Example, methods to determine the stability and bleaching performance of SOx (produced as described above) in AATCC liquid detergent laundry wash conditions are described. In these experiments, AATCC standard detergent (American Association of Textile Chemists and Colorists Heavy Duty Liquid Detergent Version 2003 without brightener; key components include linear alkane sulfonate, alcohol ethoxylate, propanediol, citric acid, fatty acid, castic soda and water; Testfabrics) was used.

Three bleachable cotton swatches with juice (STC CFT CS-15), wine (STC CFT CS-3), and tea (STC CFT BC-3) were used. The swatches were cut into 15 mm circles with a textile punch (Model B equipped with a 5/8" die cutter; Model 93046; NAEF).

Single swatch disks were placed into each well of a 24-well microplate (Costar 3526). One (1) ml of washing solution pH 8, containing per liter, 1.5 ml AATCC HDL detergent, 75-100 mM sorbitol, 6 gpg hardness (diluted from stock 15000 gpg hardness solution containing 1.735 M calcium chloride and 0.67 M magnesium chloride), and 0.05% TAED (tetraacetyl-ethylenediamine, Fluka) was added to each well. Five to fifty (5-50 ul) microliters of partially purified sorbitol oxidase or sorbitol oxidase obtain from a late fermentation run (108 hr EFT "effective fermentation time") produced as described in Examples 1 and 2, were added with a positive displacement pipette to 3-8 wells in one column. The control wells contained no enzyme. The microplate was covered with a plastic lid and aluminum foil and incubated at 37° C. with 100 rpm gentle rotation for 14 hr. The plates were then removed from the shaker and tested for the presence of hydrogen peroxide with peroxide test strips (Baker).

One hundred microliters (100 ul) of 0.1 mM sodium carbonate were added to each well to elevate the pH to 10. The microplates were incubated with rotation for another 90 min and the supernatants removed by aspiration. Each well was washed three (3) times with 1.5 ml Dulbecco's PBS, pH 7.3 and three (3) times with 1.5 ml distilled water. Each disk was removed from its well and dried overnight between sheets of paper towels and not exposed to direct light. The disks were inspected visually and then analyzed with a Reflectometer CR-200 (Minolta) calibrated on a standard white tile. The average L values were calculated as was the percent soil release (% SR=100%×(Final reflectance−Initial reflectance)/(Reflectance of a white standard-Initial reflectance). Graphs showing the results of these experiments are provided in FIGS. 5-8.

The results confirmed that sorbitol oxidase is stable in a typical liquid detergent system and is able to produce effective concentration of hydrogen peroxide in presence of its substrate sorbitol mixed with detergent and available atmospheric oxygen. In addition, the sorbitol oxidase generated hydrogen peroxide in presence of a bleach booster (i.e., TAED) was able to help bleach typical colored stains such as blueberry, tea and wine (See, FIGS. 5-8).

Example 7

Substrate Range Study of Sorbitol Oxidase

Sorbitol oxidase obtained using the methods described in Example 1, was tested for finding its activity with various polyol substrates. All substrates used in the assay were 50 mM in 10 mM phosphate buffer pH 7.0. The relative activity using sorbitol as (++++++=100%) is shown below in Table 3. Although the activity was very high for both substrates, it was noted that the SCO6147 SOx transformed in *S. lividans* exhibited 2.1 times more activity on D-sorbitol than on D-xylitol.

In addition to these substrates, it is contemplated that other substrates, including, but not limited to glycerol, will find use in the present invention.

TABLE 3

| Relative POx activities for corresponding substrates | |
| --- | --- |
| Compound | Relative Activity (+, 0) |
| D-Sorbitol | ++++++ |
| D-Xylitol | ++++ |
| D-Mannitol | +++ |
| D-Ribitol | + |
| Myo-Inositol | + |
| Glycerol | + |
| 1,3-propanediol | +/2 |
| 1,2-propanediol | +/2 |
| Propylene glycol | 0 |
| Ethylene glycol | 0 |

Example 8

Combined Enzyme System: Increased Hydrogen Peroxide Production Using SOx+GOx (Glucose Oxidase) and SOx+HOx (Hexose Oxidase)

The activity of a combination of POx enzymes was tested. The enzymes that were tested in combination were SOx with GOx and SOx with HOx. The SOx used in the experiments was recombinant SOx purified from *S. lividans* strain transformant #4 (SEQ ID NO:4), GOx is commercially available from Sigma (G7141) and HOx was prepared as described in WO 01/38544. HOx is available from Danisco A/S as Dairy-HOx™.

SOx, HOx and GOx have been discussed above, and can be summarized as follows.

Hexose oxidase (EC. 1.1.3.5) is a homo dimeric flavo enzyme containing 2 covalently bound FAD groups per molecule. The molecular weight is approx. 130 kDa. The enzyme catalyses the oxidation of D-hexose sugars including: glucose, galactose, lactose, maltose, malto-triose and cellobiose. The sugars are converted into their corresponding lactones, which undergo spontaneous hydrolysis to the corresponding acids in aqueous environments. Upon re-oxidation of the reduced flavin group by molecular oxygen, $H_2O_2$ is produced.

Sorbitol oxidase is a monomeric flavo enzyme containing one flavin group of unknown nature, bound covalently, probably to a histidine residue in the holoenzyme. The molecular weight of the enzyme is approximately 45 kDa. The enzyme catalyses the oxidation of several polyols including: D-sorbitol, D-xylitol, D-glucose, D-mannitol, D-arabitol, glycerol, inositol, 1,2-propanediol, 1,3-butanediol, and 1,4-butanediol. Upon oxidation of the polyols the corresponding sugars are generated and upon contact with molecular oxygen the flavin is re-oxidized and $H_2O_2$ is produced.

Glucose oxidase (EC. 1.1.3.4) is a dimeric protein with a molecular weight of about 160 kDa containing 1 non-covalently, but tightly associated flavin group per monomer. The enzyme catalyses the oxidations of D-glucose and to a lesser extend 2-deoxy-D-glucose, D-mannose and D-fructose. The sugars are converted into their corresponding lactones, which undergo spontaneous hydrolysis to the corresponding acids in aqueous environments. Upon re-oxidation of the reduced flavin group by molecular oxygen, $H_2O_2$ is produced.

Activity assays of SOx, HOx or GOx activity were performed in microtiter plates (300 µl).

The amount of enzyme in each combination was given as unit amount, wherein a unit of HOx is the amount of enzyme that produced 1 umol H2O2/min when substrates are in excess; a unit of GOx is the amount of enzyme that produced 1 umol H2O2/min when substrates are in excess; and a unit of SOx is the amount of enzyme that produced 1 umol H2O2/min when substrates are in excess. In the present example, only SOx had excess substrate. The generated sugar would be the limiting factor for the secondary enzyme. As noted above the activity is given as a percentage value of SOx catalyzing D-sorbitol when both D-sorbitol and oxygen is in excess.

The commonly used horse radish peroxidase dye substrate ABTS was incorporated into an assay, measuring the production of $H_2O_2$ produced by HOx or GOx respectively. ABTS serves as a chromogenic substrate for peroxidase. Peroxidase in combination with $H_2O_2$ facilitates the electron transport from the chromogenic dye, which is oxidized to an intensely green/blue compound.

An assay mixture contained 266 µl sorbitol (Sigma P-5504, 0.055 M in 0.1 M sodium phosphate buffer, pH 6.3), 11.6 µl 2,2'-Azino-bis(3-ethylbenzothiozoline-6-Sulfonic acid) (ABTS) (Sigma A-9941, 5 mg/ml aqueous solution), 11.6 µl peroxidase (POD) (Sigma P-6782, 0.1 mg/ml in 0.1 M sodium phosphate buffer, pH 6.3) and 10 µl enzyme (SOx or HOx) aqueous solution.

The incubation was started by the addition of glucose at 25° C. The absorbance was monitored at 405 nm in an ELISA reader. A standard curve, based on varying concentrations of $H_2O_2$, was used for calculation of enzyme activity according to the definition above.

Initial velocities were measured over 5 minutes in 300 uL ABTS assay (as described previously). The production of rate of hydrogen peroxide production was extrapolated from a standard curve. The measured activity is given as a percentage value. 100% is defined as the rate of hydrogen peroxide production by sorbitol oxidase alone, when the substrates D-sorbitol and oxygen is in excess (Linear velocity curves).

Figure 9A:
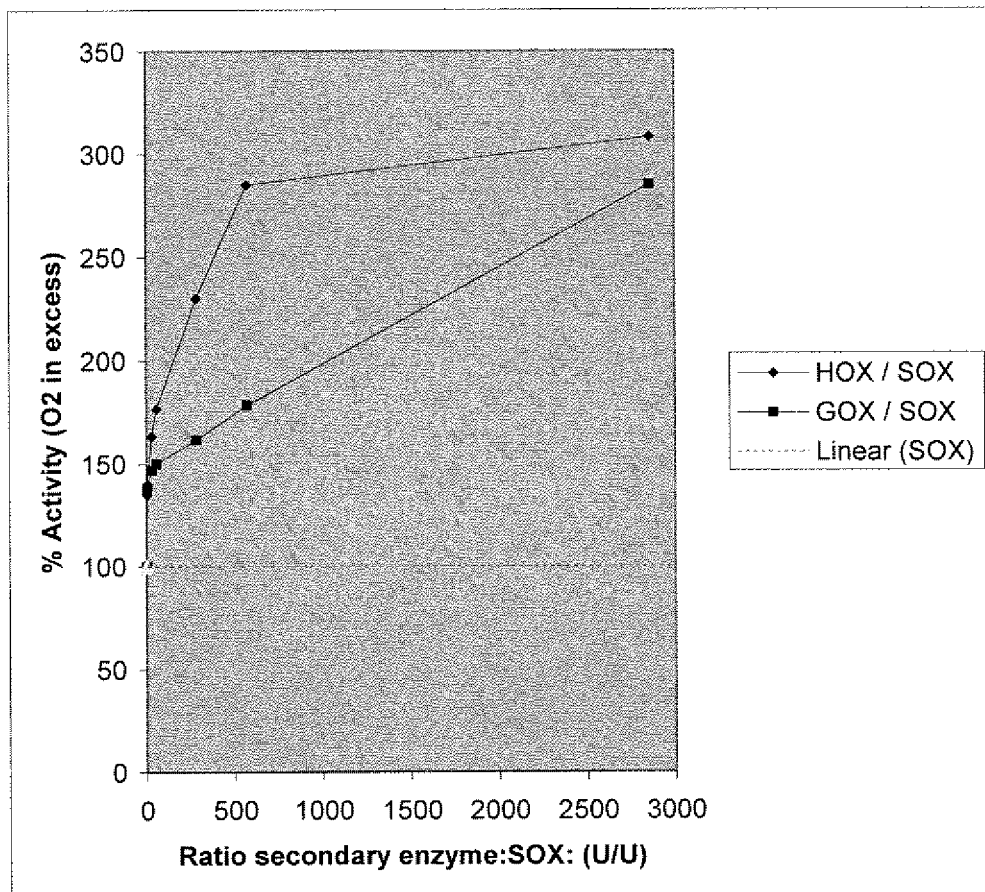
FIG. 9 (A-B) show the rate of H2O2 production by a combination of a constant amount of a first polyol oxidase (SOx) with an increasing amount of a second polyol oxidase (HOx or GOx). The amount of GOx or HOx relative to the constant amount of SOx was increased between 1× and 3000× (A) or 1× and 100× (B), and the rate of H2O2 production was measured over 5 minutes in a 300 ul ABTS assay. The combination of SOx with HOx (♦) or SOx with GOx (■) resulted in a synergistic increase in the production of H2O2 of between 250 and 300% of that seen with SOx alone (--) at 3000× (A).
Figure 9B:
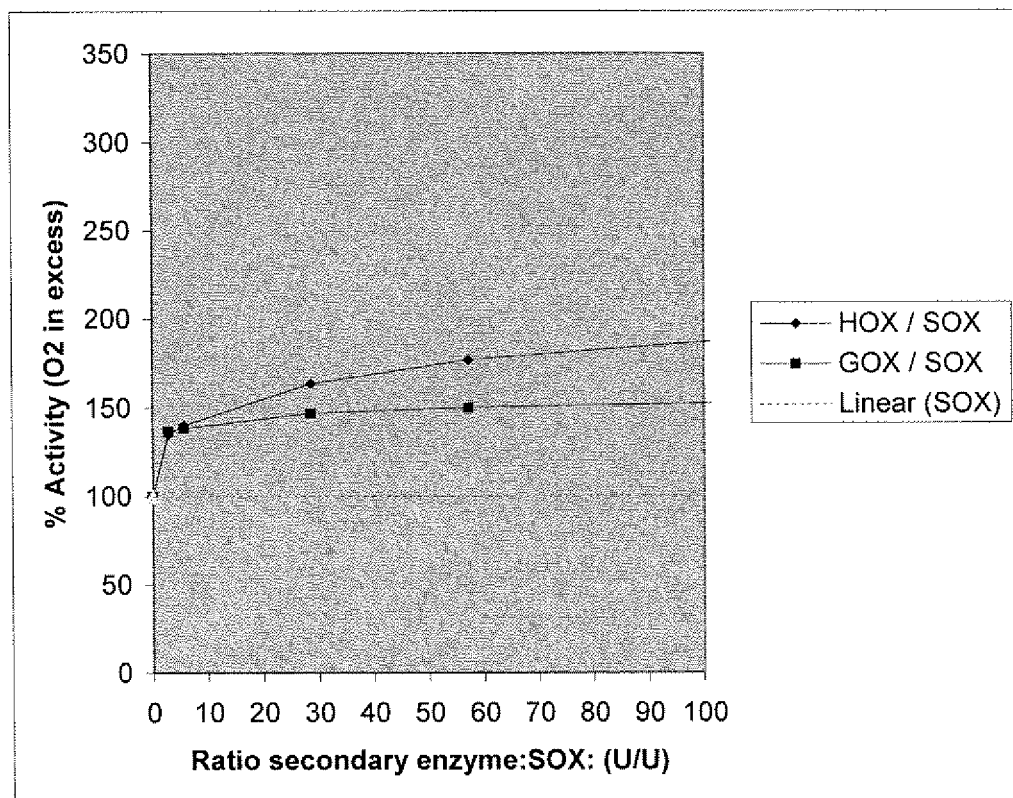

FIG. 9 (A-B) shows the initial velocity of $H_2O_2$ production using the compositions with between 1× and 3000× excess of the oxidoreductases (glucose oxidase & hexose oxidase) compared to the polyol oxidase (sorbitol oxidase) measured over 5 minutes in 300 ul ABTS assay. A dramatic synergy was seen with both glucose oxidase and hexose oxidase, with up to 250-300% increase in hydrogen peroxide production rate seen. Dosages greater than 1×, such as at least 2× of the oxidoreductase compared to the polyol oxidase resulted in increased hydrogen peroxide production.

Example 9

**Construction of *Streptomyces lividans* & *Bacillus subtilis* Strains Expressing Polyol Oxidases (POx)**

Table 4 shows the elements of polynucleotide constructs that were generated to express POx enzymes derived from *A. cellulolyticus*, *Arthrobacter* sp, and *Streptomyces* H-7775 in *Bacillus* and/or *Streptomyces* host cells.

TABLE 4

| Expression Constructs | Polyol Oxidase (POx) Genes (sorbitol/xylitol oxidases) | N-terminal fusion to POx | Expression Host |
|---|---|---|---|
| pSMM-ES2 | *Acidothermus cellulolyticus* 11B Q2E2H5 (synthetic gene); amino acid sequence SEQ ID NO: 6 | signal peptide SC07637 SEQ ID NO: 31 | *Streptomyces lividans* |
| pSMM-POx(intra) | *Acidothermus cellulolyticus* 11B Q2E2H5 (synthetic gene) amino acid sequence SEQ ID NO: 6 | none | *Streptomyces lividans* |
| pSM-ES3 | *Arthrobacter* sp. FB 24 (Q4NJLO) (synthetic gene) amino acid sequence SEQ ID NO: 12 | Signal peptide SCO0624 SEQ ID NO: 39 | *Streptomyces lividans* |
| pSM CG-SOx | *Streptomyces* H-7775 (synthetic gene) amino acid sequence SEQ ID NO: 2 | Cgt signal sequence. SEQ ID NO: 36 | *Bacillus subtilis* |
| pSM CG-SOx (ES2 Acid.) | *Acidothermus cellulolyticus* 11B Q2E2H5 (synthetic gene) amino acid sequence SEQ ID NO: 6 | Cgt signal sequence. SEQ ID NO: 36 | *Bacillus subtilis* |

For extracellular expression of POx, the following signal sequences were fused to the mature form of the POx enzyme as described herein.

MGFGSAPIALCPLRTRRNALKRLLAL-LATGVSIVGLTALAGPPAQA (SEQ ID NO:31) secreted endoglucanase from *Streptomyces coelicolor* SCO7363

MHEPHLDRRLFLKGTAVTGAALALGATAAPTASA (SEQ ID NO:39) possible secreted protein *Streptomyces coelicolor* SCO0624 MKKFLKSTAALALGLSLTFGLFSPAQA (SEQ ID NO:36) amino acid signal sequence of the *Bacillus circulans* cyclomaltodextrin glucanotransferase (cgt) precursor (accession P43379).

Example 10

Construction of *Streptomyces lividans* & *Bacillus subtilis* Strains Expressing Polyol Oxidase (POx) from *Acidothermus cellulolyticus* 11B In this example, experiments were conducted to functionally characterize the putative polyol oxidase (xylitol oxidase) □2E2H5 from *Acidothermus cellulolyticus* 11B. The putative POx protein was expressed in two different host organisms (*Streptomyces lividans* and *Bacillus subtilis*). The POx protein sequence was retrieved from the database (SEQ ID NO:6). A synthetic polynucleotide encoding the *Acidothermus cellulolyticus* 11B Q2E2H5 POx protein was obtained from GeneArt (Germany).

The *Acidothermus* POx synthetic gene was designed with a truncated signal sequence ALAGPPAQA (SEQ ID NO:32) from a secreted endoglucanase from *Streptomyces coelicolor* SCO7363. *Acidothermus* POx was expressed in *Streptomyces* as a fusion protein (SEQ ID NO:35), resulting in the N-terminal extension MGFGSAPIALCPLRTRRNALKRLLAL-LATGVSIVGLTALAGPPAQA (SEQ ID NO:31) (from SCO7363 signal sequence) fused to the mature POx sequence (SEQ ID NO:6). The amino acid sequence encoded by the synthetic *Acidothermus* POx gene (SEQ ID NO:33) is as follows.

(SEQ ID NO: 33)
ALAGPPAQAMDGGKRCRDGTPQPPAPSEQVTPSAAASLRAAYDVEVSAPRLRNWAGN

IAFRPRRYVQPRDLDELVEIIRVSDQVRVLGTGHSFNPIADTTGTLISLDHLPREVRVMPG

RTAVSAGTRYGDLAFPLHEAGWALANVGSLPHISIAGACATATHGSGDRNGCLATAVAG

MTGVDGTCRVFHLTAESPEFPGAVVHLGALGAVTEIELVTEPTFTVRQWVYEDAPLDNV

FADLDDVTSAAYSVSIFTTWDPPTARQIWLKERVAAGRPDPPARRWGGRLAERDHNPV

PGMPPENCTPQLGRIGPWHERLPHFRLDVTPSAGDELQSEYFVPRAAAVEAYRALRHIG

SRIAPVLQISEIRTVAADELWLSPAYHRPSVAFHFTWIADEEAVRPVVSEVERALAPLQPR

PHWGKLFTMDPAVVRAAYPRFDDFVALAERYDPEGKFQNDFLRRFFAG

The polynucleotide sequence of the synthetic *Acidothermus* POx gene (SEQ ID NO:34) is as follows.

(SEQ ID NO: 34)
GCGCTAGCGGGCCCGCCGGCCCAGGCCATGGATGGCGGCAAGCGCTGCC

GCGACGGCACCCCGCAGCCGCCGGCCCCGTCCGAGCAGGTCACCCCGTC

GGCCGCCGCCTCCCTGCGGGCCGCCTACGACGTGGAGGTCTCCGCCCCG

CGCCTGCGCAACTGGGCCGGCAACATCGCCTTCCGCCCGCGCCGCTACG

TCCAGCCGCGCGACCTCGACGAGCTGGTCGAGATCATCCGGGTCTCCGA

CCAGGTCCGCGTCCTGGGCACCGGCCACTCCTTCAACCCCATCGCCGAC

ACCACCGGCACCCTGATCTCCCTGGACCACCTGCCGCGCGAGGTCCGCG

TCATGCCGGGCCGCACCGCGGTCTCCGCCGGCACCCGCTACGGCGACCT

GGCCTTCCCGCTGCACGAGGCCGGCTGGGCCCTGGCCAACGTCGGCTCC

CTGCCGCACATCTCCATCGCCGGCGCCTGCGCCACGGCCACCCACGGCT

CCGGCGACCGCAACGGCTGCCTGGCCACCGCCGTCGCCGGCATGACCGG

CGTCGACGGCACCTGCCGCGTGTTCCACCTGACCGCCGAGTCCCCCGAG

TTCCCGGGCGCCGTCGTCCACCTGGGCGCCCTGGGCGCCGTCACCGAGA

TCGAGCTGGTCACCGAGCCGACCTTCACCGTCCGCCAGTGGGTCTACGA

GGACGCCCCGCTGGACAACGTGTTCGCCGACCTGGACGACGTCACCTCC

GCCGCCTACTCGGTCTCCATCTTCACCACCTGGGACCCGCCGACCGCCC

GGCAGATCTGGCTGAAGGAGCGCGTCGCCGCCGGCCGCCCGGACCCGCC

GGCCCGCCGCTGGGGCGGCCGCCTCGCCGAGCGCGACCACAACCCCGTC

CCGGGGATGCCGCCCGAGAACTGCACCCCCCAGCTGGGCCGCATCGGCC

CGTGGCACGAGCGCCTGCCGCACTTCCGCCTGGACGTCACCCCCTCCGC

GGGCGACGAGCTGCAGTCCGAGTACTTCGTCCCGCGCGCCGCCGCCGTC

GAGGCCTACCGCGCCCTGCGCCACATCGGCTCCCGCATCGCCCCGGTCC

TGCAGATCTCCGAGATCCGCACCGTCGCCGCCGACGAGCTGTGGCTGTC

CCCGGCCTACCACCGCCCGTCCGTCGCCTTCCACTTCACCTGGATCGCC

GACGAGGAGGCCGTCCGCCCGGTGGTCTCCGAGGTCGAGCGCGCCCTGG

CCCCGCTGCAGCCGCGCCCGCACTGGGGCAAGCTGTTCACGATGGACCC

GGCCGTCGTCCGCGCCGCCTACCCGCGCTTCGACGACTTCGTCGCCCTG

GCCGAGCGCTACGACCCCGAGGGCAAGTTCCAGAACGACTTCCTGCGCC

GCTTCTTCGCCGGCTAAGGATCC.

A restriction site for nhe1 (GCTAGC) was introduced at the 5' end of the synthetic gene to allow fusion to the truncated SCO7363 endoglucanase signal sequence. The BamH1 (GGATCC) restriction site was added at the 3' end of the gene. Restriction digestion with nhe1 plus Bam H1 resulted in the DNA fragment which was ligated with the nhe1/BamH1 cut *Streptomyces* expression plasmid pKB 105. The cloning resulted in the expression construct pSMM-ES2 with a full length signal peptide for expression of secreted POx proteins in *Streptomyces lividans* (SEQ ID NO: 35).

(SEQ ID NO: 35)
MGFGSAPIALCPLRTRRNALKRLLALLATGVSIVGLTALAGPPAQAMDGGKRCRDGTPQ

PPAPSEQVTPSAAASLRAAYDVEVSAPRLRNWAGNIAFRPRRYVQPRDLDELVEIIRVSD

QVRVLGTGHSFNPIADTTGTLISLDHLPREVRVMPGRTAVSAGTRYGDLAFPLHEAGWA

LANVGSLPHISIAGACATATHGSGDRNGCLATAVAGMTGVDGTCRVFHLTAESPEFPGA

VVHLGALGAVTEIELVTEPTFTVRQWVYEDAPLDNVFADLDDVTSAAYSVSIFTTWDPPT

ARQIWLKERVAAGRPDPPARRWGGRLAERDHNPVPGMPPENCTPOLGRIGPWHERLP

HFRLDVTPSAGDELOSEYFVPRAAAVEAYRALRHIGSRIAPVLQISEIRTVAADELWLSPA

YHRPSVAFHFTVVIADEEAVRPVVSEVERALAPLQPRPHWGKLFTMDPAVVRAAYPRFD

DFVALAERYDPEGKFQNDFLRRFFAG

The DNA fragment encoding the mature POx protein from *Acidothermus* (SEQ ID NO:6) (without a signal peptide) was also generated (SEQ ID NO:42).

(SEQ ID NO: 42)
CCATGGATGGCGGCAAGCGCTGCCGCGACGGCACCCCGCAGCCGCCGGC

CCCGTCCGAGCAGGTCACCCCGTCGGCCGCCGCCTCCCTGCGGGCCGCC

TACGACGTGGAGGTCTCCGCCCCGCGCCTGCGCAACTGGGCCGGCAACA

TCGCCTTCCGCCCGCGCCGCTACGTCCAGCCGCGCGACCTCGACGAGCT

GGTCGAGATCATCCGGGTCTCCGACCAGGTCCGCGTCCTGGGCACCGGC

CACTCCTTCAACCCCATCGCCGACACCACCGGCACCCTGATCTCCCTGG

ACCACCTGCCGCGCGAGGTCCGCGTCATGCCGGGCCGCACCGCGGTCTC

CGCCGGCACCCGCTACGGCGACCTGGCCTTCCCGCTGCACGAGGCCGGC

TGGGCCCTGGCCAACGTCGGCTCCCTGCCGCACATCTCCATCGCCGGCG

CCTGCGCCACGGCCACCCACGGCTCCGGCGACCGCAACGGCTGCCTGGC

CACCGCCGTCGCCGGCATGACCGGCGTCGACGGCACCTGCCGCGTGTTC

CACCTGACCGCCGAGTCCCCCGAGTTCCCGGGCGCCGTCGTCCACCTGG

GCGCCCTGGGCGCCGTCACCGAGATCGAGCTGGTCACCGAGCCGACCTT

CACCGTCCGCCAGTGGGTCTACGAGGACGCCCCGCTGGACAACGTGTTC

GCCGACCTGGACGACGTCACCTCCGCCGCCTACTCGGTCTCCATCTTCA

CCACCTGGGACCCGCCGACCGCCCGGCAGATCTGGCTGAAGGAGCGCGT

CGCCGCCGGCCGCCCGGACCCGCCGGCCCGCCGCTGGGCGGCCGCCTC

GCCGAGCGCGACCACAACCCCGTCCCGGGGATGCCGCCCGAGAACTGCA

CCCCCCAGCTGGGCCGCATCGGCCCGTGGCACGAGCGCCTGCCGCACTT

CCGCCTGGACGTCACCCCCTCCGCGGGCGACGAGCTGCAGTCCGAGTAC

TTCGTCCCGCGCGCCGCCGCCGTCGAGGCCTACCGCGCCCTGCGCCACA

TCGGCTCCCGCATCGCCCCGGTCCTGCAGATCTCCGAGATCCGCACCGT

CGCCGCCGACGAGCTGTGGCTGTCCCCGGCCTACCACCGCCCGTCCGTC

GCCTTCCACTTCACCTGGATCGCCGACGAGGAGGCCGTCCGCCCGGTGG

TCTCCGAGGTCGAGCGCGCCCTGGCCCCGCTGCAGCCGCGCCCGCACTG

GGGCAAGCTGTTCACGATGGACCCGGCCGTCGTCCGCGCCGCCTACCCG

CGCTTCGACGACTTCGTCGCCCTGGCCGAGCGCTACGACCCCGAGGGCA

AGTTCCAGAACGACTTCCTGCGCCGCTTCTTCGCCGGCTAAGGATCC.

Restriction digestion with Nco1 and BamH1 resulted in a DNA fragment which was ligated to the Nco1 partial digest plus BamH1 cut pKB 105 vector. Cloning resulted in the expression construct pSMM-POx(intra), for the intracellular expression of the mature *Acidothermus* POx protein.

The expression plasmids pSMM-ES2 and pSMM-POx(intra) were transformed into *Streptomyces lividans* strain g3s3 and 10 transformants each were selected and grown in TS medium for 2-3 days in the presence of 50 ug/ml thiostrepton at 30° C. Cells were then transferred to a production medium free of antimicrobials and growth was continued for another three days. Then, 1 ml cultures was collected and centrifuged under conditions sufficient to separate the cells from the supernatants. The supernatants and cell pellets obtained were tested in enzyme activity assays.

The Nco1/BamH1 digested DNA fragment was also used to construct the expression plasmid pSM CG-SOx (ES2 Acid.). The *Bacillus subtilis* vector pCG (Danisco A/S) was digested with Nco1/BamH1 and ligated to the POx DNA fragment. The resulting fusion protein (SEQ ID NO:37) comprises the mature POx gene to the 27 amino acids signal peptide MKKFLKSTAALALGLSLTFGLFSPAQA (SEQ ID NO: 36) of the *Bacillus circulans* cyclomaltodextrin glucanotransferase precursor (accession P43379).

(SEQ ID NO: 37)
MKKFLKSTAALALGLSLTFGLFSPAQAMDGGKRCRDGTPQPPAPSEQVTPSAAASLRA

AYDVEVSAPRLRNWAGNIAFRPRRYVQPRDLDELVEIIRVSDQVRVLGTGHSFNPIADTT

GTLISLDHLPREVRVMPGRTAVSAGTRYGDLAFPLHEAGWALANVGSLPHISIAGACATA

THGSGDRNGCLATAVAGMTGVDGTCRVFHLTAESPEFPGAVVHLGALGAVTEIELVTEP

TFTVRQWVYEDAPLDNVFADLDDVTSAAYSVSIFTTANDPPTARQIWLKERVAAGRPDPP

```
                                   -continued
ARRWGGRLAERDHNPVPGMPPENCTPQLGRIGPWHERLPHFRLDVTPSAGDELQSEY

FVPRAAAVEAYRALRHIGSRIAPVLQISEIRTVAADELWLSPAYHRPSVAFHFTVVIADEEA

VRPVVSEVERALAPLQPRPHWGKLFTMDPAVVRAAYPRFDDFVALAERYDPEGKFQND

FLRRFFAG.
```

The pSM CG-SOx (ES2 Acid.) and pSM CG-SOx plasmids were used for transformation of the *Bacillus subtilis* OS21 strain. Transformants were isolated and grown in 5 ml LB media containing 50 mg/li Kanamycin. The cultures were cultivated at 30° C. with shaking at 180 rpm for 24 hours. SOx activities were determined from culture supernatants of host cells secreting the SOx and cell lysates of host cells that produced SOx intracellularly.

The data obtained from the experiments showed that the SOx produced from host cells that had been transformed with a polynucleotide encoding the mature form of the SOx enzyme (i.e. lacking the sequence encoding the signal peptide) had greater SOx activity than the SOx produced by host cells that had been transformed with a polynucleotide encoding the fusion SOx protein (i.e. a SOx fusion protein comprising the mature form operably linked to a signal peptide).

Example 13

Construction of *Streptomyces lividans* Strains Expressing Polyol Oxidase (POx) from *Arthrobacter* sp. FB 24

In this example, experiments were conducted to functionally characterize the putative polyol oxidase (FAD linked oxidase) (Q4NJLO; SEQ ID NO:11) from *Arthrobacter* sp. FB 24 are described. The putative POx protein was expressed in *Streptomyces lividans*. The POx protein sequence was retrieved from the database. Synthetic gene encoding the *Arthrobacter* sp. FB 24 (Q4NJLO) POx protein was obtained from Generate (Germany).

The *Arthrobacter* sp. FB 24 POx synthetic gene was designed with an N-terminal extension MHEPHLDRRLFLKGTAVTGAALALGATAAPTASA (SEQ ID NO:39) derived from a possible secreted *Streptomyces coelicolor* A3(2) protein SCO0624 resulting in the protein sequence below (SEQ ID NO:40). Two glycine residues were inserted after the initiator methionine of the signal sequence and before the start methionine of the mature POx protein.

The two glycine residues resulted from incoporating restriction sites Nco1 and sph1. as shown in the synthetic gene sequence below (SEQ ID NO:41). The synthetic POx gene was cut with the restriction enzymes Nco1 and BamH1 and the resulting DNA fragment was ligated to the Nco1 partial and BamH1 digested *Streptomyces* vector pKB105. This resulted in the expression vector pSM-ES3. This plasmid was transformed into *Streptomyces lividans* strain g3s3 and 10 transformants were selected and grown in TS medium for 2-3 days in the presence of 50 ug/ml thiostrepton at 30° C. Cells were then transferred to a production medium free of antimicrobials and growth was continued for another three days. Then, 1 ml cultures was collected and centrifuged under conditions sufficient to separate the cells from the supernatants. The supernatants and cell pellets obtained were tested in enzyme activity assays.

```
                                            (SEQ ID NO: 41)
ACCATGGGCCACGAGCCGCACCTGGACCGCCGCCTGTTCCTGAAGGGCA

CCGCCGTCACCGGCGCCGCCCTGGCCCTGGGCGCCACCGCCGCCCCGAC

CGCCTCCGCCGGCATGCGCACGGTCTCCGAGCTGCCGGGCCTGTCGGGC

TCCACCGGCGCCGGCTCCTCCGCCCCCGAGCTGAACTGGGCCGGCAACT

ACCGCTACACCGCCGCCTCCATCCACCGCCCGCGCACCCTCGAGGAGGT

CCAGGAGGTCGTCGCGGGCGCCTCCAAGATCCGCGCCCTGGGCTCCCGC

CACTCCTTCAACGCCATCGCCGACTCCCCGGGCAGCCTGGTCTCCCTCG

AGGACCTGGACCCGGGCATCCGCATCGACGCCGCCACCCGCACCGTCAC

GGTCTCGGGCGGCACGCGCTACGGCACCCTGGCCGAGCAGCTCGAGTCC

GCCGGCTTCGCCCTGTCCAACCTGGCCTCCCTGCCGCACATCTCCGTCG

CCGGCGCCATCGCCACCGCCACCCACGGCTCCGGCGACGCCAACGGCAA

CCTGGCCACCTCCGTCGCCGCCCTCGAGCTGGTCGCGGCCGACGGCACC
```

```
                                             (SEQ ID NO: 40)
MGHEPHLDRRLFLKGTAVTGAALALGATAAPTASAGMRTVSELPGLSGSTGAGSSAPE

LNWAGNYRYTAASIHRPRTLEEVQEVVAGASKIRALGSRHSFNAIADSPGSLVSLEDLDP

GIRIDAATRTVTVSGGTRYGTLAEQLESAGFALSNLASLPHISVAGAIATATHGSGDANG

NLATSVAALELVAADGTVHRLNRGSSPGFDGAVVGLGALGVVTKVTLDIEPTFTVRQDV

FEALPWDTVLGNFDAVTSSAYSVSLFTDWSGDDVAQAWLKSRLSGSAASSDAGSTLAG

EAFAAGTFFGGTRAGVARHPLPGVSAENCTEQLGVPGSWSERLAHFRMAFTPSSGEEL

QSEFFVRREHAVAAIGELRALSDRITPLLLVSEIRTVAADKLWLSTAYGQDSVGFHFTANK

QRQDEVEKVLPVMEEALAPFNARPHWGKLFHAGADAVAELYPRFSDFKDLAERMDPE

QKFRNEFLARKVFGN
```

-continued

```
GTCCACCGCCTGAACCGCGGCTCCTCCCCGGGCTTCGACGGCGCGGTCG

TCGGCCTGGGCGCCCTGGGCGTCGTCACCAAGGTCACCCTGGACATCGA

GCCGACCTTCACCGTCCGCCAGGACGTGTTCGAGGCCCTGCCGTGGGAC

ACCGTCCTGGGCAACTTCGACGCCGTCACCTCCTCCGCCTACTCCGTGT

CCCTGTTCACCGACTGGTCCGGCGACGACGTCGCCCAGGCCTGGCTGAA

GTCCCGCCTGTCCGGCTCCGCCGCCTCCTCCGACGCCGGCTCCACCCTG

GCCGGCGAGGCCTTCGCCGCCGGCACCTTCTTCGGCGGCACCCGCGCCG

GCGTCGCCCGCCACCCGCTGCCGGGCGTGTCCGCCGAGAACTGCACCGA

GCAGCTGGGCGTCCCGGGCTCCTGGTCCGAGCGCCTGGCCCACTTCCGC

ATGGCCTTCACCCCGTCCTCCGGCGAGGAGCTGCAGTCCGAGTTCTTCG

TCCGCCGCGAGCACGCCGTGGCCGCCATCGGCGAGCTGCGCGCCCTGTC

CGACCGCATCACCCCGCTGCTGCTGGTCTCCGAGATCCGCACCGTCGCC

GCCGACAAGCTGTGGCTGTCCACCGCCTACGGCCAGGACTCCGTCGGCT

TCCACTTCACCTGGAAGCAGCGCCAGGACGAGGTCGAGAAGGTCCTGCC

GGTCATGGAGGAGGCCCTGGCCCCGTTCAACGCCCGCCCGCACTGGGGC

AAGCTGTTCCACGCCGGCGCCGACGCCGTCGCCGAGCTGTACCCGCGCT

TCTCCGACTTCAAGGACCTGGCCGAGCGCATGGACCCCGAGCAGAAGTT

CCGCAACGAGTTCCTGGCCCGCAAGGTGTTCGGCAACTGATGAGGATCC

G.
```

Example 14

Bleaching Performance of SOx in Combination with Perhydrolase in HDL Laundry Wash Conditions The effect of a cleaning composition containing a POx enzyme and a perhydrolase in bleaching a stained fabric is tested.

The effect of bleaching a stained fabric with a composition comprising perhydrolase *M. smegmatis* perhydrolase, variant S54V described in PCT/US05/056782 in combination with SOx is tested on fabric stained with tea, or wine or blueberry essentially as described in Example 5 but without TAED. The bleaching effect of SOx alone on the stained fabric swatches is performed as described in Example 5. To determine the bleaching effect of a combination of SOx and perhydrolase on fabric swatches stained in the same manner as those tested for SOx alone, 1 ppm of perhydrolase and 5 mM perhydrolase substrate (ester) are combined with the sorbitol oxidase and added to the stained swatch disks in the microplate. The percent soil release is determined and the bleaching performance of SOx in combination with perhydrolase is calculated.

The bleaching effect of the combination of perhydrolase with SOx is significantly greater than the bleaching effect obtained with SOx alone.

Therefore, this example illustrates the usefulness of combining a POx and a perhydrolase in cleaning compositions.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

Having described the preferred embodiments of the present invention, it will appear to those ordinarily skilled in the art that various modifications may be made to the disclosed embodiments, and that such modifications are intended to be within the scope of the present invention.

Those of skill in the art readily appreciate that the present invention is well adapted to carry out the objects and obtain the ends and advantages mentioned, as well as those inherent therein. The compositions and methods described herein are representative of preferred embodiments, are exemplary, and are not intended as limitations on the scope of the invention. It is readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

We claim:

1. A cleaning composition comprising an effective amount of an isolated polyol oxidase (POx) comprising an amino acid sequence that is at least about 90% identical to SEQ ID NO:6.

2. The cleaning composition of claim 1, wherein said cleaning composition is a detergent.

3. The cleaning composition of claim 1, further comprising a bleach activator.

4. The cleaning composition of claim 1, further comprising at least one additional enzyme.

5. The cleaning composition of claim 4, wherein said at least one additional enzyme is selected from hemicellulases, peroxidases, proteases, cellulases, xylanases, lipases, phospholipases, esterases, cutinases, pectinases, keratinases, reductases, oxidases, oxidoreductases, perhydrolases, phenoloxidases, lipoxygenases, ligninases, pullulanases, tannases, pentosanases, mannanases, β-glucanases, arabinosidases, hyaluronidases, chondroitinases, laccases, and amylasess, or mixtures thereof.

6. The cleaning composition of claim 4, wherein said at least one additional enzyme is a perhydrolase.

7. The cleaning composition of claim 4, wherein said at least one additional enzyme is a glucose oxidase.

8. The cleaning composition of claim 4, wherein said cleaning composition is a bleaching composition.

9. The cleaning composition of claim 1, wherein said isolated POx comprises the amino acid sequence of SEQ ID NO:6.

10. A method of cleaning, comprising the step of contacting a hard surface and/or an article comprising a fabric with the cleaning composition of claim 1.

11. The method of claim 10, further comprising the step of rinsing said surface and/or article after contacting said surface or article with said cleaning composition.

12. The method of claim 10, wherein said surface and/or article comprising a fabric is stained with a substance containing at least one polyol.

13. The method of claim 12, wherein said polyol is selected from the group consisting of: D-sorbitol, D-xylitol, D-mannitol, D-ribitol, myo-inositol, glycerol, 1,3,-propanediol and 1,2-propanediol.

14. The method of claim 12, wherein said surface and/or said fabric article is soiled with juice, wine and/or tea.

15. The method of claim 10, wherein said cleaning composition comprises an isolated POx comprising the amino acid sequence of SEQ ID NO:6.

* * * * *

SEQUENCE LISTING

```
<160> NUMBER OF SEQ ID NOS: 42

<210> SEQ ID NO 1
<211> LENGTH: 1284
<212> TYPE: DNA
<213> ORGANISM: Streptomyces H-7775

<400> SEQUENCE: 1
ggtacccata tgacccctgc tgaaaaaaac tgggccggca atatcacttt cggtgcaaag      60
agactttgcg ttccacgttc tgtcagagag ctgcgcgaaa cagttgctgc cagtggagca     120
```

```
gtgagacctt tgggaacgcg gcactccttt aacactgtcg ctgacacctc aggtgatcat    180
gtttctttgg ccggtctccc gagagtcgtt gacattgatg tgccaggcag ggctgttagc    240
ctgtcggcag gacttagatt cggtgagttt gctgccgaat tgcatgctcg aggtctcgcc    300
ctggcaaatc tgggctcact tccccacatt tctgtcgctg gggccgtggc aaccggcaca    360
catggaagtg gagtgggtaa ccgttccttg gccggtgctg tcagagcact gagcctcgtt    420
actgctgatg gcgagacacg caccettagg cgtactgacg aagattttgc cggggctgtc    480
gtgtctctgg gcgcattggg agttgtgacg tcgcttgagt tggacctcgt tcctgccttc    540
gaagtcagac agtgggtgta cgaggatctg ccagaagcta cacttgccgc cagatttgac    600
gaggttatgt ccgctgcata tagcgtcagt gtgttcacgg attggagacc gggtcctgtt    660
ggacaagtct ggctcaaaca acgagttggc gacgaagggg ctagatcagt atgcccgcag    720
agtggctggg tgccagattg gctgatggac cacgtcaccc tgttccggga tgccagccgg    780
taattgtact gcacagcaag gcgttccggg cccttggcat gaaagactgc cccacttccg    840
catggaattt accccatcca acggtgacga gttgcagtcg gagtattttg tcgctagggc    900
tgatgccgtt gccgcctacg aagctcttgc acgcctccgc gacagaatcg cacctgtcct    960
gcaagtgtct gagttgcgta cagtcgctgc cgacgatctg tggctttcac cggctcatgg   1020
aagagatagc gtggccttcc actttacctg ggttccagac gctgccgcag tcgctcctgt   1080
ggccggtgca attgaggaag ctctcgcccc ctttggcgca agaccgcatg ggggaaggtt   1140
ttctctactg ctcccgaggt cctgcgaacg ttgtacccac gctatgccga ctttgaggaa   1200
cttgtgggac gtcacgatcc tgaaggcacc ttcaggaacg cctttctcga tcgctacttc   1260
cggcgttaat aaggatccga gctc                                          1284

<210> SEQ ID NO 2
<211> LENGTH: 420
<212> TYPE: PRT
<213> ORGANISM: Streptomyces H-7775

<400> SEQUENCE: 2

Met Thr Pro Ala Glu Lys Asn Trp Ala Gly Asn Ile Thr Phe Gly Ala
1               5                   10                  15

Lys Arg Leu Cys Val Pro Arg Ser Val Arg Glu Leu Arg Glu Thr Val
            20                  25                  30

Ala Ala Ser Gly Ala Val Arg Pro Leu Gly Thr Arg His Ser Phe Asn
        35                  40                  45

Thr Val Ala Asp Thr Ser Gly Asp His Val Ser Leu Ala Gly Leu Pro
    50                  55                  60

Arg Val Val Asp Ile Asp Val Pro Gly Arg Ala Val Ser Leu Ser Ala
65                  70                  75                  80

Gly Leu Arg Phe Gly Glu Phe Ala Ala Glu Leu His Ala Arg Gly Leu
                85                  90                  95

Ala Leu Ala Asn Leu Gly Ser Leu Pro His Ile Ser Val Ala Gly Ala
            100                 105                 110

Val Ala Thr Gly Thr His Gly Ser Gly Val Gly Asn Arg Ser Leu Ala
        115                 120                 125

Gly Ala Val Arg Ala Leu Ser Leu Val Thr Ala Asp Gly Glu Thr Arg
    130                 135                 140

Thr Leu Arg Arg Thr Asp Glu Asp Phe Ala Gly Ala Val Val Ser Leu
145                 150                 155                 160
```

```
Gly Ala Leu Gly Val Val Thr Ser Leu Glu Leu Asp Leu Val Pro Ala
                165                 170                 175

Phe Glu Val Arg Gln Trp Val Tyr Glu Asp Leu Pro Glu Ala Thr Leu
            180                 185                 190

Ala Ala Arg Phe Asp Glu Val Met Ser Ala Ala Tyr Ser Val Ser Val
        195                 200                 205

Phe Thr Asp Trp Arg Pro Gly Pro Val Gly Gln Val Trp Leu Lys Gln
    210                 215                 220

Arg Val Gly Asp Glu Gly Ala Arg Ser Val Met Pro Ala Glu Trp Leu
225                 230                 235                 240

Gly Ala Arg Leu Ala Asp Gly Pro Arg His Pro Val Pro Gly Met Pro
                245                 250                 255

Ala Gly Asn Cys Thr Ala Gln Gln Gly Val Pro Gly Pro Trp His Glu
            260                 265                 270

Arg Leu Pro His Phe Arg Met Glu Phe Thr Pro Ser Asn Gly Asp Glu
        275                 280                 285

Leu Gln Ser Glu Tyr Phe Val Ala Arg Ala Asp Ala Val Ala Ala Tyr
    290                 295                 300

Glu Ala Leu Ala Arg Leu Arg Asp Arg Ile Ala Pro Val Leu Gln Val
305                 310                 315                 320

Ser Glu Leu Arg Thr Val Ala Ala Asp Leu Trp Leu Ser Pro Ala
                325                 330                 335

His Gly Arg Asp Ser Val Ala Phe His Phe Thr Trp Val Pro Asp Ala
                340                 345                 350

Ala Ala Val Ala Pro Val Ala Gly Ala Ile Glu Glu Ala Leu Ala Pro
            355                 360                 365

Phe Gly Ala Arg Pro His Trp Gly Lys Val Phe Ser Thr Ala Pro Glu
    370                 375                 380

Val Leu Arg Thr Leu Tyr Pro Arg Tyr Ala Asp Phe Glu Glu Leu Val
385                 390                 395                 400

Gly Arg His Asp Pro Glu Gly Thr Phe Arg Asn Ala Phe Leu Asp Arg
                405                 410                 415

Tyr Phe Arg Arg
            420

<210> SEQ ID NO 3
<211> LENGTH: 1268
<212> TYPE: DNA
<213> ORGANISM: Artificial
<220> FEATURE:
<223> OTHER INFORMATION: synthetic sequence

<400> SEQUENCE: 3
gccatgggcg acatcacggt caccaactgg gccggcaaca tcacgtacac ggcgaaggaa      60
ctgctgcggc cgcactccct ggacgcgctg cgggccctgg tgcggacag cgccagggtg     120 cgggtgctgg gcagcgggca ctccttcaac gagatcgccg agccgggcga cggggggtgtc    180 ctgctgtcgc tggcgggcct gccgtccgtg gtggacgtgg acacggcggc ccgtacggtg    240
cgggtcggcg gcgtgtgcg gtacgcggag ctggcccggg tggtgcacgc gcggggcctg     300
gcgctgccga acatggcctc gctgccgcac atctcggtcg ccgggtcggt ggccaccggc    360
acccacggtt cggggtgg caacggttcg ctggcctcgg tggtgcgcga ggtggagctg     420
gtcaccgcgg acgttcgac cgtggtgatc gcgcggggcg acgagcggtt cggcggggcg    480
gtgacctcgc tcggcgcgct gggcgtggtg acgtcgctca cactcgacct ggagccggcg    540
```

```
tacgagatgg aacagcacgt cttcaccgag ctgccgctgg ccgggttgga cccggcgacg    600
ttcgagacgg tgatggcggc ggcgtacagc gtgagtctgt tcaccgactg gcgggcgccc    660
ggtttccggc aggtgtggct gaagcggcgc accgaccggc cgctggacgg tttcccgtac    720
gcggccccgg ccgccgagaa gatgcatccg gtgccgggca tgcccgcggt gaactgcacg    780
gagcagttcg gggtgccggg gccctggcac gagcggctgc cgcacttccg cgcggagttc    840
acgcccagca gcgtgccgga gttgcagtcg gagtacctga tgccccggga gcacgccctg    900
gccgccctgc acgcgatgga cgcgatacgg gagacgctcg cgccggtgct ccagacctgc    960
gagatccgca cggtcgccgc cgacgcgcag tggctgagcc cggcgtacgg gcgggacacc   1020
gtggccgcgc acttcacctg ggtcgaggac acggcggcgg tgctgccggt ggtgcggcgg   1080
ctggaggagg cgctcgtccc cttcgcggcc cgtccgcact gggggaaggt gttcaccgtc   1140
ccggcgggcg agctgcgtgc gctgtacccg cggctggccg acttcggggc gctggccggg   1200
gcgctggacc cggcggggaa gttcaccaac gcgttcgtgc gcggggtgct cgcgggctga   1260
ggatccat                                                            1268

<210> SEQ ID NO 4
<211> LENGTH: 418
<212> TYPE: PRT
<213> ORGANISM: Streptomyces lividans

<400> SEQUENCE: 4

Met Gly Asp Ile Thr Val Thr Asn Trp Ala Gly Asn Ile Thr Tyr Thr
1               5                   10                  15

Ala Lys Glu Leu Leu Arg Pro His Ser Leu Asp Ala Leu Arg Ala Leu
            20                  25                  30

Val Ala Asp Ser Ala Arg Val Arg Val Leu Gly Ser Gly His Ser Phe
        35                  40                  45

Asn Glu Ile Ala Glu Pro Gly Asp Gly Val Leu Leu Ser Leu Ala
    50                  55                  60

Gly Leu Pro Ser Val Val Asp Val Asp Thr Ala Ala Arg Thr Val Arg
65                  70                  75                  80

Val Gly Gly Gly Val Arg Tyr Ala Glu Leu Ala Arg Val Val His Ala
                85                  90                  95

Arg Gly Leu Ala Leu Pro Asn Met Ala Ser Leu Pro His Ile Ser Val
            100                 105                 110

Ala Gly Ser Val Ala Thr Gly Thr His Gly Ser Gly Val Gly Asn Gly
        115                 120                 125

Ser Leu Ala Ser Val Val Arg Glu Val Glu Leu Val Thr Ala Asp Gly
    130                 135                 140

Ser Thr Val Val Ile Ala Arg Gly Asp Glu Arg Phe Gly Gly Ala Val
145                 150                 155                 160

Thr Ser Leu Gly Ala Leu Gly Val Val Thr Ser Leu Thr Leu Asp Leu
                165                 170                 175

Glu Pro Ala Tyr Glu Met Glu Gln His Val Phe Thr Glu Leu Pro Leu
            180                 185                 190

Ala Gly Leu Asp Pro Ala Thr Phe Glu Thr Val Met Ala Ala Ala Tyr
        195                 200                 205

Ser Val Ser Leu Phe Thr Asp Trp Arg Ala Pro Gly Phe Arg Gln Val
    210                 215                 220

Trp Leu Lys Arg Arg Thr Asp Arg Pro Leu Asp Gly Pro Phe Pro Tyr Ala
225                 230                 235                 240
```

Ala Pro Ala Ala Glu Lys Met His Pro Val Pro Gly Met Pro Ala Val
            245                 250                 255

Asn Cys Thr Glu Gln Phe Gly Val Pro Gly Pro Trp His Glu Arg Leu
        260                 265                 270

Pro His Phe Arg Ala Glu Phe Thr Pro Ser Ser Gly Ala Glu Leu Gln
    275                 280                 285

Ser Glu Tyr Leu Met Pro Arg Glu His Ala Leu Ala Ala Leu His Ala
290                 295                 300

Met Asp Ala Ile Arg Glu Thr Leu Ala Pro Val Leu Gln Thr Cys Glu
305                 310                 315                 320

Ile Arg Thr Val Ala Ala Asp Ala Gln Trp Leu Ser Pro Ala Tyr Gly
                325                 330                 335

Arg Asp Thr Val Ala Ala His Phe Thr Trp Val Glu Asp Thr Ala Ala
            340                 345                 350

Val Leu Pro Val Val Arg Arg Leu Glu Glu Ala Leu Val Pro Phe Ala
        355                 360                 365

Ala Arg Pro His Trp Gly Lys Val Phe Thr Val Pro Ala Gly Glu Leu
    370                 375                 380

Arg Ala Leu Tyr Pro Arg Leu Ala Asp Phe Gly Ala Leu Ala Gly Ala
385                 390                 395                 400

Leu Asp Pro Ala Gly Lys Phe Thr Asn Ala Phe Val Arg Gly Val Leu
                405                 410                 415

Ala Gly

<210> SEQ ID NO 5
<211> LENGTH: 453
<212> TYPE: PRT
<213> ORGANISM: Acidothermus cellulolyticus

<400> SEQUENCE: 5

Met Asp Gly Gly Lys Arg Cys Arg Asp Gly Thr Pro Gln Pro Pro Ala
1               5                   10                  15

Pro Ser Glu Gln Val Thr Pro Ser Ala Ala Ser Leu Arg Ala Ala
            20                  25                  30

Tyr Asp Val Glu Val Ser Ala Pro Arg Leu Arg Asn Trp Ala Gly Asn
        35                  40                  45

Ile Ala Phe Arg Pro Arg Arg Tyr Val Gln Pro Arg Asp Leu Asp Glu
    50                  55                  60

Leu Val Glu Ile Ile Arg Val Ser Asp Gln Val Arg Val Leu Gly Thr
65                  70                  75                  80

Gly His Ser Phe Asn Pro Ile Ala Asp Thr Thr Gly Thr Leu Ile Ser
                85                  90                  95

Leu Asp His Leu Pro Arg Glu Val Arg Val Met Pro Gly Arg Thr Ala
                100                 105                 110

Val Ser Ala Gly Thr Arg Tyr Gly Asp Leu Ala Phe Pro Leu His Glu
            115                 120                 125

Ala Gly Trp Ala Leu Ala Asn Val Gly Ser Leu Pro His Ile Ser Ile
    130                 135                 140

Ala Gly Ala Cys Ala Thr Ala Thr His Gly Ser Gly Asp Arg Asn Gly
145                 150                 155                 160

Cys Leu Ala Thr Ala Val Ala Gly Met Thr Gly Val Asp Gly Thr Cys
                165                 170                 175

Arg Val Phe His Leu Thr Ala Glu Ser Pro Glu Phe Pro Gly Ala Val
            180                 185                 190

Val His Leu Gly Ala Leu Gly Ala Val Thr Glu Ile Glu Leu Val Thr
            195                 200                 205

Glu Pro Thr Phe Thr Val Arg Gln Trp Val Tyr Glu Asp Ala Pro Leu
    210                 215                 220

Asp Asn Val Phe Ala Asp Leu Asp Asp Val Thr Ser Ala Ala Tyr Ser
225                 230                 235                 240

Val Ser Ile Phe Thr Thr Trp Asp Pro Pro Thr Ala Arg Gln Ile Trp
                245                 250                 255

Leu Lys Glu Arg Val Ala Ala Gly Arg Pro Asp Pro Ala Arg Arg
            260                 265                 270

Trp Gly Gly Arg Leu Ala Glu Arg Asp His Asn Pro Val Pro Gly Met
                275                 280                 285

Pro Pro Glu Asn Cys Thr Pro Gln Leu Gly Arg Ile Gly Pro Trp His
    290                 295                 300

Glu Arg Leu Pro His Phe Arg Leu Asp Val Thr Pro Ser Ala Gly Asp
305                 310                 315                 320

Glu Leu Gln Ser Glu Tyr Phe Val Pro Arg Ala Ala Val Glu Ala
                325                 330                 335

Tyr Arg Ala Leu Arg His Ile Gly Ser Arg Ile Ala Pro Val Leu Gln
                340                 345                 350

Ile Ser Glu Ile Arg Thr Val Ala Ala Asp Glu Leu Trp Leu Ser Pro
            355                 360                 365

Ala Tyr His Arg Pro Ser Val Ala Phe His Phe Thr Trp Ile Ala Asp
                370                 375                 380

Glu Glu Ala Val Arg Pro Val Val Ser Glu Val Glu Arg Ala Leu Ala
385                 390                 395                 400

Pro Leu Gln Pro Arg Pro His Trp Gly Lys Leu Phe Thr Met Asp Pro
                405                 410                 415

Ala Val Val Arg Ala Ala Tyr Pro Arg Phe Asp Asp Phe Val Ala Leu
                420                 425                 430

Ala Glu Arg Tyr Asp Pro Glu Gly Lys Phe Gln Asn Asp Phe Leu Arg
            435                 440                 445

Arg Phe Phe Ala Gly
        450

<210> SEQ ID NO 6
<211> LENGTH: 453
<212> TYPE: PRT
<213> ORGANISM: Acidothermus cellulolyticus 11B

<400> SEQUENCE: 6

Met Asp Gly Gly Lys Arg Cys Arg Asp Gly Thr Pro Gln Pro Pro Ala
1               5                   10                  15

Pro Ser Glu Gln Val Thr Pro Ser Ala Ala Ser Leu Arg Ala Ala
            20                  25                  30

Tyr Asp Val Glu Val Ser Ala Pro Arg Leu Arg Asn Trp Ala Gly Asn
                35                  40                  45

Ile Ala Phe Arg Pro Arg Arg Tyr Val Gln Pro Arg Asp Leu Asp Glu
    50                  55                  60

Leu Val Glu Ile Ile Arg Val Ser Asp Gln Val Arg Val Leu Gly Thr
65                  70                  75                  80

Gly His Ser Phe Asn Pro Ile Ala Asp Thr Thr Gly Thr Leu Ile Ser
                85                  90                  95

Leu Asp His Leu Pro Arg Glu Val Arg Val Met Pro Gly Arg Thr Ala
            100                 105                 110

Val Ser Ala Gly Thr Arg Tyr Gly Asp Leu Ala Phe Pro Leu His Glu
        115                 120                 125

Ala Gly Trp Ala Leu Ala Asn Val Gly Ser Leu Pro His Ile Ser Ile
    130                 135                 140

Ala Gly Ala Cys Ala Thr Ala His Gly Ser Gly Asp Arg Asn Gly
145                 150                 155                 160

Cys Leu Ala Thr Ala Val Ala Gly Met Thr Gly Val Asp Gly Thr Cys
                165                 170                 175

Arg Val Phe His Leu Thr Ala Glu Ser Pro Glu Phe Pro Gly Ala Val
            180                 185                 190

Val His Leu Gly Ala Leu Gly Ala Val Thr Glu Ile Glu Leu Val Thr
        195                 200                 205

Glu Pro Thr Phe Thr Val Arg Gln Trp Val Tyr Glu Asp Ala Pro Leu
    210                 215                 220

Asp Asn Val Phe Ala Asp Leu Asp Asp Val Thr Ser Ala Ala Tyr Ser
225                 230                 235                 240

Val Ser Ile Phe Thr Thr Trp Asp Pro Pro Thr Ala Arg Gln Ile Trp
                245                 250                 255

Leu Lys Glu Arg Val Ala Ala Gly Arg Pro Asp Pro Ala Arg Arg
            260                 265                 270

Trp Gly Gly Arg Leu Ala Glu Arg Asp His Asn Pro Val Pro Gly Met
        275                 280                 285

Pro Pro Glu Asn Cys Thr Pro Gln Leu Gly Arg Ile Gly Pro Trp His
    290                 295                 300

Glu Arg Leu Pro His Phe Arg Leu Asp Val Thr Pro Ser Ala Gly Asp
305                 310                 315                 320

Glu Leu Gln Ser Glu Tyr Phe Val Pro Arg Ala Ala Val Glu Ala
                325                 330                 335

Tyr Arg Ala Leu Arg His Ile Gly Ser Arg Ile Ala Pro Val Leu Gln
            340                 345                 350

Ile Ser Glu Ile Arg Thr Val Ala Ala Asp Glu Leu Trp Leu Ser Pro
        355                 360                 365

Ala Tyr His Arg Pro Ser Val Ala Phe His Phe Thr Trp Ile Ala Asp
    370                 375                 380

Glu Glu Ala Val Arg Pro Val Val Ser Glu Val Glu Arg Ala Leu Ala
385                 390                 395                 400

Pro Leu Gln Pro Arg Pro His Trp Gly Lys Leu Phe Thr Met Asp Pro
                405                 410                 415

Ala Val Val Arg Ala Ala Tyr Pro Arg Phe Asp Asp Phe Val Ala Leu
            420                 425                 430

Ala Glu Arg Tyr Asp Pro Glu Gly Lys Phe Gln Asn Asp Phe Leu Arg
        435                 440                 445

Arg Phe Phe Ala Gly
    450

<210> SEQ ID NO 7
<211> LENGTH: 422
<212> TYPE: PRT
<213> ORGANISM: Streptomyces avermitilis

<400> SEQUENCE: 7

Met Thr Asp Ala Gly Thr Ala Leu Thr Asn Trp Ala Gly Asn Ile Thr
1               5                   10                  15

Tyr Ser Ala Lys Glu Leu His Arg Pro Gln Ser Leu Asp Ala Leu Arg

```
                20                  25                  30
Ala Leu Val Ala Asp Ser Ala Lys Val Arg Val Leu Gly Ser Gly His
            35                  40                  45

Ser Phe Asn Glu Ile Ala Glu Pro Gly Ala Asp Gly Val Leu Leu Ser
 50                  55                  60

Leu Thr Ala Leu Pro Pro Ser Val Glu Val Asp Thr Ala Ala Arg Thr
 65                  70                  75                  80

Val Arg Val Ala Gly Gly Val Arg Tyr Ala Glu Leu Ala Arg Val Val
                85                  90                  95

His Gly His Gly Leu Ala Leu Pro Asn Met Ala Ser Leu Pro His Ile
            100                 105                 110

Ser Val Ala Gly Ser Val Ala Thr Gly Thr His Gly Ser Gly Val Thr
            115                 120                 125

Asn Gly Ser Leu Ala Ser Ala Val Arg Glu Val Glu Leu Val Thr Ala
            130                 135                 140

Asp Gly Ser Ala Val Arg Ile Gly Arg Gly Asp Asp Arg Phe Asp Gly
145                 150                 155                 160

Ala Val Thr Ala Leu Gly Ala Leu Gly Val Val Thr Ala Leu Thr Leu
                165                 170                 175

Asp Leu Glu Pro Asp Tyr Arg Val Ala Gln Gln Val Phe Thr Glu Leu
            180                 185                 190

Pro Leu Ala Gly Leu Asp Phe Asp Ala Val Ala Ser Ala Tyr Ser
            195                 200                 205

Val Ser Leu Phe Thr Gly Trp Arg Thr Ser Gly Phe Ala Gln Val Trp
            210                 215                 220

Leu Lys Arg Arg Thr Asp Arg Pro Ser Ala Asp Phe Pro Trp Ala Ala
225                 230                 235                 240

Pro Ala Thr Glu Ala Met His Pro Val Pro Gly Met Pro Ala Val Asn
                245                 250                 255

Cys Thr Gln Gln Phe Gly Val Pro Gly Pro Trp His Glu Arg Leu Pro
            260                 265                 270

His Phe Arg Ala Glu Phe Thr Pro Ser Ser Gly Ala Glu Leu Gln Ser
            275                 280                 285

Glu Tyr Leu Leu Pro Arg Pro Tyr Ala Leu Asp Ala Leu His Ala Leu
            290                 295                 300

Asp Ala Val Arg Glu Thr Val Ala Pro Val Leu Gln Ile Cys Glu Val
305                 310                 315                 320

Arg Thr Val Ala Ala Asp Ala Gln Trp Leu Ser Pro Ala Tyr Gly Arg
                325                 330                 335

Asp Thr Val Ala Leu His Phe Thr Trp Val Glu Asp Leu Ala Ala Val
            340                 345                 350

Leu Pro Val Val Arg Arg Val Glu Glu Ala Leu Asp Pro Phe Asp Pro
            355                 360                 365

Arg Pro His Trp Gly Lys Val Phe Ala Val Pro Ala Arg Val Leu Arg
            370                 375                 380

Gly Arg Tyr Pro Arg Leu Gly Asp Phe Arg Ala Leu Val Asp Ser Leu
385                 390                 395                 400

Asp Pro Gly Gly Lys Phe Thr Asn Ala Phe Val Arg Glu Val Leu Gly
                405                 410                 415

Ser Gly Asp Arg Pro Ser
            420

<210> SEQ ID NO 8
```

<211> LENGTH: 422
<212> TYPE: PRT
<213> ORGANISM: Streptomyces avermitilis

<400> SEQUENCE: 8

```
Met Thr Asp Ala Gly Thr Ala Leu Thr Asn Trp Ala Gly Asn Ile Thr
1               5                   10                  15

Tyr Ser Ala Lys Glu Leu His Arg Pro Gln Ser Leu Asp Ala Leu Arg
            20                  25                  30

Ala Leu Val Ala Asp Ser Ala Lys Val Arg Val Leu Gly Ser Gly His
        35                  40                  45

Ser Phe Asn Glu Ile Ala Glu Pro Gly Ala Asp Gly Val Leu Leu Ser
    50                  55                  60

Leu Thr Ala Leu Pro Pro Ser Val Glu Val Asp Thr Ala Ala Arg Thr
65                  70                  75                  80

Val Arg Val Ala Gly Val Arg Tyr Ala Glu Leu Ala Arg Val Val
                85                  90                  95

His Gly His Gly Leu Ala Leu Pro Asn Met Ala Ser Leu Pro His Ile
                100                 105                 110

Ser Val Ala Gly Ser Val Ala Thr Gly Thr His Gly Ser Gly Val Thr
            115                 120                 125

Asn Gly Ser Leu Ala Ser Ala Val Arg Glu Val Glu Leu Val Thr Ala
    130                 135                 140

Asp Gly Ser Ala Val Arg Ile Gly Arg Gly Asp Arg Phe Asp Gly
145                 150                 155                 160

Ala Val Thr Ala Leu Gly Ala Leu Gly Val Val Thr Ala Leu Thr Leu
                165                 170                 175

Asp Leu Glu Pro Asp Tyr Arg Val Ala Gln Gln Val Phe Thr Glu Leu
            180                 185                 190

Pro Leu Ala Gly Leu Asp Phe Asp Ala Val Ala Ala Ser Ala Tyr Ser
        195                 200                 205

Val Ser Leu Phe Thr Gly Trp Arg Thr Ser Gly Phe Ala Gln Val Trp
    210                 215                 220

Leu Lys Arg Arg Thr Asp Arg Pro Ser Ala Asp Phe Pro Trp Ala Ala
225                 230                 235                 240

Pro Ala Thr Glu Ala Met His Pro Val Pro Gly Met Pro Ala Val Asn
                245                 250                 255

Cys Thr Gln Gln Phe Gly Val Pro Gly Pro Trp His Glu Arg Leu Pro
            260                 265                 270

His Phe Arg Ala Glu Phe Thr Pro Ser Ser Gly Ala Glu Leu Gln Ser
        275                 280                 285

Glu Tyr Leu Leu Pro Arg Pro Tyr Ala Leu Asp Ala Leu His Ala Leu
    290                 295                 300

Asp Ala Val Arg Glu Thr Val Ala Pro Val Leu Gln Ile Cys Glu Val
305                 310                 315                 320

Arg Thr Val Ala Ala Asp Ala Gln Trp Leu Ser Pro Ala Tyr Gly Arg
                325                 330                 335

Asp Thr Val Ala Leu His Phe Thr Trp Val Glu Asp Leu Ala Ala Val
            340                 345                 350

Leu Pro Val Val Arg Arg Val Glu Ala Leu Asp Pro Phe Asp Pro
        355                 360                 365

Arg Pro His Trp Gly Lys Val Phe Ala Val Pro Ala Arg Val Leu Arg
    370                 375                 380

Gly Arg Tyr Pro Arg Leu Gly Asp Phe Arg Ala Leu Val Asp Ser Leu
```

```
                385                 390                 395                 400
Asp Pro Gly Gly Lys Phe Thr Asn Ala Phe Val Arg Glu Val Leu Gly
                    405                 410                 415
Ser Gly Asp Arg Pro Ser
                420
```

<210> SEQ ID NO 9
<211> LENGTH: 418
<212> TYPE: PRT
<213> ORGANISM: Streptomyces coelicolor

<400> SEQUENCE: 9

```
Met Ser Asp Ile Thr Val Thr Asn Trp Ala Gly Asn Ile Thr Tyr Thr
1               5                   10                  15
Ala Lys Glu Leu Leu Arg Pro His Ser Leu Asp Ala Leu Arg Ala Leu
                20                  25                  30
Val Ala Asp Ser Ala Arg Val Arg Val Leu Gly Ser Gly His Ser Phe
            35                  40                  45
Asn Glu Ile Ala Glu Pro Gly Asp Gly Val Leu Leu Ser Leu Ala
        50                  55                  60
Gly Leu Pro Ser Val Val Asp Val Asp Thr Ala Ala Arg Thr Val Arg
65                  70                  75                  80
Val Gly Gly Val Arg Tyr Ala Glu Leu Ala Arg Val Val His Ala
                85                  90                  95
Arg Gly Leu Ala Leu Pro Asn Met Ala Ser Leu Pro His Ile Ser Val
                100                 105                 110
Ala Gly Ser Val Ala Thr Gly Thr His Gly Ser Gly Val Gly Asn Gly
                115                 120                 125
Ser Leu Ala Ser Val Val Arg Glu Val Glu Leu Val Thr Ala Asp Gly
            130                 135                 140
Ser Thr Val Val Ile Ala Arg Gly Asp Glu Arg Phe Gly Gly Ala Val
145                 150                 155                 160
Thr Ser Leu Gly Ala Leu Gly Val Val Thr Ser Leu Thr Leu Asp Leu
                165                 170                 175
Glu Pro Ala Tyr Glu Met Glu Gln His Val Phe Thr Glu Leu Pro Leu
                180                 185                 190
Ala Gly Leu Asp Pro Ala Thr Phe Glu Thr Val Met Ala Ala Ala Tyr
            195                 200                 205
Ser Val Ser Leu Phe Thr Asp Trp Arg Ala Pro Gly Phe Arg Gln Val
        210                 215                 220
Trp Leu Lys Arg Arg Thr Asp Arg Pro Leu Asp Gly Phe Pro Tyr Ala
225                 230                 235                 240
Ala Pro Ala Ala Glu Lys Met His Pro Val Pro Gly Met Pro Ala Val
                245                 250                 255
Asn Cys Thr Glu Gln Phe Gly Val Pro Gly Pro Trp His Glu Arg Leu
                260                 265                 270
Pro His Phe Arg Ala Glu Phe Thr Pro Ser Ser Gly Ala Glu Leu Gln
            275                 280                 285
Ser Glu Tyr Leu Met Pro Arg Glu His Ala Leu Ala Ala Leu His Ala
        290                 295                 300
Met Asp Ala Ile Arg Glu Thr Leu Ala Pro Val Leu Gln Thr Cys Glu
305                 310                 315                 320
Ile Arg Thr Val Ala Ala Asp Ala Gln Trp Leu Ser Pro Ala Tyr Gly
                325                 330                 335
```

```
Arg Asp Thr Val Ala Ala His Phe Thr Trp Val Glu Asp Thr Ala Ala
            340                 345                 350

Val Leu Pro Val Arg Arg Leu Glu Glu Ala Leu Val Pro Phe Ala
        355                 360                 365

Ala Arg Pro His Trp Gly Lys Val Phe Thr Val Pro Ala Gly Glu Leu
    370                 375                 380

Arg Ala Leu Tyr Pro Arg Leu Ala Asp Phe Gly Ala Leu Ala Gly Ala
385                 390                 395                 400

Leu Asp Pro Ala Gly Lys Phe Thr Asn Ala Phe Val Arg Gly Val Leu
                405                 410                 415

Ala Gly

<210> SEQ ID NO 10
<211> LENGTH: 415
<212> TYPE: PRT
<213> ORGANISM: Streptomyces 1KD472

<400> SEQUENCE: 10

Met Ser Thr Ala Val Thr Asn Trp Ala Gly Asn Ile Thr Tyr Thr Ala
1               5                   10                  15

Lys Glu Val His Arg Pro Ala Thr Ala Glu Glu Leu Ala Asp Val Val
            20                  25                  30

Ala Arg Ser Ala Trp Gly Ala Cys Ala Gly Ala Ala Gly His Ser Phe
        35                  40                  45

Asn Glu Ile Ala Asp Pro Gly Pro Asp Gly Val Leu Leu Arg Leu Asp
    50                  55                  60

Ala Leu Pro Ala Glu Thr Asp Val Asp Thr Thr Ala Arg Thr Val Arg
65                  70                  75                  80

Val Gly Gly Gly Val Arg Tyr Ala Glu Leu Ala Arg Val Val His Ala
                85                  90                  95

His Gly Leu Ala Leu Pro Asn Met Ala Ser Leu Pro His Ile Ser Val
            100                 105                 110

Ala Gly Ser Val Ala Thr Gly Thr His Gly Ser Gly Val Thr Asn Gly
        115                 120                 125

Pro Leu Ala Ala Pro Val Arg Glu Val Glu Leu Val Thr Ala Asp Gly
    130                 135                 140

Ser Gln Val Arg Ile Ala Pro Gly Glu Arg Arg Phe Gly Gly Ala Val
145                 150                 155                 160

Thr Ser Leu Gly Ala Leu Gly Val Val Thr Ala Leu Thr Leu Asp Leu
                165                 170                 175

Glu Pro Ala Phe Glu Val Gly Gln His Leu Phe Thr Glu Leu Pro Leu
            180                 185                 190

Arg Gly Leu Asp Phe Glu Thr Val Ala Ala Ala Gly Tyr Ser Val Ser
        195                 200                 205

Leu Phe Thr Asp Trp Arg Glu Pro Gly Phe Arg Gln Val Trp Leu Lys
    210                 215                 220

Arg Arg Thr Asp Gln Glu Leu Pro Asp Phe Pro Trp Ala Arg Pro Ala
225                 230                 235                 240

Thr Val Ala Leu His Pro Val Pro Gly Met Pro Ala Glu Asn Cys Thr
                245                 250                 255

Gln Gln Phe Gly Val Pro Gly Pro Trp His Glu Arg Leu Pro His Phe
            260                 265                 270

Arg Ala Glu Phe Thr Pro Ser Ser Gly Ala Glu Leu Gln Ser Glu Tyr
        275                 280                 285
```

```
Leu Leu Pro Arg Ala His Ala Leu Asp Ala Leu Asp Ala Val Asp Arg
    290                 295                 300

Ile Arg Asp Thr Val Ala Pro Val Leu Gln Thr Cys Glu Val Arg Thr
305                 310                 315                 320

Val Ala Pro Asp Glu Gln Trp Leu Gly Pro Ser His Gly Arg Asp Thr
                325                 330                 335

Val Ala Leu His Phe Thr Trp Val Lys Asp Thr Glu Ala Val Leu Pro
                340                 345                 350

Val Val Arg Arg Leu Glu Glu Ala Leu Asp Ala Phe Asp Pro Arg Pro
                355                 360                 365

His Trp Gly Lys Val Phe Thr Thr Ser Ala Ala Leu Arg Ala Arg
    370                 375                 380

Tyr Pro Arg Leu Ala Asp Phe Arg Ala Leu Ala Arg Glu Leu Asp Pro
385                 390                 395                 400

Ser Gly Lys Phe Thr Asn Thr Phe Leu Arg Asp Leu Leu Asp Gly
                405                 410                 415

<210> SEQ ID NO 11
<211> LENGTH: 449
<212> TYPE: PRT
<213> ORGANISM: Arthrobacter FB24

<400> SEQUENCE: 11

Met Arg Thr Val Ser Glu Leu Pro Gly Leu Ser Gly Ser Thr Gly Ala
1               5                   10                  15

Gly Ser Ser Ala Pro Glu Leu Asn Trp Ala Gly Asn Tyr Arg Tyr Thr
                20                  25                  30

Ala Ala Ser Ile His Arg Pro Arg Thr Leu Glu Glu Val Gln Glu Val
                35                  40                  45

Val Ala Gly Ala Ser Lys Ile Arg Ala Leu Gly Ser Arg His Ser Phe
50                  55                  60

Asn Ala Ile Ala Asp Ser Pro Gly Ser Leu Val Ser Leu Glu Asp Leu
65                  70                  75                  80

Asp Pro Gly Ile Arg Ile Asp Ala Ala Thr Arg Thr Val Thr Val Ser
                85                  90                  95

Gly Gly Thr Arg Tyr Gly Thr Leu Ala Glu Gln Leu Glu Ser Ala Gly
                100                 105                 110

Phe Ala Leu Ser Asn Leu Ala Ser Leu Pro His Ile Ser Val Ala Gly
            115                 120                 125

Ala Ile Ala Thr Ala Thr His Gly Ser Gly Asp Ala Asn Gly Asn Leu
130                 135                 140

Ala Thr Ser Val Ala Ala Leu Glu Leu Val Ala Ala Asp Gly Thr Val
145                 150                 155                 160

His Arg Leu Asn Arg Gly Ser Ser Pro Gly Phe Asp Gly Ala Val Val
                165                 170                 175

Gly Leu Gly Ala Leu Gly Val Val Thr Lys Val Thr Leu Asp Ile Glu
            180                 185                 190

Pro Thr Phe Thr Val Arg Gln Asp Val Phe Glu Ala Leu Pro Trp Asp
            195                 200                 205

Thr Val Leu Gly Asn Phe Asp Ala Val Thr Ser Ser Ala Tyr Ser Val
        210                 215                 220

Ser Leu Phe Thr Asp Trp Ser Gly Asp Val Ala Gln Ala Trp Leu
225                 230                 235                 240

Lys Ser Arg Leu Ser Gly Ser Ala Ala Ser Ser Asp Ala Gly Ser Thr
                245                 250                 255
```

```
Leu Ala Gly Glu Ala Phe Ala Ala Gly Thr Phe Phe Gly Gly Thr Arg
            260                 265                 270

Ala Gly Val Ala Arg His Pro Leu Pro Gly Val Ser Ala Glu Asn Cys
        275                 280                 285

Thr Glu Gln Leu Gly Val Pro Gly Ser Trp Ser Glu Arg Leu Ala His
    290                 295                 300

Phe Arg Met Ala Phe Thr Pro Ser Ser Gly Glu Glu Leu Gln Ser Glu
305                 310                 315                 320

Phe Phe Val Arg Arg Glu His Ala Val Ala Ala Ile Gly Glu Leu Arg
                325                 330                 335

Ala Leu Ser Asp Arg Ile Thr Pro Leu Leu Leu Val Ser Glu Ile Arg
            340                 345                 350

Thr Val Ala Ala Asp Lys Leu Trp Leu Ser Thr Ala Tyr Gly Gln Asp
        355                 360                 365

Ser Val Gly Phe His Phe Thr Trp Lys Gln Arg Gln Asp Glu Val Glu
    370                 375                 380

Lys Val Leu Pro Val Met Glu Glu Ala Leu Ala Pro Phe Asn Ala Arg
385                 390                 395                 400

Pro His Trp Gly Lys Leu Phe His Ala Gly Ala Asp Ala Val Ala Glu
                405                 410                 415

Leu Tyr Pro Arg Phe Ser Asp Phe Lys Asp Leu Ala Glu Arg Met Asp
            420                 425                 430

Pro Glu Gln Lys Phe Arg Asn Glu Phe Leu Ala Arg Lys Val Phe Gly
            435                 440                 445

Asn

<210> SEQ ID NO 12
<211> LENGTH: 449
<212> TYPE: PRT
<213> ORGANISM: Arthrobacter FB24

<400> SEQUENCE: 12

Met Arg Thr Val Ser Glu Leu Pro Gly Leu Ser Gly Ser Thr Gly Ala
1               5                   10                  15

Gly Ser Ser Ala Pro Glu Leu Asn Trp Ala Gly Asn Tyr Arg Tyr Thr
            20                  25                  30

Ala Ala Ser Ile His Arg Pro Arg Thr Leu Glu Glu Val Gln Glu Val
        35                  40                  45

Val Ala Gly Ala Ser Lys Ile Arg Ala Leu Gly Ser Arg His Ser Phe
    50                  55                  60

Asn Ala Ile Ala Asp Ser Pro Gly Ser Leu Val Ser Leu Glu Asp Leu
65                  70                  75                  80

Asp Pro Gly Ile Arg Ile Asp Ala Ala Thr Arg Thr Val Thr Val Ser
                85                  90                  95

Gly Gly Thr Arg Tyr Gly Thr Leu Ala Glu Gln Leu Glu Ser Ala Gly
            100                 105                 110

Phe Ala Leu Ser Asn Leu Ala Ser Leu Pro His Ile Ser Val Ala Gly
        115                 120                 125

Ala Ile Ala Thr Ala Thr His Gly Ser Gly Asp Ala Asn Gly Asn Leu
    130                 135                 140

Ala Thr Ser Val Ala Ala Leu Glu Leu Val Ala Ala Asp Gly Thr Val
145                 150                 155                 160

His Arg Leu Asn Arg Gly Ser Ser Pro Gly Phe Asp Gly Ala Val Val
                165                 170                 175
```

```
Gly Leu Gly Ala Leu Gly Val Val Thr Lys Val Thr Leu Asp Ile Glu
            180                 185                 190

Pro Thr Phe Thr Val Arg Gln Asp Val Phe Glu Ala Leu Pro Trp Asp
        195                 200                 205

Thr Val Leu Gly Asn Phe Asp Ala Val Thr Ser Ser Ala Tyr Ser Val
    210                 215                 220

Ser Leu Phe Thr Asp Trp Ser Gly Asp Val Ala Gln Ala Trp Leu
225                 230                 235                 240

Lys Ser Arg Leu Ser Gly Ser Ala Ala Ser Ser Asp Ala Gly Ser Thr
                245                 250                 255

Leu Ala Gly Glu Ala Phe Ala Ala Gly Thr Phe Phe Gly Gly Thr Arg
            260                 265                 270

Ala Gly Val Ala Arg His Pro Leu Pro Gly Val Ser Ala Glu Asn Cys
        275                 280                 285

Thr Glu Gln Leu Gly Val Pro Gly Ser Trp Ser Glu Arg Leu Ala His
    290                 295                 300

Phe Arg Met Ala Phe Thr Pro Ser Ser Gly Glu Leu Gln Ser Glu
305                 310                 315                 320

Phe Phe Val Arg Arg Glu His Ala Val Ala Ile Gly Glu Leu Arg
                325                 330                 335

Ala Leu Ser Asp Arg Ile Thr Pro Leu Leu Val Ser Glu Ile Arg
            340                 345                 350

Thr Val Ala Ala Asp Lys Leu Trp Leu Ser Thr Ala Tyr Gly Gln Asp
        355                 360                 365

Ser Val Gly Phe His Phe Thr Trp Lys Gln Arg Gln Asp Glu Val Glu
    370                 375                 380

Lys Val Leu Pro Val Met Glu Glu Ala Leu Ala Pro Phe Asn Ala Arg
385                 390                 395                 400

Pro His Trp Gly Lys Leu Phe His Ala Gly Ala Asp Ala Val Ala Glu
                405                 410                 415

Leu Tyr Pro Arg Phe Ser Asp Phe Lys Asp Leu Ala Glu Arg Met Asp
            420                 425                 430

Pro Glu Gln Lys Phe Arg Asn Glu Phe Leu Ala Arg Lys Val Phe Gly
        435                 440                 445

Asn

<210> SEQ ID NO 13
<211> LENGTH: 417
<212> TYPE: PRT
<213> ORGANISM: Actinobacterium PHSC20C1

<400> SEQUENCE: 13

Met Leu Thr Asn Gln Thr Asn Trp Ala Gly Asn Leu Tyr Asn Ala
1               5                   10                  15

Lys Ala Ile Met Gln Pro Thr Asn Val Asp Glu Leu Gln Glu Leu Val
                20                  25                  30

Ala Arg Leu Pro Arg Val Arg Ala Leu Gly Thr Arg His Ser Phe Thr
            35                  40                  45

Asp Ile Ala Asp Thr Pro Gly Thr Leu Met Ser Leu Ala Asn Met Pro
        50                  55                  60

Pro Asn Ile His Ile Asp Thr Thr Ala Met Thr Ala Ser Val Thr Gly
65                  70                  75                  80

Gly Thr Ser Tyr Gly Leu Leu Met Ser Glu Leu Gln Ser Asn Gly Phe
                85                  90                  95
```

-continued

```
Ala Leu His Asn Thr Gly Ser Leu Pro His Ile Ser Val Ala Gly Ala
            100                 105                 110

Thr Ala Thr Ala Thr His Gly Ser Gly Asp Gly Asn Gly Ile Leu Ser
        115                 120                 125

Thr Ala Ile Ala Ala Leu Asp Val Val Thr Ala Asp Gly Ser Leu Val
    130                 135                 140

Thr Val Asp Arg Ala Ser Asp His Leu Pro Ala Leu Ala Val Gly Leu
145                 150                 155                 160

Gly Ala Phe Gly Val Ile Ala Arg Val Thr Leu Asp Ile Glu Pro Thr
                165                 170                 175

Tyr Arg Val Arg Gln Asp Val Tyr Arg Phe Ala Pro Trp Glu Thr Val
            180                 185                 190

Leu Glu Gln Leu Asp Asp Ile Met Ala Ser Ala Tyr Ser Val Ser Leu
        195                 200                 205

Leu Ala Asp Phe Gly Ser Pro Thr Val Ala Gln Ile Trp Leu Lys Thr
    210                 215                 220

Arg Leu Gly Val Gly Asp Asp Pro Glu Val Ala Pro Thr Leu Phe Gly
225                 230                 235                 240

Gly Ile Trp Tyr Asp Asp Ser Asp Glu Leu Ala Pro Gln Asn Val Asn
                245                 250                 255

Gln Arg Ala Ser Ile Pro Gly Pro Trp Ser Glu Arg Met Pro His Phe
            260                 265                 270

Arg Leu Asp Gly Glu Pro Ser Asn Gly Gly Asp Glu Leu Gln Ser Glu
        275                 280                 285

Tyr Tyr Val Arg Arg Glu His Gly Val Gln Ala Leu Glu Ala Leu Arg
    290                 295                 300

Gly Leu Gly Ala Gln Ile Ser Pro His Leu Leu Ile Ser Glu Ile Arg
305                 310                 315                 320

Thr Ala Ala Ala Asp Ser Leu Trp Met Ser Pro Ala Tyr Gly Gln Asp
                325                 330                 335

Val Leu Cys Ile Gly Phe Thr Trp Ala Lys His Pro Ala Glu Val Thr
            340                 345                 350

Ala Leu Leu Pro Glu Ile Glu Ala Thr Leu Ala Pro Phe Ala Pro Arg
        355                 360                 365

Gln His Trp Gly Lys Leu Phe Ser Phe Ser Arg Asp Ile Ile Ala Glu
    370                 375                 380

Arg Phe Pro Arg Val Ala Asp Phe Thr Glu Leu Arg Asp Gln Tyr Asp
385                 390                 395                 400

Pro Gln Arg Lys Phe Trp Asn Pro Phe Leu Glu Arg Thr Leu Gly Ala
                405                 410                 415

Pro
```

<210> SEQ ID NO 14
<211> LENGTH: 415
<212> TYPE: PRT
<213> ORGANISM: Streptomyces 1KD472

<400> SEQUENCE: 14

```
Met Ser Thr Ala Val Thr Asn Trp Ala Gly Asn Ile Tyr Thr Ala
1               5                   10                  15

Lys Glu Val His Arg Pro Ala Thr Ala Glu Glu Leu Ala Asp Val Val
            20                  25                  30

Ala Arg Ser Ala Trp Gly Ala Cys Ala Gly Ala Ala Gly His Ser Phe
        35                  40                  45
```

Asn Glu Ile Ala Asp Pro Gly Pro Asp Gly Val Leu Leu Arg Leu Asp
    50                  55                  60

Ala Leu Pro Ala Glu Thr Asp Val Asp Thr Thr Ala Arg Thr Val Arg
 65                  70                  75                  80

Val Gly Gly Gly Val Arg Tyr Ala Glu Leu Ala Arg Val Val His Ala
                 85                  90                  95

His Gly Leu Ala Leu Pro Asn Met Ala Ser Leu Pro His Ile Ser Val
             100                 105                 110

Ala Gly Ser Val Ala Thr Gly Thr His Gly Ser Gly Val Thr Asn Gly
         115                 120                 125

Pro Leu Ala Ala Pro Val Arg Glu Val Glu Leu Val Thr Ala Asp Gly
    130                 135                 140

Ser Gln Val Arg Ile Ala Pro Gly Glu Arg Arg Phe Gly Gly Ala Val
145                 150                 155                 160

Thr Ser Leu Gly Ala Leu Gly Val Val Thr Ala Leu Thr Leu Asp Leu
                165                 170                 175

Glu Pro Ala Phe Glu Val Gly Gln His Leu Phe Thr Glu Leu Pro Leu
            180                 185                 190

Arg Gly Leu Asp Phe Glu Thr Val Ala Ala Ala Gly Tyr Ser Val Ser
        195                 200                 205

Leu Phe Thr Asp Trp Arg Glu Pro Gly Phe Arg Gln Val Trp Leu Lys
    210                 215                 220

Arg Arg Thr Asp Gln Glu Leu Pro Asp Phe Pro Trp Ala Arg Pro Ala
225                 230                 235                 240

Thr Val Ala Leu His Pro Val Pro Gly Met Pro Ala Glu Asn Cys Thr
                245                 250                 255

Gln Gln Phe Gly Val Pro Gly Pro Trp His Glu Arg Leu Pro His Phe
            260                 265                 270

Arg Ala Glu Phe Thr Pro Ser Ser Gly Ala Glu Leu Gln Ser Glu Tyr
        275                 280                 285

Leu Leu Pro Arg Ala His Ala Leu Asp Ala Leu Asp Ala Val Asp Arg
    290                 295                 300

Ile Arg Asp Thr Val Ala Pro Val Leu Gln Thr Cys Gly Val Arg Thr
305                 310                 315                 320

Val Ala Pro Asp Glu Gln Trp Leu Gly Pro Ser His Gly Arg Asp Thr
                325                 330                 335

Val Ala Leu His Phe Thr Trp Val Lys Asp Thr Glu Ala Val Leu Pro
            340                 345                 350

Val Val Arg Arg Leu Glu Glu Ala Leu Asp Ala Phe Asp Pro Arg Pro
        355                 360                 365

His Trp Gly Lys Val Phe Thr Thr Ser Ala Ala Leu Arg Ala Arg
    370                 375                 380

Tyr Pro Arg Leu Ala Asp Phe Arg Ala Leu Ala Arg Glu Leu Asp Pro
385                 390                 395                 400

Ser Gly Lys Phe Thr Asn Thr Phe Leu Arg Asp Leu Leu Asp Gly
                405                 410                 415

<210> SEQ ID NO 15
<211> LENGTH: 47
<212> TYPE: PRT
<213> ORGANISM: Streptomyces coelicolor

<400> SEQUENCE: 15

Met Thr Glu Val Ser Arg Arg Lys Leu Met Lys Gly Ala Ala Val Ser

```
                 1               5                  10                 15
Gly Gly Ala Leu Ala Leu Pro Ala Leu Gly Ala Pro Pro Ala Thr Ala
                20                  25                 30

Ala Pro Ala Ala Gly Pro Glu Asp Leu Pro Gly Pro Ala Ala Ala
       35                  40                 45

<210> SEQ ID NO 16
<211> LENGTH: 468
<212> TYPE: PRT
<213> ORGANISM: Artificial
<220> FEATURE:
<223> OTHER INFORMATION: synthetic fusion protein

<400> SEQUENCE: 16

Met Gly Thr Glu Val Ser Arg Arg Lys Leu Met Lys Gly Ala Ala Val
1               5                   10                  15

Ser Gly Gly Ala Leu Ala Leu Pro Ala Leu Gly Ala Pro Pro Ala Thr
                20                  25                  30

Ala Ala Pro Ala Ala Gly Pro Glu Asp Leu Pro Gly Pro Ala Ala Ala
            35                  40                  45

Met Thr Pro Ala Glu Lys Asn Trp Ala Gly Asn Ile Thr Phe Gly Ala
50                  55                  60

Lys Arg Leu Cys Val Pro Arg Ser Val Arg Glu Leu Arg Glu Thr Val
65                  70                  75                  80

Ala Ala Ser Gly Ala Val Arg Pro Leu Gly Thr Arg His Ser Phe Asn
                85                  90                  95

Thr Val Ala Asp Thr Ser Gly Asp His Val Ser Leu Ala Gly Leu Pro
            100                 105                 110

Arg Val Val Asp Ile Asp Val Pro Gly Arg Ala Val Ser Leu Ser Ala
        115                 120                 125

Gly Leu Arg Phe Gly Glu Phe Ala Ala Glu Leu His Ala Arg Gly Leu
    130                 135                 140

Ala Leu Ala Asn Leu Gly Ser Leu Pro His Ile Ser Val Ala Gly Ala
145                 150                 155                 160

Val Ala Thr Gly Thr His Gly Ser Gly Val Gly Asn Arg Ser Leu Ala
                165                 170                 175

Gly Ala Val Arg Ala Leu Ser Leu Val Thr Ala Asp Gly Glu Thr Arg
            180                 185                 190

Thr Leu Arg Arg Thr Asp Glu Asp Phe Ala Gly Ala Val Val Ser Leu
        195                 200                 205

Gly Ala Leu Gly Val Val Thr Ser Leu Glu Leu Asp Leu Val Pro Ala
    210                 215                 220

Phe Glu Val Arg Gln Trp Val Tyr Glu Asp Leu Pro Glu Ala Thr Leu
225                 230                 235                 240

Ala Ala Arg Phe Asp Glu Val Met Ser Ala Ala Tyr Ser Val Ser Val
                245                 250                 255

Phe Thr Asp Trp Arg Pro Gly Pro Val Gly Gln Val Trp Leu Lys Gln
            260                 265                 270

Arg Val Gly Asp Glu Gly Ala Arg Ser Val Met Pro Ala Glu Trp Leu
        275                 280                 285

Gly Ala Arg Leu Ala Asp Gly Pro Arg His Pro Val Pro Gly Met Pro
    290                 295                 300

Ala Gly Asn Cys Thr Ala Gln Gln Gly Val Pro Gly Pro Trp His Glu
305                 310                 315                 320

Arg Leu Pro His Phe Arg Met Glu Phe Thr Pro Ser Asn Gly Asp Glu
```

```
                     325                 330                 335
Leu Gln Ser Glu Tyr Phe Val Ala Arg Ala Asp Ala Val Ala Ala Tyr
            340                 345                 350

Glu Ala Leu Ala Arg Leu Arg Asp Arg Ile Ala Pro Val Leu Gln Val
            355                 360                 365

Ser Glu Leu Arg Thr Val Ala Ala Asp Asp Leu Trp Leu Ser Pro Ala
        370                 375                 380

His Gly Arg Asp Ser Val Ala Phe His Phe Thr Trp Val Pro Asp Ala
385                 390                 395                 400

Ala Ala Val Ala Pro Val Ala Gly Ala Ile Glu Glu Ala Leu Ala Pro
                405                 410                 415

Phe Gly Ala Arg Pro His Trp Gly Lys Val Phe Ser Thr Ala Pro Glu
            420                 425                 430

Val Leu Arg Thr Leu Tyr Pro Arg Tyr Ala Asp Phe Glu Glu Leu Val
            435                 440                 445

Gly Arg His Asp Pro Glu Gly Thr Phe Arg Asn Ala Phe Leu Asp Arg
        450                 455                 460

Tyr Phe Arg Arg
465

<210> SEQ ID NO 17
<211> LENGTH: 1415
<212> TYPE: DNA
<213> ORGANISM: Artificial
<220> FEATURE:
<223> OTHER INFORMATION: synthetic sequence

<400> SEQUENCE: 17
ccatgggcac cgaggtctcc cgccgcaagc tgatgaaggg cgcggcggtg tcgggcggcg      60
cgctggcgct gccggccctc ggcgccccgc ccgccaccgc ggcgcggcc gccggccccg     120 aggacctccc gggccccgcc gccgccatga ccccggccga aagaactgg gccggcaaca     180 tcaccttcgg cgccaagcgc ctgtgcgtcc cgcgctccgt ccgcgagctg cgcgagaccg     240
tggccgcctc cggcgccgtg cgcccgctgg gcacccgcca ctcgttcaac accgtcgccg     300
acacctccgg cgaccacgtg tcgctggccg gcctgccgcg cgtcgtcgac atcgacgtcc     360
cgggccgggc cgtgtccctg tccgccggcc tgcgcttcgg cgagttcgcc gccgagctgc     420
acgcccgcgg cctggccctg ccaacctgg gctccctgcc gcacatctcc gtggcgggcg     480
cggtcgccac cggcacccac ggctccggcg tcggcaaccg ctccctggcg ggcgccgtcc     540
gcgccctgtc cctggtcacc gccgacggcg agacccgcac cctgcgccgc accgacgagg     600
acttcgccgg cgccgtcgtg tccctgggcg ccctgggcgt cgtcacctcc ctggagctgg     660
acctggtccc ggccttcgag gtccgccagt gggtctacga ggacctgccc gaggccaccc     720
tggccgcccg cttcgacgag gtcatgtccg ccgcctactc cgtgtccgtg ttcaccgact     780
ggcgccgggg ccggtcggc caggtctggc tgaagcagcg cgtcggcgac gagggcgccc     840
gctccgtcat gccggccgag tggctggcg cccgcctggc cgacggcccg cgccacccgg     900
tccccggcat gcccgccggc aactgcaccg cccagcaggg cgtccccggc ccgtggcacg     960
agcgcctgcc gcacttccgc atggagttca cccccgtcca cggcgacgag ctgcagtccg    1020
agtacttcgt cgcccgcgcg gacgccgtcg cggcctacga ggcgctggcc cgcctgcgcg    1080
accgcatcgc cccggtcctg caggtctccg agctgcgcac cgtcgccgcc gacgacctgt    1140
ggctgtcccc ggcccacggc cgcgactccg tcgccttcca cttcacctgg gtcccggacg    1200
```

```
ccgccgccgt cgccccggtc gccggcgcca tcgaggaggc cctggccccg ttcggcgccc    1260
gcccgcactg gggcaaggtg ttctccaccg ccccgaggt cctgcgcacc ctgtacccgc     1320
gctacgccga cttcgaggag ctggtcggcc gccacgaccc cgagggcacc ttccgcaacg    1380
ccttcctcga ccgctacttc cgccgctgag gatcc                               1415
```

<210> SEQ ID NO 18
<211> LENGTH: 52
<212> TYPE: DNA
<213> ORGANISM: Artificial
<220> FEATURE:
<223> OTHER INFORMATION: synthetic oligonucleotide

<400> SEQUENCE: 18

```
gcgctagccg gcccccccggc acaggccatg accccggccg agaagaactg gg           52
```

<210> SEQ ID NO 19
<211> LENGTH: 17
<212> TYPE: DNA
<213> ORGANISM: Artificial
<220> FEATURE:
<223> OTHER INFORMATION: synthetic oligonucleotide

<400> SEQUENCE: 19

```
caggaaacag ctatgac                                                   17
```

<210> SEQ ID NO 20
<211> LENGTH: 1370
<212> TYPE: DNA
<213> ORGANISM: Artificial
<220> FEATURE:
<223> OTHER INFORMATION: synthetic sequence

<400> SEQUENCE: 20

```
gcgctagccg gcccccccggc acaggccatg accccggccg agaagaactg ggccggcaac   60
atcaccttcg cgccaagcg cctgtgcgtc ccgcgctccg tccgcgagct gcgcgagacc     120
gtggccgcct ccggcgccgt gcgcccgctg ggcacccgcc actcgttcaa caccgtcgcc    180
gacacctccg cgcaccacgt gtcgctggcc ggcctgccgc gcgtcgtcga catcgacgtc    240
ccgggccggg ccgtgtccct gtccgccggc ctgcgcttcg gcgagttcgc cgccgagctg    300
cacgcccgcg gcctggccct ggccaacctg ggctccctgc cgcacatctc cgtggcgggc    360
gcggtcgcca ccggcaccca cggctccggc gtcggcaacc gctccctggc gggcgccgtc    420
cgcgccctgt ccctggtcac cgccgacggc gagacccgca ccctgcgccg caccgacgag    480
gacttcgccg gcgccgtcgt gtccctgggc gccctgggcg tcgtcacctc cctggagctg    540
gacctggtcc cggccttcga ggtccgccag tgggtctacg aggacctgcc cgaggccacc    600
ctggccgccc gcttcgacga ggtcatgtcc gccgcctact ccgtgtccgt gttcaccgac    660
tggcgcccgg gccggtcgg ccaggtctgg ctgaagcagc gcgtcggcga cgagggcgcc    720
cgctccgtca tgccggccga gtggctgggc gcccgcctgg ccgacggccc cgccacccg     780 gtccccggca tgcccgccgg caactgcacc gcccagcagg gcgtcccggg cccgtggcac    840
gagcgcctgc cgcacttccg catggagttc acccgtcca acggcgacga gctgcagtcc    900
gagtacttcg tcgcccgcgc ggacgccgtc cggcctacg aggcgctggc ccgcctgcgc    960
gaccgcatcg ccccggtcct gcaggtctcc gagctgcgca ccgtcgcgc cgacgacctg    1020 tggctgtccc cggccacgg ccgcgactcc gtcgccttcc acttcacctg ggtcccggac    1080
gccgccgccg tcgccccggt cgccggcgcc atcgaggagg ccctggcccc gttcggcgcc    1140
```
cgcccgcact ggggcaaggt gttctccacc gcccccgagg tcctgcgcac cctgtacccg   1200
cgctacgccg acttcgagga gctggtcggc cgccacgacc ccgagggcac cttccgcaac   1260
gccttcctcg accgctactt ccgccgctga ggatccgagc tccagctttt gttccctta   1320 gtgagggtta attgcgcgct tggcgtaatc atggtcatag ctgtttcctg   1370

<210> SEQ ID NO 21
<211> LENGTH: 27
<212> TYPE: DNA
<213> ORGANISM: Artificial
<220> FEATURE:
<223> OTHER INFORMATION: synthetic primer

<400> SEQUENCE: 21
gcccatatga gcgacatcac ggtcacc                                        27

<210> SEQ ID NO 22
<211> LENGTH: 24
<212> TYPE: DNA
<213> ORGANISM: Artificial
<220> FEATURE:
<223> OTHER INFORMATION: synthetic primer

<400> SEQUENCE: 22
ggatcctcag cccgcgagca cccc                                           24

<210> SEQ ID NO 23
<211> LENGTH: 24
<212> TYPE: DNA
<213> ORGANISM: Artificial
<220> FEATURE:
<223> OTHER INFORMATION: synthetic primer

<400> SEQUENCE: 23
ctccagacgc gccgggtagg tttc                                           24

<210> SEQ ID NO 24
<211> LENGTH: 22
<212> TYPE: DNA
<213> ORGANISM: Artificial
<220> FEATURE:
<223> OTHER INFORMATION: synthetic primer

<400> SEQUENCE: 24
ctgctgcgcc gaccactgac cc                                             22

<210> SEQ ID NO 25
<211> LENGTH: 27
<212> TYPE: DNA
<213> ORGANISM: Artificial
<220> FEATURE:
<223> OTHER INFORMATION: synthetic primer

<400> SEQUENCE: 25
gccatgggcg acatcacggt caccaac                                        27

<210> SEQ ID NO 26
<211> LENGTH: 26
<212> TYPE: DNA
<213> ORGANISM: Artificial
<220> FEATURE:
<223> OTHER INFORMATION: synthetic primer

<400> SEQUENCE: 26

```
atggatcctc agcccgcgag cacccc                                                  26
```

<210> SEQ ID NO 27
<211> LENGTH: 46
<212> TYPE: PRT
<213> ORGANISM: Sterptomyces coelicolor

<400> SEQUENCE: 27

Met Gly Phe Gly Ser Ala Pro Ile Ala Leu Cys Pro Leu Arg Thr Arg
1               5                   10                  15

Arg Asn Ala Leu Lys Arg Leu Leu Ala Leu Leu Ala Thr Gly Val Ser
            20                  25                  30

Ile Val Gly Leu Thr Ala Leu Ala Gly Pro Pro Ala Gln Ala
        35                  40                  45

<210> SEQ ID NO 28
<211> LENGTH: 466
<212> TYPE: PRT
<213> ORGANISM: Artificial
<220> FEATURE:
<223> OTHER INFORMATION: synthetic fusion protein

<400> SEQUENCE: 28

Met Gly Phe Gly Ser Ala Pro Ile Ala Leu Cys Pro Leu Arg Thr Arg
1               5                   10                  15

Arg Asn Ala Leu Lys Arg Leu Leu Ala Leu Leu Ala Thr Gly Val Ser
            20                  25                  30

Ile Val Gly Leu Thr Ala Leu Ala Gly Pro Pro Ala Gln Ala Met Thr
        35                  40                  45

Pro Ala Glu Lys Asn Trp Ala Gly Asn Ile Thr Phe Gly Ala Lys Arg
    50                  55                  60

Leu Cys Val Pro Arg Ser Val Arg Glu Leu Glu Thr Val Ala Ala
65                  70                  75                  80

Ser Gly Ala Val Arg Pro Leu Gly Thr Arg His Ser Phe Asn Thr Val
                85                  90                  95

Ala Asp Thr Ser Gly Asp His Val Ser Leu Ala Gly Leu Pro Arg Val
            100                 105                 110

Val Asp Ile Asp Val Pro Gly Arg Ala Val Ser Leu Ser Ala Gly Leu
        115                 120                 125

Arg Phe Gly Glu Phe Ala Ala Glu Leu His Ala Arg Gly Leu Ala Leu
    130                 135                 140

Ala Asn Leu Gly Ser Leu Pro His Ile Ser Val Ala Gly Ala Val Ala
145                 150                 155                 160

Thr Gly Thr His Gly Ser Gly Val Gly Asn Arg Ser Leu Ala Gly Ala
                165                 170                 175

Val Arg Ala Leu Ser Leu Val Thr Ala Asp Gly Glu Thr Arg Thr Leu
            180                 185                 190

Arg Arg Thr Asp Glu Asp Phe Ala Gly Ala Val Ser Leu Gly Ala
    195                 200                 205

Leu Gly Val Val Thr Ser Leu Glu Leu Asp Leu Val Pro Ala Phe Glu
    210                 215                 220

Val Arg Gln Trp Val Tyr Glu Asp Leu Pro Glu Ala Thr Leu Ala Ala
225                 230                 235                 240

Arg Phe Asp Glu Val Met Ser Ala Ala Tyr Ser Val Ser Val Phe Thr
                245                 250                 255

Asp Trp Arg Pro Gly Pro Val Gly Gln Val Trp Leu Lys Gln Arg Val
            260                 265                 270

Gly Asp Glu Gly Ala Arg Ser Val Met Pro Ala Glu Trp Leu Gly Ala
            275                 280                 285

Arg Leu Ala Asp Gly Pro Arg His Pro Val Pro Gly Met Pro Ala Gly
        290                 295                 300

Asn Cys Thr Ala Gln Gln Gly Val Pro Gly Pro Trp His Glu Arg Leu
305                 310                 315                 320

Pro His Phe Arg Met Glu Phe Thr Pro Ser Asn Gly Asp Glu Leu Gln
                325                 330                 335

Ser Glu Tyr Phe Val Ala Arg Ala Asp Ala Val Ala Ala Tyr Glu Ala
            340                 345                 350

Leu Ala Arg Leu Arg Asp Arg Ile Ala Pro Val Leu Gln Val Ser Glu
        355                 360                 365

Leu Arg Thr Val Ala Ala Asp Asp Leu Trp Leu Ser Pro Ala His Gly
    370                 375                 380

Arg Asp Ser Val Ala Phe His Phe Thr Trp Val Pro Asp Ala Ala Ala
385                 390                 395                 400

Val Ala Pro Val Ala Gly Ala Ile Glu Glu Ala Leu Ala Pro Phe Gly
                405                 410                 415

Ala Arg Pro His Trp Gly Lys Val Phe Ser Thr Ala Pro Glu Val Leu
            420                 425                 430

Arg Thr Leu Tyr Pro Arg Tyr Ala Asp Phe Glu Glu Leu Val Gly Arg
        435                 440                 445

His Asp Pro Glu Gly Thr Phe Arg Asn Ala Phe Leu Asp Arg Tyr Phe
    450                 455                 460

Arg Arg
465

<210> SEQ ID NO 29
<211> LENGTH: 9495
<212> TYPE: DNA
<213> ORGANISM: Artificial
<220> FEATURE:
<223> OTHER INFORMATION: synthetic expression plasmid

<400> SEQUENCE: 29
ctagagatcg aacttcatgt tcgagttctt gttcacgtag aagccggaga tgtgagaggt      60
gatctggaac tgctcaccct cgttggtggt gacctggagg taaagcaagt gacccttctg     120
gcggaggtgg taaggaacgg ggttccacgg ggagagagag atggccttga cggtcttggg     180
aaggggagct tcggcgcggg ggaggatggt cttgagagag ggggagctag taatgtcgta     240
cttggacagg gagtgctcct tctccgacgc atcagccacc tcagcggaga tggcatcgtg     300
cagagacaga ccccggagg taaccatggg caccgaggtg tcccgccgga aactcatgaa      360
aggcgccgcg gtgtccggcg gcgcgctggc gctgcccgcg ctcggcgcac cgccggcgac     420
ggccgcgccc gccgcaggcc ccgaggacct cccggccccc gcagcggcga tgaccccggc     480
cgagaagaac tgggccggca acatcacctt cggcgccaag cgcctgtgcg tcccgcgctc     540
cgtccgcgag ctgcgcgaga ccgtggccgc ctccggcgcc gtgcgcccgc tgggcacccg     600
ccactcgttc aacaccgtcg ccgacacctc cggcgaccac gtgtcgctgg ccggcctgcc     660
gcgcgtcgtc gacatcgacg tcccgggccg ggccgtgtcc ctgtccgccg gcctgcgctt     720
cggcgagttc gccgccgagc tgcacgcccc cggcctggcc ctggccaacc tgggctccct     780
gccgcacatc tccgtggcgg gcgcggtcgc caccggcacc cacggctccg cgtcggcaa      840 ccgctccctg gcgggcgccg tccgcgccct gtccctggtc accgccgacg gcgagacccg     900

```
caccctgcgc cgcaccgacg aggacttcgc cggcgccgtc gtgtccctgg gcgccctggg      960
cgtcgtcacc tccctggagc tggacctggt cccggccttc gaggtccgcc agtgggtcta     1020
cgaggacctg cccgaggcca ccctggccgc ccgcttcgac gaggtcatgt ccgccgccta     1080
ctccgtgtcc gtgttcaccg actggcgccc gggcccggtc ggccaggtct ggctgaagca     1140
gcgcgtcggc gacgagggcg cccgctccgt catgccggcc gagtggctgg gcgcccgcct     1200
ggccgacggc ccgcgccacc cggtccccgg catgcccgcc ggcaactgca ccgcccagca     1260
gggcgtcccg ggcccgtggc acgagcgcct gccgcacttc gcatggagt tcaccccgtc      1320
caacggcgac gagctgcagt ccgagtactt cgtcgcccgc gcggacgccg tcgcggccta     1380
cgaggcgctg gccgcctgc gcgaccgcat cgccccggtc ctgcaggtct ccgagctgcg      1440
caccgtcgcc gccgacgacc tgtggctgtc cccggcccac ggccgcgact ccgtcgcctt     1500
ccacttcacc tgggtcccgg acgccgccgc cgtcgccccg gtcgccggcg ccatcgagga     1560
ggccctggcc ccgttcggcg cccgcccgca ctggggcaag gtgttctcca ccgcccccga     1620
ggtcctgcgc accctgtacc cgcgctacgc cgacttcgag gagctggtcg gccgccacga     1680
ccccgagggc accttccgca acgccttcct cgaccgctac ttccgccgct gaggatccgc     1740
gagcggatcg gctgaccgga gcggggagga ggacgggcgg ccggcggaaa agtccgccgg     1800
tccgctgaat cgctccccgg gcacggacgt ggcagtatca gcgccatgtc cggcatatcc     1860
cagccctccg catgcaagct tggcactggc cgtcgtttta aacgtcgtg actgggaaaa      1920
ccctggcgtt acccaactta atcgccttgc agcacatccc cctttcgcca gctggcgtaa     1980
tagcgaagag gcccgcaccg atcgcccttc ccaacagttg cgcagcctga atggcgaatg     2040
gcgcctgatg cggtattttc tccttacgca tctgtgcggt atttcacacc gcatatggtg     2100
cactctcagt acaatctgct ctgatgccgc atagttaagc cagccccgac acccgccaac     2160
acccgctgac gcgccctgac gggcttgtct gctcccggca tccgcttaca gacaagctgt     2220
gaccgtctcc gggagctgca tgtgtcaaga ggttttcacc gtcatcaccg aaacgcgcga     2280
gacgaaaggg cctcgtgata cgcctatttt tataggttaa tgtcatgata taatggttt      2340
cttagacgtc aggtggcact tttcggggaa atgtgcgcgg aacccctatt tgtttatttt     2400
tctaaataca ttcaaatatg tatccgctca tgagacaata accctgataa atgcttcaat     2460
aatattgaaa aaggaagagt atgagtattc aacatttccg tgtcgccctt attccctttt     2520
ttgcggcatt ttgccttcct gttttgctc acccagaaac gctggtgaaa gtaaaagatg      2580
ctgaagatca gttgggtgca cgagtgggtt acatcgaact ggatctcaac agcggtaaga     2640
tccttgagag ttttcgcccc gaagaacgtt ttccaatgat gagcactttt aaagttctgc     2700
tatgtggcgc ggtattatcc cgtattgacg ccgggcaaga gcaactcggt cgccgcatac     2760
actattctca gaatgacttg gttgagtact caccagtcac agaaaagcat cttacggatg     2820
gcatgacagt aagagaatta tgcagtgctg ccataaccat gagtgataac actgcggcca     2880
acttacttct gacaacgatc ggaggaccga aggagctaac cgcttttttg cacaacatgg     2940
gggatcatgt aactcgcctt gatcgttggg aaccggagct gaatgaagcc ataccaaacg     3000
acgagcgtga ccaccacgatg cctgtagcaa tggcaacaac gttgcgcaaa ctattaactg     3060
gcgaactact tactctagct tcccggcaac aattaataga ctggatggag gcggataaag     3120
ttgcaggacc acttctgcgc tcggcccttc cggctggctg gtttattgct gataaatctg     3180
gagccggtga gcgtgggtct cgcggtatca ttgcagcact ggggccagat ggtaagccct     3240
```

```
cccgtatcgt agttatctac acgacgggga gtcaggcaac tatggatgaa cgaaatagac    3300
agatcgctga gataggtgcc tcactgatta agcattggta actgtcagac caagtttact    3360
catatatact ttagattgat ttaaaacttc atttttaatt taaaaggatc taggtgaaga    3420
tcctttttga taatctcatg accaaaatcc cttaacgtga gttttcgttc cactgagcgt    3480
cagaccccgt agaaaagatc aaaggatctt cttgagatcc ttttttttctg cgcgtaatct    3540
gctgcttgca acaaaaaaa ccaccgctac cagcggtggt ttgtttgccg gatcaagagc    3600
taccaactct ttttccgaag gtaactggct tcagcagagc gcagatacca atactgtcc    3660
ttctagtgta gccgtagtta ggccaccact caagaactc tgtagcaccg cctacatacc    3720
tcgctctgct aatcctgtta ccagtggctg ctgccagtgg cgataagtcg tgtcttaccg    3780
ggttggactc aagacgatag ttaccggata aggcgcagcg tcgggctga acgggggggtt    3840
cgtgcacaca gcccagcttg gagcgaacga cctacaccga actgagatac ctacagcgtg    3900
agctatgaga aagcgccacg cttcccgaag ggagaaaggc ggacaggtat ccggtaagcg    3960
gcagggtcgg aacaggagag cgcacgaggg agcttccagg gggaaacgcc tggtatcttt    4020
atagtcctgt cgggtttcgc cacctctgac ttgagcgtcg attttttgtga tgctcgtcag    4080
ggggggcggag cctatggaaa aacgccagca acgcggcctt tttacggttc ctggccttt    4140
gctggccttt tgctcacatg ttctttcctg cgttatcccc tgattctgtg ataaccgta    4200
ttaccgcctt tgagtgagct gataccgctc gccgcagccg aacgaccgag cgcagcgagt    4260
cagtgagcga ggaagcggaa gagcgcccaa tacgcaaacc gcctctcccc gcgcgttggc    4320
cgattcatta atgcagctgg cacgacaggt ttcccgactg gaaagcgggc agtgagcgca    4380
acgcaattaa tgtgagttag ctcactcatt aggcacccca ggctttacac tttatgcttc    4440
cggctcgtat gttgtgtgga attgtgagcg gataacaatt tcacacagga aacagctatg    4500
accatgatta cgccgaattc ggggcatgcc tgcaggagtg gggaggcacg atggccgctt    4560
tggtcgacct caacgagacg atgaagccgt ggaacgacac caccccggcg ccctgctgg    4620
accacacccg gcactacacc ttcgacgtct gatcatcact gacgaatcga ggtcgaggaa    4680
ccgagcgtcc gaggaacaca ggcgcttatc ggttggccgc gagattcctg tcgatcctct    4740
cgtgcagcgc gattccgagg gaaacggaaa cgttgagaga ctcggtctgg ctcatcatgg    4800
ggatggaaac cgaggcggaa gacgcctcct cgaacaggtc ggaaggccca cccttttcgc    4860
tgccgaacag caaggccagc cgatccggat tgtccccgag ttccttcacg gaaatgtcgc    4920
catccgcctt gagcgtcatc agctgcatac cgctgtcccg aatgaaggcg atggcctcct    4980
cgcgaccgga gagaacgacg ggaagggaga agacgtaacc tcggctggcc ctttggagac    5040
gccggtccgc gatgctggtg atgtcactgt cgaccaggat gatccccgac gctccgagcg    5100
cgagcgacgt gcgtactatc gcgccgatgt tcccgacgat cttcaccccg tcgagaacga    5160
cgacgtcccc acgccggctc gcgatatcgc cgaacctggc cggcgagggg acgcgggcga    5220
tgccgaatgt cttggccttc cgctccccct gaacaactg gttgacgatc gaggagtcga    5280
tgaggcggac cggtatgttc tgccgcccgc acagatccag caactcagat ggaaaaggac    5340
tgctgtcgct gccgtagacc tcgatgaact ccaccccggc cgcgatgctg tgcatgaggg    5400
gctcgacgtc ctcgatcaac gttgtcttta tgttggatcg cgacggcttg gtgacatcga    5460
tgatccgctg caccgcggga tcggacggat ttgcgatggt gtccaactca gtcatggtcg    5520
tcctaccggc tgctgtgttc agtgacgcga ttcctggggt gtgacaccct acgcgacgat    5580
ggcggatggc tgccctgacc ggcaatcacc aacgcaaggg gaagtcgtcg ctctctggca    5640
```

```
aagctccccg ctcttcccctcg tccgggaccc gcgcggtcga tccccgcata tgaagtattc    5700
gccttgatca gtcccggtgg acgcgccagc ggcccgccgg agcgacggac tcccccgacct   5760
cgatcgtgtc gccctgagcg tccacgtaga cgttgcgtga gagcaggact gggccgccgc    5820
cgaccgcacc gccctcacca ccgaccgcga ccgcgccatg gccgccgccg acggcctggt    5880
cgccgccgcc gcccgccggt tcggcgcctg acccgaccaa ccccgcgggg cgccggcac     5940
ttcgtgctgg cgccccgccc ccacccacca ggagaccgac catgaccgac ttcgacggac    6000
gcctgaccga ggggaccgtg aacctggtcc aggaccccaa cggcggtggc tggtccgccc    6060
actgcgctga gccggttgc gactgggccg acttcgccgg accgctcggc ttccagggcc     6120
tcgtggccat cgctcgccga cacacgcact gaccgcacgt caaagcccccg ccggatacccc   6180
ggcgggctc tcttcggccc tccaagtcac accagcccca aggggcgtcg ggagtggcgg     6240
agggaacctc tggcccgatt ggtgccagga ttcccaccag accaaagagc aacgggccgg    6300
acttcgcacc tccgacccgt ccgctcccag actcgcgccc cttagccggg cgagacagga    6360
acgttgctcg tgcccagagt acggagcgat gccgaggcat tgccagatcg gcccgccggg   6420
ccccgctgcc actgcgggac cgcaattgcc cacacaccgg gcaaacgcc gcgtatctac     6480
tgctcagacc gctgccggat ggcagcgaag cgggcgatcg cgcgtgtgac gcgagatgcc    6540
gcccgaggca aaagcgaaca ccttgggaaa gaaacaacag agtttcccgc acccctccga    6600
cctgcggttt ctccggacgg ggtggatggg gagagcccga gaggcgacag cctctgggaa    6660
gtaggaagca cgtcgcggac cgaggctgcc cgactgcgga aagccgcccg gtacagccgc    6720
cgccggacgc tgtggcggat cagcggggac gccgcgtgca agggctgcgg ccgcgccctg    6780
atggaccctg cctccggcgt gatcgtcgcc cagacggcgg ccggaacgtc cgtggtcctg    6840
ggcctgatgc ggtgcgggcg gatctggctc tgcccggtct gcgccgccac gatccggcac    6900
aagcgggccg aggagatcac cgccgccgtg gtcgagtgga tcaagcgcgg ggggaccgcc    6960
tacctggtca ccttcacggc ccgccatggg cacacggacc ggctcgcgga cctcatggac    7020
gccctccagg gcacccggaa gacgccggac agccccccggc ggccgggcgc ctaccagcga    7080
ctgatcacgg gcggcacgtg ggccggacgc cgggccaagg acgggcaccg ggccgccgac    7140
cgcgagggca tccgagaccg gatcgggtac gtcggcatga tccgcgcgac cgaagtcacc    7200
gtggggcaga tcaacggctg gcacccgcac atccacgcga tcgtcctggt cggcggccgg    7260
accgaggggg agcggtccgc gaagcagatc gtcgccacct tcgagccgac cggcgccgcg    7320
ctcgacgagt ggcaggggca ctggcggtcc gtgtggaccg ccgccctgcg caaggtcaac    7380
cccgccttca cgcccgacga ccggcacggc gtcgacttca gcggctgga gaccgagcgc     7440
gacgccaacg acctcgccga gtacatcgcc aagacccagg acgggaaggc gcccgccctc    7500
gaactcgccc gcgccgacct caagacggcg accggcggga acgtcgcccc gttcgaactc    7560
ctcggacgga tcgggaccct gaccggcggc atgaccgagg acgacgccgc cggggtcggc    7620
tcgctggagt ggaacctctc gcgctggcac gagtacgagc gggcaacccg gggacgccgg    7680
gccatcgaat ggacccgcta cctgcggcag atgctcgggc tcgacggcgg cgacaccgag    7740
gccgacgacc tcgatctgct cctggcgcc gacgccgacg gcggggagct gcgggccggg    7800
gtcgccgtga ccgaggacgg atggcacgcg gtcacccgcc gcgccctcga cctcgaggcg    7860
acccgggccg ccgaaggcaa ggacggcaac gaggattcgg cggccgtggg cgaacgggtg    7920
cgggaggtcc tggcgctggc cgacgcgcgcc gacacagtgg tggtgctcac ggcggggag    7980
```

```
gtggccgagg cgtacgccga catgctcgcc gccctcgccc agcgccgcga ggaagcaact    8040
gcacgccgac ggcgagagca ggacgacgac caggacgacg acgccgacga ccgccaggag    8100
cgggccgccc ggcacatcgc ccggctcgca agtgggccca cttcgcacta actcgctccc    8160
ccccgccgta cgtcatcccg gtgacgtacg gcggggtcg gtgacgtacg cggcgacggc    8220
ggccggggtc gaagccgcgg gagtaatcct gggattactc gcccgggtc ggccccgccg    8280
gcacttcgtg caggcggtac ctcgcgcccg actcgcctcg ctacgagacg tgccgcgtac    8340
ggtcgtcggc catgagcacc accccccca gggacgccga cggcgcgaag ctctgcgcct    8400
ggtgcggctc ggagatcaag caatccgcg tcggccggag ccgggactac tgccgccgct    8460
cctgccgcca gcgggcgtac gaggcccggc gccagcgcga ggcgatcgtg tccgccgtgg    8520
cgtcggcagt cgctcgccga gatacgtcac gtgacgaaat gcagcagcct tccattccgt    8580
cacgtgacga aactcgggcc gcaggtcaga gcacggttcc gcccgctccg gccctgccgg    8640
accccccggct gcagctcgcc cggccgccgg tccccctgcc gtccggcccg tcccagaggc    8700
agcgtcggcg gctcctgcct ccccgcccg gcgccgaccg ggaccgcaa acccctttgat    8760
ccgctgtcgg gggtgatcac tacggtgggt gccgaagtga tcacggggag gactgatgca    8820
ccaccaggac cgggaccagg accaggcgtt agcggcagtg ctggccgcac tgctcctggt    8880
cggcgggacg ctgatcgtgc gggagctcct gggcctgtgg cccgccgtgg cggtcggcat    8940
ggcgcccgcc ctcgccctct acggaggccc gcccgcggcc cgccggatag ccgtcgcggt    9000
cgaggtccgc cggttccgcc ggcatcttgc ccaccacgat cgggcagccg gatgaccggc    9060
cacgacggag ccgcacggct gaccagctcg acggccgcca cctcatcgcg gcagcaggtg    9120
ctccccagca acccacgacg gggctcaggg tcgcctcacg cggctcagca ccgcgacggc    9180
gggggtacgg cgctccggga ggctgacagg cgctcagacg gccgcgtagg gccgcgagtc    9240
ccccacccct ccccgctgcc ctgtcggcga gcacaacggc gatgcccgca gtcggcggag    9300
caggcgccac gtaaaccgcc caccgatgcc gccccgtcg tgtgcgcggg ccggtcggcg    9360
gccgggccgg agcggggcga agacaggagc gtcggccggg ccgtgggccg ggccgcgcgg    9420
cccgctcgcg ggccgccttg atgacgtagg gaaagttgta ccgcaaaaaa cgcagcctga    9480
actagttgcg atcct                                                     9495
```

<210> SEQ ID NO 30
<211> LENGTH: 9488
<212> TYPE: DNA
<213> ORGANISM: Artificial
<220> FEATURE:
<223> OTHER INFORMATION: synthetic expression plasmid

<400> SEQUENCE: 30

```
ctagagatcg aacttcatgt tcgagttctt gttcacgtag aagccggaga tgtgagaggt      60
gatctggaac tgctcaccct cgttggtggt gacctggagg taaagcaagt gacccttctg     120
gcggaggtgg taaggaacgg ggttccacg ggagagagag atggccttga cggtcttggg     180
aaggggagct tcggcgcggg ggaggatggt cttgagagag ggggagctag taatgtcgta     240
cttggacagg gagtgctcct tctccgacgc atcagccacc tcagcggaga tggcatcgtg     300
cagagacaga ccccggagg taaccatggg ctttgggagc gctcccatcg cgttgtgtcc     360
gcttcgcacg aggaggaacg cttttgaaacg ccttttggcc ctgctcgcga ccggcgtgtc    420
gatcgtcggc ctgactgcgc tagccggccc cccggcacag gccatgaccc cggccgagaa    480
gaactgggcc ggcaacatca ccttcggcgc caagcgcctg tgcgtcccgc gctccgtccg    540
```

```
cgagctgcgc gagaccgtgg ccgcctccgg cgccgtgcgc ccgctgggca cccgccactc    600
gttcaacacc gtcgccgaca cctccggcga ccacgtgtcg ctggccggcc tgccgcgcgt    660
cgtcgacatc gacgtcccgg ccgggccgt gtccctgtcc gccggcctgc gcttcggcga    720
gttcgccgcc gagctgcacg cccgcggcct ggccctgccc aacctgggct ccctgccgca    780
catctccgtg gcgggcgcgg tcgccaccgg cacccacggc tccggcgtcg gcaaccgctc    840
cctggcgggc gccgtccgcg ccctgtccct ggtcaccgcc gacggcgaga cccgcaccct    900
gcgccgcacc gacgaggact cgccggcgc cgtcgtgtcc ctgggcgccc tgggcgtcgt    960
cacctccctg gagctggacc tggtcccggc cttcgaggtc cgccagtggg tctacgagga   1020
cctgcccgag gccaccctgg ccgcccgctt cgacgaggtc atgtccgccg cctactccgt   1080
gtccgtgttc accgactggc gcccgggccc ggtcggccag gtctggctga agcagcgcgt   1140
cggcgacgag ggcgcccgct ccgtcatgcc ggccgagtgg ctgggcgccc gcctggccga   1200
cggcccgcgc cacccggtcc ccggcatgcc cgccggcaac tgcaccgccc agcagggcgt   1260
cccgggcccg tggcacgagc gcctgccgca cttccgcatg gagttcaccc cgtccaacgg   1320
cgacgagctg cagtccgagt acttcgtcgc ccgcgcggac gccgtcgcgg cctacgaggc   1380
gctggcccgc ctgcgcgacc gcatcgcccc ggtcctgcag gtctccgagc tgccgcaccgt   1440
cgccgccgac gacctgtggc tgtccccggc ccacggccgc gactccgtcg ccttccactt   1500
cacctgggtc ccggacgccg ccgccgtcgc cccggtcgcc ggcgccatcg aggaggccct   1560
ggccccgttc ggcgccccgcc cgcactgggg caaggtgttc tccaccgccc ccgaggtcct   1620
gcgcaccctg tacccgcgct acgccgactt cgaggagctg gtcggccgcc acgacccgga   1680
gggcaccttc cgcaacgcct tcctcgaccg ctacttccgc cgctgaggat ccgcgagcgg   1740
atcggctgac cggagcgggg aggaggacgg gcggccggcg gaaaagtccg ccggtccgct   1800
gaatcgctcc ccgggcacgg acgtggcagt atcagcgcca tgtccggcat atcccagccc   1860
tccgcatgca agcttggcac tggccgtcgt tttacaacgt cgtgactggg aaaaccctgg   1920
cgttacccaa cttaatcgcc ttgcagcaca tccccctttc gccagctggc gtaatagcga   1980
agaggcccgc accgatcgcc cttcccaaca gttgcgcagc ctgaatggcg aatggcgcct   2040
gatgcggtat tttctcctta cgcatctgtg cggtatttca caccgcatat ggtgcactct   2100
cagtacaatc tgctctgatg ccgcatagtt aagccagccc cgacacccgc caacacccgc   2160
tgacgcgccc tgacgggctt gtctgctccc ggcatccgct tacagacaag ctgtgaccgt   2220
ctccgggagc tgcatgtgtc aagaggtttt caccgtcatc accgaaacgc gcgagacgaa   2280
agggcctcgt gatacgccta ttttatagg ttaatgtcat gataataatg gtttcttaga    2340
cgtcaggtgg cacttttcgg ggaaatgtgc gcggaacccc tatttgttta ttttctaaa   2400
tacattcaaa tatgtatccg ctcatgagac aataaccctg ataaatgctt caataatatt   2460
gaaaaaggaa gagtatgagt attcaacatt tccgtgtcgc ccttattccc ttttttgcgg   2520
cattttgcct tcctgttttt gctcacccag aaacgctggt gaaagtaaaa gatgctgaag   2580
atcagttggg tgcacgagtg ggttacatcg aactggatct caacagcggt aagatccttg   2640
agagttttcg ccccgaagaa cgttttccaa tgatgagcac ttttaaagtt ctgctatgtg   2700
gcgcggtatt atcccgtatt gacgccgggc aagagcaact cggtcgccgc atacactatt   2760
ctcagaatga cttggttgag tactcaccag tcacagaaaa gcatcttacg gatggcatga   2820
cagtaagaga attatgcagt gctgccataa ccatgagtga taacactgcg ccaacttact   2880
```

```
tctgacaacg atcggaggac cgaaggagct aaccgctttt ttgcacaaca tgggggatca   2940
tgtaactcgc cttgatcgtt gggaaccgga gctgaatgaa gccataccaa acgacgagcg   3000
tgacaccacg atgcctgtag caatggcaac aacgttgcgc aaactattaa ctggcgaact   3060
acttactcta gcttcccggc aacaattaat agactggatg gaggcggata agttgcagg    3120
accacttctg cgctcggccc ttccggctgg ctggtttatt gctgataaat ctggagccgg   3180
tgagcgtggg tctcgcggta tcattgcagc actggggcca gatggtaagc cctcccgtat   3240
cgtagttatc tacacgacgg ggagtcaggc aactatggat gaacgaaata gacagatcgc   3300
tgagataggt gcctcactga ttaagcattg gtaactgtca gaccaagttt actcatatat   3360
actttagatt gatttaaaac ttcattttta atttaaaagg atctaggtga agatcctttt   3420
tgataatctc atgaccaaaa tcccttaacg tgagttttcg ttccactgag cgtcagaccc   3480
cgtagaaaag atcaaaggat cttcttgaga tcctttttt ctgcgcgtaa tctgctgctt    3540
gcaaacaaaa aaaccaccgc taccagcggt ggtttgtttg ccggatcaag agctaccaac   3600
tcttttccg aaggtaactg gcttcagcag agcgcagata ccaaatactg tccttctagt    3660
gtagccgtag ttaggccacc acttcaagaa ctctgtagca ccgcctacat acctcgctct   3720
gctaatcctg ttaccagtgg ctgctgccag tggcgataag tcgtgtctta ccgggttgga   3780
ctcaagacga tagttaccgg ataaggcgca gcggtcgggc tgaacggggg gttcgtgcac   3840
acagcccagc ttggagcgaa cgacctacac cgaactgaga tacctacagc gtgagctatg   3900
agaaagcgcc acgcttcccg aagggagaaa ggcggacagg tatccggtaa gcggcagggt   3960
cggaacagga gagcgcacga gggagcttcc agggggaaac gcctggtatc tttatagtcc   4020
tgtcgggttt cgccacctct gacttgagcg tcgatttttg tgatgctcgt caggggggcg   4080
gagcctatgg aaaaacgcca gcaacgcggc ctttttacgg ttcctggcct tttgctggcc   4140
ttttgctcac atgttctttc ctgcgttatc ccctgattct gtggataacc gtattaccgc   4200
ctttgagtga gctgataccg ctcgccgcag ccgaacgacc gagcgcagcg agtcagtgag   4260
cgaggaagcg gaagagcgcc caatacgcaa accgcctctc cccgcgcgtt ggccgattca   4320
ttaatgcagc tggcacgaca ggtttcccga ctggaaagcg ggcagtgagc gcaacgcaat   4380
taatgtgagt tagctcactc attaggcacc ccaggcttta cactttatgc ttccggctcg   4440
tatgttgtgt ggaattgtga gcggataaca atttcacaca ggaaacagct atgaccatga   4500
ttacgccgaa ttcggggcat gcctgcagga gtggggaggc acgatggccg ctttggtcga   4560
cctcaacgag acgatgaagc cgtggaacga caccaccccg gcggccctgc tggaccacac   4620
ccggcactac accttcgacg tctgatcatc actgacgaat cgaggtcgag gaaccgagcg   4680
tccgaggaac acaggcgctt atcggttggc cgcgagattc ctgtcgatcc tctcgtgcag   4740
cgcgattccg agggaaacgg aaacgttgag agactcggtc tggctcatca tggggatgga   4800
aaccgaggcg gaagacgcct cctcgaacag gtcggaaggc ccaccctttt cgctgccgaa   4860
cagcaaggcc agccgatccg gattgtcccc gagttccttc acggaaatgt cgccatccgc   4920
cttgagcgtc atcagctgca taccgctgtc ccgaatgaag gcgatggcct cctcgcgacc   4980
ggagagaacg acgggaaggg agaagacgta acctcggctg gcccttggga gacgccggtc   5040
cgcgatgctg gtgatgtcac tgtcgaccag gatgatcccc gacgctccga gcgcgagcga   5100
cgtgcgtact atcgcgccga tgttcccgac gatcttcacc ccgtcgagaa cgacgacgtc   5160
cccacgccgc ctcgcgatat cgccgaacct ggccgggcga gggacgcggg cgatgccgaa   5220
tgtcttggcc ttccgctccc ccttgaacaa ctggttgacg atcgaggagt cgatgaggcg   5280
```

```
gaccggtatg ttctgccgcc cgcacagatc cagcaactca gatggaaaag gactgctgtc   5340
gctgccgtag acctcgatga actccacccc ggccgcgatg ctgtgcatga ggggctcgac   5400
gtcctcgatc aacgttgtct ttatgttgga tcgcgacggc ttggtgacat cgatgatccg   5460
ctgcaccgcg ggatcggacg gatttgcgat ggtgtccaac tcagtcatgg tcgtcctacc   5520
ggctgctgtg ttcagtgacg cgattcctgg ggtgtgacac cctacgcgac gatggcggat   5580
ggctgccctg accggcaatc accaacgcaa ggggaagtcg tcgctctctg gcaaagctcc   5640
ccgctcttcc ccgtccggga cccgcgcggt cgatccccgc atatgaagta ttcgccttga   5700
tcagtcccgg tggacgcgcc agcggcccgc cggagcgacg gactcccga cctcgatcgt   5760 gtcgccctga gcgtccacgt agacgttgcg tgagagcagg actgggccgc cgccgaccgc   5820
accgccctca ccaccgaccg cgaccgcgcc atggccgccg ccgacggcct ggtcgccgcc   5880
gccgcccgcc ggttcggcgc ctgacccgac caaccccgc ggggcgccgg cacttcgtgc   5940
tggcgccccg cccccaccca ccaggagacc gaccatgacc gacttcgacg gacgcctgac   6000 cgagggggacc gtgaacctgg tccaggaccc caacggcggt ggctggtccg cccactgcgc   6060
tgagcccggt tgcgactggg ccgacttcgc cggaccgctc ggcttccagg gcctcgtggc   6120
catcgctcgc cgacacacgc actgaccgca cgtcaaagcc ccgccggata cccggcgggg   6180
ctctcttcgg ccctccaagt cacaccagcc ccaaggggcg tcgggagtgg cggagggaac   6240
ctctggcccg attggtgcca ggattcccac cagaccaaag agcaacgggc cggacttcgc   6300
acctccgacc cgtccgctcc cagactcgcg ccccttagcc gggcgagaca ggaacgttgc   6360
tcgtgcccag agtacggagc gatgccgagg cattgccaga tcggcccgcc gggccccgct   6420
gccactgcgg gaccgcaatt gcccacacac cgggcaaacg gccgcgtatc tactgctcag   6480
accgctgccg gatggcagcg aagcgggcga tcgcgcgtgt gacgcgagat gccgcccgag   6540
gcaaaagcga acaccttggg aaagaaacaa cagagtttcc cgcacccctc cgacctgcgg   6600
tttctccgga cggggtggat ggggagagcc cgagaggcga cagcctctgg gaagtaggaa   6660
gcacgtcgcg gaccgaggct gcccgactgc ggaaagccgc ccggtacagc cgccgccgga   6720
cgctgtggcg gatcagcggg gacgccgcgt gcaagggctg cggccgcgcc ctgatggacc   6780
ctgcctccgg cgtgatcgtc gcccagacgg cggccggaac gtccgtggtc ctgggcctga   6840
tgcggtgcgg gcggatctgg ctctgcccgg tctgcgccgc cacgatccgg cacaagcggg   6900
ccgaggagat caccgccgcc gtggtcgagt ggatcaagcg cggggggacc gcctacctgg   6960
tcaccttcac ggcccgccat gggcacacgg accggctcgc ggacctcatg gacgccctcc   7020
agggcacccg gaagacgccg gacagccccc ggcggccggg cgcctaccag cgactgatca   7080
cgggcggcac gtgggccgga cgccgggcca aggacgggca ccgggccgcc gaccgcgagg   7140
gcatccgaga ccggatcggg tacgtcggca tgatccgcgc gaccgaagtc accgtggggc   7200
agatcaacgg ctggcacccg cacatccacg cgatcgtcct ggtcggcggc cggaccgagg   7260
gggagcggtc cgcgaagcag atcgtcgcca ccttcgagcc gaccggcgcc gcgctcgacg   7320
agtggcaggg gcactggcgg tccgtgtgga ccgccgccct gcgcaaggtc aaccccgcct   7380
tcacgcccga cgaccggcac ggcgtcgact tcaagcggct ggagaccgag cgcgacgcca   7440
acgacctcgc cgagtacatc gccaagaccc aggacgggaa ggcgcccgcc ctcgaactcg   7500
cccgcgccga cctcaagacg gcgaccggcg ggaacgtcgc cccgttcgaa ctcctcggac   7560
ggatcgggga cctgaccggc ggcatgaccg aggacgacgc cgccggggtc ggctcgctgg   7620
```

```
agtggaacct ctcgcgctgg cacgagtacg agcgggcaac ccggggacgc cgggccatcg    7680
aatggacccg ctacctgcgg cagatgctcg ggctcgacgg cggcgacacc gaggccgacg    7740
acctcgatct gctcctggcg gccgacgccg acggcgggga gctgcgggcc ggggtcgccg    7800
tgaccgagga cggatggcac gcggtcaccc gccgcgccct cgacctcgag gcgacccggg    7860
ccgccgaagg caaggacggc aacgaggatt cggcggccgt gggcgaacgg gtgcgggagg    7920
tcctggcgct ggccgacgcg gccgacacag tggtggtgct cacggcgggg gaggtggccg    7980
aggcgtacgc cgacatgctc gccgccctcg cccagcgccg cgaggaagca actgcacgcc    8040
gacggcgaga gcaggacgac gaccaggacg acgacgccga cgaccgccag gagcgggccg    8100
cccggcacat cgcccggctc gcaagtgggc ccacttcgca ctaactcgct ccccccgcc    8160 gtacgtcatc ccggtgacgt acggcggggg tcggtgacgt acgcggcgac ggcggccggg    8220
gtcgaagccg cggagtaat cctgggatta ctcgcccggg gtcggccccg ccggcacttc    8280
gtgcaggcgg tacctcgcgc ccgactcgcc tcgctacgag acgtgccgcg tacggtcgtc    8340
ggccatgagc accaccaccc ccaggacgc cgacggcgcg aagctctgcg cctggtgcgg    8400
ctcggagatc aagcaatccg gcgtcggccg gagccgggac tactgccgcc gctcctgccg    8460
ccagcgggcg tacgaggccc ggcgccacg cgaggcgatc gtgtccgccg tggcgtcggc    8520
agtcgctcgc cgagatacgt cacgtgacga atgcagcag ccttccattc cgtcacgtga    8580
cgaaactcgg gccgcaggtc agagcacggt tccgcccgct ccggccctgc cggacccccg    8640
gctgcagctc gcccggccgc cggtcccccct gccgtccggc cgtcccaga ggcagcgtcg    8700 gcggctcctg cctcccccgc ccggcgccga ccgggacccg caaacccctt gatccgctgt    8760
cgggggtgat cactacggtg ggtgccgaag tgatcacggg gaggactgat gcaccaccag    8820
gaccgggacc aggaccaggc gttagcggca gtgctggccg cactgctcct ggtcggcggg    8880
acgctgatcg tgcgggagct cctgggcctg tggcccgccg tggcggtcgg catggcgccc    8940
gccctcgccc tctacggagg cccgcccgcg cccgccgga tagccgtcgc ggtcgaggtc    9000
cgccggttcc gccggcatct tgcccaccac gatcgggcag ccggatgacc ggccacgacg    9060
gagccgcacg gctgaccagc tcgacggccg ccacctcatc gcggcagcag gtgctccca    9120 gcaacccacg acggggctca gggtcgcctc acgcggctca gcaccgcgac ggcgggggta    9180
cggcgctccg ggaggctgac aggcgctcag acggccgcgt agggccgcga gtcccccacc    9240
cctccccgct gccctgtcgg cgagcacaac ggcgatgccc gcagtcggcg gagcaggcgc    9300
cacgtaaacc gcccaccgat gccgccccg tcgtgtgcgc gggccggtcg gcggccgggc    9360
cggagcgggg cgaagacagg agcgtcggcc gggccgtggg ccggccgcg cggcccgctc    9420 gcgggccgcc ttgatgacgt agggaaagtt gtaccgcaaa aaacgcagcc tgaactagtt    9480
gcgatcct                                                             9488
```

<210> SEQ ID NO 31
<211> LENGTH: 46
<212> TYPE: PRT
<213> ORGANISM: Streptomyces coelicolor

<400> SEQUENCE: 31

Met Gly Phe Gly Ser Ala Pro Ile Ala Leu Cys Pro Leu Arg Thr Arg
1               5                   10                  15

Arg Asn Ala Leu Lys Arg Leu Leu Ala Leu Leu Ala Thr Gly Val Ser
            20                  25                  30

Ile Val Gly Leu Thr Ala Leu Ala Gly Pro Pro Ala Gln Ala
        35                  40                  45

-continued

```
                35                  40                  45

<210> SEQ ID NO 32
<211> LENGTH: 9
<212> TYPE: PRT
<213> ORGANISM: Streptomyces coelicolor

<400> SEQUENCE: 32

Ala Leu Ala Gly Pro Pro Ala Gln Ala
1               5

<210> SEQ ID NO 33
<211> LENGTH: 462
<212> TYPE: PRT
<213> ORGANISM: Artificial
<220> FEATURE:
<223> OTHER INFORMATION: synthetic sequence

<400> SEQUENCE: 33

Ala Leu Ala Gly Pro Pro Ala Gln Ala Met Asp Gly Lys Arg Cys
1               5                   10                  15

Arg Asp Gly Thr Pro Gln Pro Pro Ala Pro Ser Glu Gln Val Thr Pro
                20                  25                  30

Ser Ala Ala Ser Leu Arg Ala Ala Tyr Asp Val Glu Val Ser Ala
            35                  40                  45

Pro Arg Leu Arg Asn Trp Ala Gly Asn Ile Ala Phe Arg Pro Arg Arg
50                  55                  60

Tyr Val Gln Pro Arg Asp Leu Asp Glu Leu Val Glu Ile Ile Arg Val
65                  70                  75                  80

Ser Asp Gln Val Arg Val Leu Gly Thr Gly His Ser Phe Asn Pro Ile
                85                  90                  95

Ala Asp Thr Thr Gly Thr Leu Ile Ser Leu Asp His Leu Pro Arg Glu
                100                 105                 110

Val Arg Val Met Pro Gly Arg Thr Ala Val Ser Ala Gly Thr Arg Tyr
            115                 120                 125

Gly Asp Leu Ala Phe Pro Leu His Glu Ala Gly Trp Ala Leu Ala Asn
130                 135                 140

Val Gly Ser Leu Pro His Ile Ser Ile Ala Gly Ala Cys Ala Thr Ala
145                 150                 155                 160

Thr His Gly Ser Gly Asp Arg Asn Gly Cys Leu Ala Thr Ala Val Ala
                165                 170                 175

Gly Met Thr Gly Val Asp Gly Thr Cys Arg Val Phe His Leu Thr Ala
            180                 185                 190

Glu Ser Pro Glu Phe Pro Gly Ala Val Val His Leu Gly Ala Leu Gly
        195                 200                 205

Ala Val Thr Glu Ile Glu Leu Val Thr Glu Pro Thr Phe Thr Val Arg
    210                 215                 220

Gln Trp Val Tyr Glu Asp Ala Pro Leu Asp Asn Val Phe Ala Asp Leu
225                 230                 235                 240

Asp Asp Val Thr Ser Ala Ala Tyr Ser Val Ser Ile Phe Thr Thr Trp
                245                 250                 255

Asp Pro Pro Thr Ala Arg Gln Ile Trp Leu Lys Glu Arg Val Ala Ala
            260                 265                 270

Gly Arg Pro Asp Pro Pro Ala Arg Arg Trp Gly Gly Arg Leu Ala Glu
        275                 280                 285

Arg Asp His Asn Pro Val Pro Gly Met Pro Pro Glu Asn Cys Thr Pro
    290                 295                 300
```

Gln Leu Gly Arg Ile Gly Pro Trp His Glu Arg Leu Pro His Phe Arg
305                 310                 315                 320

Leu Asp Val Thr Pro Ser Ala Gly Asp Glu Leu Gln Ser Glu Tyr Phe
            325                 330                 335

Val Pro Arg Ala Ala Val Glu Ala Tyr Arg Ala Leu Arg His Ile
        340                 345                 350

Gly Ser Arg Ile Ala Pro Val Leu Gln Ile Ser Glu Ile Arg Thr Val
        355                 360                 365

Ala Ala Asp Glu Leu Trp Leu Ser Pro Ala Tyr His Arg Pro Ser Val
370                 375                 380

Ala Phe His Phe Thr Trp Ile Ala Asp Glu Glu Ala Val Arg Pro Val
385                 390                 395                 400

Val Ser Glu Val Glu Arg Ala Leu Ala Pro Leu Gln Pro Arg Pro His
            405                 410                 415

Trp Gly Lys Leu Phe Thr Met Asp Pro Ala Val Val Arg Ala Ala Tyr
        420                 425                 430

Pro Arg Phe Asp Asp Phe Val Ala Leu Ala Glu Arg Tyr Asp Pro Glu
        435                 440                 445

Gly Lys Phe Gln Asn Asp Phe Leu Arg Arg Phe Phe Ala Gly
    450                 455                 460

<210> SEQ ID NO 34
<211> LENGTH: 1395
<212> TYPE: DNA
<213> ORGANISM: Artificial
<220> FEATURE:
<223> OTHER INFORMATION: synthetic sequence

<400> SEQUENCE: 34
gcgctagcgg gcccgccggc ccaggccatg gatggcggca agcgctgccg cgacggcacc        60
ccgcagccgc cggccccgtc cgagcaggtc accccgtcgg ccgccgcctc cctgcgggcc       120
gcctacgacg tggaggtctc cgccccgcgc ctgcgcaact gggccggcaa catcgccttc       180
cgcccgcgcc gctacgtcca gccgcgcgac ctcgacgagc tggtcgagat catccgggtc       240
tccgaccagg tccgcgtcct gggcaccggc cactccttca cccccatcgc cgacaccacc       300
ggcaccctga tctccctgga ccacctgccg cgcgaggtcc gcgtcatgcc gggccgcacc       360
gcggtctccg ccggcacccg ctacggcgac ctggccttcc gctgcacga ggccggctgg       420 gccctggcca acgtcggctc cctgccgcac atctccatcg ccggcgcctg cgccacggcc       480
acccacggct ccgcgaccg caacggctgc ctggccaccg ccgtcgccgg catgaccggc       540
gtcgacggca cctgccgcgt gttccacctg accgccgagt cccccgagtt cccgggcgcc       600
gtcgtccacc tgggcgccct gggcgccgtc accgagatcg agctggtcac cgagccgacc       660
ttcaccgtcc gccagtgggt ctacgaggac gccccgctgg acaacgtgtt cgccgacctg       720
gacgacgtca cctccgccgc ctactcggtc tccatcttca ccacctggga cccgccgacc       780
gcccggcaga tctggctgaa ggagcgcgtc gccgccggcc gccggaccc gccggcccgc       840 cgctggggcg gccgcctcgc cgagcgcgac acaaccccg tcccggggat gccgcccgag       900
aactgcaccc ccagctgggg ccgcatcggc cgtggcacg agcgcctgcc gcacttccgc       960
ctggacgtca cccccctccgc gggcgacgag ctgcagtccg agtacttcgt cccgcgcgcc      1020
gccgccgtcg aggcctaccg cgccctgcgc cacatcggct cccgcatcgc ccgtcctg       1080 cagatctccg agatccgcac cgtcgccgcc gacgagctgt ggctgtcccc ggcctaccac      1140

```
cgcccgtccg tcgccttcca cttcacctgg atcgccgacg aggaggccgt ccgcccggtg      1200
gtctccgagg tcgagcgcgc cctggccccg ctgcagccgc gcccgcactg gggcaagctg      1260
ttcacgatgg acccggccgt cgtccgcgcc gcctacccgc gcttcgacga cttcgtcgcc      1320
ctggccgagc gctacgaccc cgagggcaag ttccagaacg acttcctgcg ccgcttcttc      1380
gccggctaag gatcc                                                        1395
```

<210> SEQ ID NO 35
<211> LENGTH: 499
<212> TYPE: PRT
<213> ORGANISM: Artificial
<220> FEATURE:
<223> OTHER INFORMATION: synthetic fusion protein

<400> SEQUENCE: 35

```
Met Gly Phe Gly Ser Ala Pro Ile Ala Leu Cys Pro Leu Arg Thr Arg
1               5                   10                  15

Arg Asn Ala Leu Lys Arg Leu Leu Ala Leu Leu Ala Thr Gly Val Ser
            20                  25                  30

Ile Val Gly Leu Thr Ala Leu Ala Gly Pro Pro Ala Gln Ala Met Asp
        35                  40                  45

Gly Gly Lys Arg Cys Arg Asp Gly Thr Pro Gln Pro Ala Pro Ser
    50                  55                  60

Glu Gln Val Thr Pro Ser Ala Ala Ser Leu Arg Ala Ala Tyr Asp
65                  70                  75                  80

Val Glu Val Ser Ala Pro Arg Leu Arg Asn Trp Ala Gly Asn Ile Ala
                85                  90                  95

Phe Arg Pro Arg Arg Tyr Val Gln Pro Arg Asp Leu Asp Glu Leu Val
            100                 105                 110

Glu Ile Ile Arg Val Ser Asp Gln Val Arg Val Leu Gly Thr Gly His
        115                 120                 125

Ser Phe Asn Pro Ile Ala Asp Thr Thr Gly Thr Leu Ile Ser Leu Asp
    130                 135                 140

His Leu Pro Arg Glu Val Arg Val Met Pro Gly Arg Thr Ala Val Ser
145                 150                 155                 160

Ala Gly Thr Arg Tyr Gly Asp Leu Ala Phe Pro Leu His Glu Ala Gly
                165                 170                 175

Trp Ala Leu Ala Asn Val Gly Ser Leu Pro His Ile Ser Ile Ala Gly
            180                 185                 190

Ala Cys Ala Thr Ala Thr His Gly Ser Gly Asp Arg Asn Gly Cys Leu
        195                 200                 205

Ala Thr Ala Val Ala Gly Met Thr Gly Val Asp Gly Thr Cys Arg Val
    210                 215                 220

Phe His Leu Thr Ala Glu Ser Pro Glu Phe Pro Gly Ala Val Val His
225                 230                 235                 240

Leu Gly Ala Leu Gly Ala Val Thr Glu Ile Glu Leu Val Thr Glu Pro
                245                 250                 255

Thr Phe Thr Val Arg Gln Trp Val Tyr Glu Asp Ala Pro Leu Asp Asn
            260                 265                 270

Val Phe Ala Asp Leu Asp Asp Val Thr Ser Ala Ala Tyr Ser Val Ser
        275                 280                 285

Ile Phe Thr Thr Trp Asp Pro Pro Thr Ala Arg Gln Ile Trp Leu Lys
    290                 295                 300

Glu Arg Val Ala Ala Gly Arg Pro Asp Pro Pro Ala Arg Arg Trp Gly
305                 310                 315                 320
```

```
Gly Arg Leu Ala Glu Arg Asp His Asn Pro Val Pro Gly Met Pro Pro
                325                 330                 335

Glu Asn Cys Thr Pro Gln Leu Gly Arg Ile Gly Pro Trp His Glu Arg
            340                 345                 350

Leu Pro His Phe Arg Leu Asp Val Thr Pro Ser Ala Gly Asp Glu Leu
        355                 360                 365

Gln Ser Glu Tyr Phe Val Pro Arg Ala Ala Val Glu Ala Tyr Arg
    370                 375                 380

Ala Leu Arg His Ile Gly Ser Arg Ile Ala Pro Val Leu Gln Ile Ser
385                 390                 395                 400

Glu Ile Arg Thr Val Ala Ala Asp Glu Leu Trp Leu Ser Pro Ala Tyr
                405                 410                 415

His Arg Pro Ser Val Ala Phe His Phe Thr Trp Ile Ala Asp Glu Glu
            420                 425                 430

Ala Val Arg Pro Val Val Ser Glu Val Glu Arg Ala Leu Ala Pro Leu
        435                 440                 445

Gln Pro Arg Pro His Trp Gly Lys Leu Phe Thr Met Asp Pro Ala Val
    450                 455                 460

Val Arg Ala Ala Tyr Pro Arg Phe Asp Asp Phe Val Ala Leu Ala Glu
465                 470                 475                 480

Arg Tyr Asp Pro Glu Gly Lys Phe Gln Asn Asp Phe Leu Arg Arg Phe
                485                 490                 495

Phe Ala Gly

<210> SEQ ID NO 36
<211> LENGTH: 27
<212> TYPE: PRT
<213> ORGANISM: Bacillus circulans

<400> SEQUENCE: 36

Met Lys Lys Phe Leu Lys Ser Thr Ala Ala Leu Ala Leu Gly Leu Ser
1               5                   10                  15

Leu Thr Phe Gly Leu Phe Ser Pro Ala Gln Ala
            20                  25

<210> SEQ ID NO 37
<211> LENGTH: 480
<212> TYPE: PRT
<213> ORGANISM: Artificial
<220> FEATURE:
<223> OTHER INFORMATION: synthetic fusion protein

<400> SEQUENCE: 37

Met Lys Lys Phe Leu Lys Ser Thr Ala Ala Leu Ala Leu Gly Leu Ser
1               5                   10                  15

Leu Thr Phe Gly Leu Phe Ser Pro Ala Gln Ala Met Asp Gly Gly Lys
            20                  25                  30

Arg Cys Arg Asp Gly Thr Pro Gln Pro Ala Pro Ser Glu Gln Val
        35                  40                  45

Thr Pro Ser Ala Ala Ser Leu Arg Ala Ala Tyr Asp Val Glu Val
    50                  55                  60

Ser Ala Pro Arg Leu Arg Asn Trp Ala Gly Asn Ile Ala Phe Arg Pro
65                  70                  75                  80

Arg Arg Tyr Val Gln Pro Arg Asp Leu Asp Glu Leu Val Glu Ile Ile
                85                  90                  95

Arg Val Ser Asp Gln Val Arg Val Leu Gly Thr Gly His Ser Phe Asn
```

```
                 100                 105                 110
Pro Ile Ala Asp Thr Thr Gly Thr Leu Ile Ser Leu Asp His Leu Pro
            115                 120                 125

Arg Glu Val Arg Val Met Pro Gly Arg Thr Ala Val Ser Ala Gly Thr
130                 135                 140

Arg Tyr Gly Asp Leu Ala Phe Pro Leu His Glu Ala Gly Trp Ala Leu
145                 150                 155                 160

Ala Asn Val Gly Ser Leu Pro His Ile Ser Ile Ala Gly Ala Cys Ala
            165                 170                 175

Thr Ala Thr His Gly Ser Gly Asp Arg Asn Gly Cys Leu Ala Thr Ala
            180                 185                 190

Val Ala Gly Met Thr Gly Val Asp Gly Thr Cys Arg Val Phe His Leu
            195                 200                 205

Thr Ala Glu Ser Pro Glu Phe Pro Gly Ala Val Val His Leu Gly Ala
            210                 215                 220

Leu Gly Ala Val Thr Glu Ile Glu Leu Val Thr Glu Pro Thr Phe Thr
225                 230                 235                 240

Val Arg Gln Trp Val Tyr Glu Asp Ala Pro Leu Asp Asn Val Phe Ala
                245                 250                 255

Asp Leu Asp Asp Val Thr Ser Ala Ala Tyr Ser Val Ser Ile Phe Thr
            260                 265                 270

Thr Trp Asp Pro Pro Thr Ala Arg Gln Ile Trp Leu Lys Glu Arg Val
            275                 280                 285

Ala Ala Gly Arg Pro Asp Pro Pro Ala Arg Arg Trp Gly Gly Arg Leu
            290                 295                 300

Ala Glu Arg Asp His Asn Pro Val Pro Gly Met Pro Pro Glu Asn Cys
305                 310                 315                 320

Thr Pro Gln Leu Gly Arg Ile Gly Pro Trp His Glu Arg Leu Pro His
            325                 330                 335

Phe Arg Leu Asp Val Thr Pro Ser Ala Gly Asp Glu Leu Gln Ser Glu
            340                 345                 350

Tyr Phe Val Pro Arg Ala Ala Val Glu Ala Tyr Arg Ala Leu Arg
            355                 360                 365

His Ile Gly Ser Arg Ile Ala Pro Val Leu Gln Ile Ser Glu Ile Arg
            370                 375                 380

Thr Val Ala Ala Asp Glu Leu Trp Leu Ser Pro Ala Tyr His Arg Pro
385                 390                 395                 400

Ser Val Ala Phe His Phe Thr Trp Ile Ala Asp Glu Glu Ala Val Arg
                405                 410                 415

Pro Val Val Ser Glu Val Glu Arg Ala Leu Ala Pro Leu Gln Pro Arg
            420                 425                 430

Pro His Trp Gly Lys Leu Phe Thr Met Asp Pro Ala Val Val Arg Ala
            435                 440                 445

Ala Tyr Pro Arg Phe Asp Asp Phe Val Ala Leu Ala Glu Arg Tyr Asp
            450                 455                 460

Pro Glu Gly Lys Phe Gln Asn Asp Phe Leu Arg Arg Phe Phe Ala Gly
465                 470                 475                 480

<210> SEQ ID NO 38
<211> LENGTH: 447
<212> TYPE: PRT
<213> ORGANISM: Artificial
<220> FEATURE:
<223> OTHER INFORMATION: synthetic fusion protein
```

```
<400> SEQUENCE: 38

Met Lys Lys Phe Leu Lys Ser Thr Ala Ala Leu Ala Leu Gly Leu Ser
 1               5                  10                  15

Leu Thr Phe Gly Leu Phe Ser Pro Ala Gln Ala Met Thr Pro Ala Glu
             20                  25                  30

Lys Asn Trp Ala Gly Asn Ile Thr Phe Gly Ala Lys Arg Leu Cys Val
         35                  40                  45

Pro Arg Ser Val Arg Glu Leu Arg Glu Thr Val Ala Ala Ser Gly Ala
     50                  55                  60

Val Arg Pro Leu Gly Thr Arg His Ser Phe Asn Thr Val Ala Asp Thr
 65                  70                  75                  80

Ser Gly Asp His Val Ser Leu Ala Gly Leu Pro Arg Val Val Asp Ile
                 85                  90                  95

Asp Val Pro Gly Arg Ala Val Ser Leu Ser Ala Gly Leu Arg Phe Gly
             100                 105                 110

Glu Phe Ala Ala Glu Leu His Ala Arg Gly Leu Ala Leu Ala Asn Leu
         115                 120                 125

Gly Ser Leu Pro His Ile Ser Val Ala Gly Ala Val Ala Thr Gly Thr
     130                 135                 140

His Gly Ser Gly Val Gly Asn Arg Ser Leu Ala Gly Ala Val Arg Ala
145                 150                 155                 160

Leu Ser Leu Val Thr Ala Asp Gly Glu Thr Arg Thr Leu Arg Arg Thr
                165                 170                 175

Asp Glu Asp Phe Ala Gly Ala Val Val Ser Leu Gly Ala Leu Gly Val
            180                 185                 190

Val Thr Ser Leu Glu Leu Asp Leu Val Pro Ala Phe Glu Val Arg Gln
        195                 200                 205

Trp Val Tyr Glu Asp Leu Pro Glu Ala Thr Leu Ala Ala Arg Phe Asp
    210                 215                 220

Glu Val Met Ser Ala Ala Tyr Ser Val Ser Val Phe Thr Asp Trp Arg
225                 230                 235                 240

Pro Gly Pro Val Gly Gln Val Trp Leu Lys Gln Arg Val Gly Asp Glu
                245                 250                 255

Gly Ala Arg Ser Val Met Pro Ala Glu Trp Leu Gly Ala Arg Leu Ala
            260                 265                 270

Asp Gly Pro Arg His Pro Val Pro Gly Met Pro Ala Gly Asn Cys Thr
        275                 280                 285

Ala Gln Gln Gly Val Pro Gly Pro Trp His Glu Arg Leu Pro His Phe
    290                 295                 300

Arg Met Glu Phe Thr Pro Ser Asn Gly Asp Glu Leu Gln Ser Glu Tyr
305                 310                 315                 320

Phe Val Ala Arg Ala Asp Ala Val Ala Ala Tyr Glu Ala Leu Ala Arg
                325                 330                 335

Leu Arg Asp Arg Ile Ala Pro Val Leu Gln Val Ser Glu Leu Arg Thr
            340                 345                 350

Val Ala Ala Asp Asp Leu Trp Leu Ser Pro Ala His Gly Arg Asp Ser
        355                 360                 365

Val Ala Phe His Phe Thr Trp Val Pro Asp Ala Ala Val Ala Pro
    370                 375                 380

Val Ala Gly Ala Ile Glu Glu Ala Leu Ala Pro Phe Gly Ala Arg Pro
385                 390                 395                 400

His Trp Gly Lys Val Phe Ser Thr Ala Pro Glu Val Leu Arg Thr Leu
                405                 410                 415
```

```
Tyr Pro Arg Tyr Ala Asp Phe Glu Glu Leu Val Gly Arg His Asp Pro
            420                 425                 430

Glu Gly Thr Phe Arg Asn Ala Phe Leu Asp Arg Tyr Phe Arg Arg
            435                 440                 445

<210> SEQ ID NO 39
<211> LENGTH: 34
<212> TYPE: PRT
<213> ORGANISM: Streptomyces coelicolor

<400> SEQUENCE: 39

Met His Glu Pro His Leu Asp Arg Arg Leu Phe Leu Lys Gly Thr Ala
1               5                   10                  15

Val Thr Gly Ala Ala Leu Ala Leu Gly Ala Thr Ala Ala Pro Thr Ala
            20                  25                  30

Ser Ala

<210> SEQ ID NO 40
<211> LENGTH: 485
<212> TYPE: PRT
<213> ORGANISM: Artificial
<220> FEATURE:
<223> OTHER INFORMATION: synthetic fusion protein

<400> SEQUENCE: 40

Met Gly His Glu Pro His Leu Asp Arg Arg Leu Phe Leu Lys Gly Thr
1               5                   10                  15

Ala Val Thr Gly Ala Ala Leu Ala Leu Gly Ala Thr Ala Ala Pro Thr
            20                  25                  30

Ala Ser Ala Gly Met Arg Thr Val Ser Glu Leu Pro Gly Leu Ser Gly
            35                  40                  45

Ser Thr Gly Ala Gly Ser Ser Ala Pro Glu Leu Asn Trp Ala Gly Asn
    50                  55                  60

Tyr Arg Tyr Thr Ala Ala Ser Ile His Arg Pro Arg Thr Leu Glu Glu
65                  70                  75                  80

Val Gln Glu Val Val Ala Gly Ala Ser Lys Ile Arg Ala Leu Gly Ser
                85                  90                  95

Arg His Ser Phe Asn Ala Ile Ala Asp Ser Pro Gly Ser Leu Val Ser
            100                 105                 110

Leu Glu Asp Leu Asp Pro Gly Ile Arg Ile Asp Ala Ala Thr Arg Thr
        115                 120                 125

Val Thr Val Ser Gly Gly Thr Arg Tyr Gly Thr Leu Ala Glu Gln Leu
    130                 135                 140

Glu Ser Ala Gly Phe Ala Leu Ser Asn Leu Ala Ser Leu Pro His Ile
145                 150                 155                 160

Ser Val Ala Gly Ala Ile Ala Thr Ala Thr His Gly Ser Gly Asp Ala
                165                 170                 175

Asn Gly Asn Leu Ala Thr Ser Val Ala Ala Leu Glu Leu Val Ala Ala
            180                 185                 190

Asp Gly Thr Val His Arg Leu Asn Arg Gly Ser Ser Pro Gly Phe Asp
        195                 200                 205

Gly Ala Val Val Gly Leu Gly Ala Leu Gly Val Val Thr Lys Val Thr
    210                 215                 220

Leu Asp Ile Glu Pro Thr Phe Thr Val Arg Gln Asp Val Phe Glu Ala
225                 230                 235                 240

Leu Pro Trp Asp Thr Val Leu Gly Asn Phe Asp Ala Val Thr Ser Ser
```

```
                    245                 250                 255
Ala Tyr Ser Val Ser Leu Phe Thr Asp Trp Ser Gly Asp Val Ala
            260                 265                 270

Gln Ala Trp Leu Lys Ser Arg Leu Ser Gly Ser Ala Ala Ser Ser Asp
        275                 280                 285

Ala Gly Ser Thr Leu Ala Gly Glu Ala Phe Ala Ala Gly Thr Phe Phe
    290                 295                 300

Gly Gly Thr Arg Ala Gly Val Ala Arg His Pro Leu Pro Gly Val Ser
305                 310                 315                 320

Ala Glu Asn Cys Thr Glu Gln Leu Gly Val Pro Gly Ser Trp Ser Glu
            325                 330                 335

Arg Leu Ala His Phe Arg Met Ala Phe Thr Pro Ser Ser Gly Glu Glu
            340                 345                 350

Leu Gln Ser Glu Phe Phe Val Arg Arg Glu His Ala Val Ala Ala Ile
        355                 360                 365

Gly Glu Leu Arg Ala Leu Ser Asp Arg Ile Thr Pro Leu Leu Leu Val
    370                 375                 380

Ser Glu Ile Arg Thr Val Ala Ala Asp Lys Leu Trp Leu Ser Thr Ala
385                 390                 395                 400

Tyr Gly Gln Asp Ser Val Gly Phe His Phe Thr Trp Lys Gln Arg Gln
            405                 410                 415

Asp Glu Val Glu Lys Val Leu Pro Val Met Glu Glu Ala Leu Ala Pro
        420                 425                 430

Phe Asn Ala Arg Pro His Trp Gly Lys Leu Phe His Ala Gly Ala Asp
    435                 440                 445

Ala Val Ala Glu Leu Tyr Pro Arg Phe Ser Asp Phe Lys Asp Leu Ala
    450                 455                 460

Glu Arg Met Asp Pro Glu Gln Lys Phe Arg Asn Glu Phe Leu Ala Arg
465                 470                 475                 480

Lys Val Phe Gly Asn
            485

<210> SEQ ID NO 41
<211> LENGTH: 1471
<212> TYPE: DNA
<213> ORGANISM: Artificial
<220> FEATURE:
<223> OTHER INFORMATION: synthetic sequence

<400> SEQUENCE: 41
accatgggcc acgagccgca cctggaccgc cgcctgttcc tgaagggcac cgccgtcacc      60
ggcgccgccc tggccctggg cgccaccgcc gccccgaccg cctccgccgg catgcgcacg     120
gtctccgagc tgccgggcct gtcgggctcc accggcgccg gctcctccgc ccccgagctg     180
aactgggccg gcaactaccg ctacaccgcc gcctccatcc accgcccgcg caccctcgag     240
gaggtccagg aggtcgtcgc gggcgcctcc aagatccgcg ccctgggctc cgccactcc      300 ttcaacgcca tcgccgactc cccgggcagc ctggtctccc tcgaggacct ggaccccggc     360
atccgcatcg acgccgccac cgcaccgtc acggtctcgg gcggcacgcg ctacggcacc      420
ctggccgagc agctcgagtc cgccggcttc gccctgtcca acctggcctc cctgccgcac     480
atctccgtcg ccggcgccat cgccaccgcc acccacggct ccgcgacgc caacggcaac      540 ctggccacct ccgtcgccgc cctcgagctg gtcgcggccg acggcaccgt ccaccgcctg     600
aaccgcggct cctccccggg cttcgacggc gcggtcgtcg gcctgggcgc cctgggcgtc     660
```

```
gtcaccaagg tcaccctgga catcgagccg accttcaccg tccgccagga cgtgttcgag      720
gccctgccgt gggacaccgt cctgggcaac ttcgacgccg tcacctcctc cgcctactcc      780
gtgtccctgt tcaccgactg gtccggcgac gacgtcgccc aggcctggct gaagtcccgc      840
ctgtccggct ccgccgcctc ctccgacgcc ggctccaccc tggccggcga ggccttcgcc      900
gccggcacct tcttcggcgg caccgcgcc ggcgtcgccc gccacccgct gccgggcgtg      960
tccgccgaga actgcaccga gcagctgggc gtcccgggct cctggtccga gcgcctggcc     1020
cacttccgca tggccttcac cccgtcctcc ggcgaggagc tgcagtccga gttcttcgtc     1080
cgccgcgagc acgccgtggc cgccatcggc gagctgcgcg ccctgtccga ccgcatcacc     1140
ccgctgctgc tggtctccga gatccgcacc gtcgccgccg acaagctgtg gctgtccacc     1200
gcctacggcc aggactccgt cggcttccac ttcacctgga agcagcgcca ggacgaggtc     1260
gagaaggtcc tgccggtcat ggaggaggcc ctggccccgt caacgcccg ccgcactgg      1320 ggcaagctgt tccacgccgg cgccgacgcc gtcgccgagc tgtacccgcg cttctccgac     1380
ttcaaggacc tggccgagcg catggacccc gagcagaagt tccgcaacga gttcctggcc     1440
cgcaaggtgt tcggcaactg atgaggatcc g                                    1471

<210> SEQ ID NO 42
<211> LENGTH: 1370
<212> TYPE: DNA
<213> ORGANISM: Acidothermus cellulolyticus 11B

<400> SEQUENCE: 42
ccatggatgg cggcaagcgc tgccgcgacg gcaccccgca gccgccggcc ccgtccgagc       60
aggtcacccc gtcggccgcc gcctcccgtgc gggccgccta cgacgtggag gtctccgccc      120
cgcgcctgcg caactgggcc ggcaacatcg ccttccgccc gcgccgctac gtccagccgc      180
gcgacctcga cgagctggtc gagatcatcg ggtctccga ccaggtccgc gtcctgggca      240
ccggccactc cttcaacccc atcgccgaca ccaccggcac cctgatctcc ctggaccacc      300
tgccgcgcga ggtccgcgtc atgccgggcc gcaccgcgt ctccgccggc acccgctacg      360
gcgacctggc cttcccgctg cacgaggcg gctgggccct ggccaacgtc ggctccctgc      420
cgcacatctc catcgccggc gcctgcgcca ggccaccca cggctccggc gaccgcaacg      480
gctgcctggc caccgccgtc gccggcatga ccggcgtcga cggcacctgc cgcgtgttcc      540
acctgaccgc cgagtccccc gagttcccgg cgccgtcgt ccacctgggc gccctgggcg      600
ccgtcaccga gatcgagctg gtcaccgagc cgaccttcac cgtccgccag tgggtctacg      660
aggacgcccc gctggacaac gtgttcgccg acctggacga cgtcacctcc gccgcctact      720
cggtctccat cttcaccacc tgggacccgc cgaccgcccg gcagatctgg ctgaaggagc      780
gcgtcgccgc cggccgccg gacccgccgg ccgccgctg gggcggccgc ctcgccgagc       840
gcgaccacaa ccccgtcccg gggatgccgc ccgagaactg caccccccag ctgggccgca      900
tcggcccgtg gcacgagcgc ctgccgcact tccgcctgga cgtcaccccc tccgcgggcg      960
acgagctgca gtccgagtac ttcgtcccgc gcgccgccgc cgtcgaggcc taccgcgccc     1020
tgcgccacat cggctcccgc atcgccccgg tcctgcagat ctccgagatc cgcaccgtcg     1080
ccgccgacga gctgtggctg tccccggcct accaccgcc gtccgtcgcc ttccacttca     1140
cctggatcgc cgacgaggag gccgtccgcc cggtggtctc cgaggtcgag cgcgccctgg     1200
ccccgctgca gccgcgcccg cactggggca agctgttcac gatggacccg gccgtcgtcc     1260
```

```
gcgccgccta cccgcgcttc gacgacttcg tcgccctggc cgagcgctac gaccccgagg    1320
gcaagttcca gaacgacttc ctgcgccgct tcttcgccgg ctaaggatcc               1370
```